US012702854B2

(12) United States Patent
Ansari et al.

(10) Patent No.: US 12,702,854 B2
(45) Date of Patent: Aug. 11, 2026

(54) SYSTEMS AND METHODS OF MODULATING FUNCTIONALITY OF AN ANIMAL BRAIN USING ARRAYS OF PLANAR COILS CONFIGURED TO GENERATE PULSED ELECTROMAGNETIC FIELDS AND INTEGRATED INTO HEADWEAR

(71) Applicants: Kamran Ansari, Tustin, CA (US); Nadia Ansari, Tustin, CA (US)

(72) Inventors: Kamran Ansari, Tustin, CA (US); Nadia Ansari, Tustin, CA (US)

( * ) Notice: Subject to any disclaimer, the term of this patent is extended or adjusted under 35 U.S.C. 154(b) by 545 days.

(21) Appl. No.: 17/308,426

(22) Filed: May 5, 2021

(65) Prior Publication Data

US 2021/0346711 A1 Nov. 11, 2021

Related U.S. Application Data

(63) Continuation-in-part of application No. 17/065,412, filed on Oct. 7, 2020, now Pat. No. 11,020,603, which (Continued)

(51) Int. Cl.

*A61N 2/00* (2006.01)
*A61N 1/04* (2006.01)
*A61N 2/02* (2006.01)

(52) U.S. Cl.

CPC ........... *A61N 2/006* (2013.01); *A61N 1/0456* (2013.01); *A61N 1/0476* (2013.01); *A61N 2/008* (2013.01); *A61N 2/02* (2013.01)

(58) Field of Classification Search

CPC .... A61N 2/006; A61N 1/0456; A61N 1/0476; A61N 2/008; A61N 2/02; A61N 1/40
See application file for complete search history.

(56) References Cited

U.S. PATENT DOCUMENTS

| | | | |
|---|---|---|---|
| D320,074 | S | 9/1991 | Frost |
| 5,368,544 | A | 11/1994 | Tran |

(Continued)

FOREIGN PATENT DOCUMENTS

| | | | |
|---|---|---|---|
| CN | 1483487 | A | 3/2004 |
| CN | 101284160 | A | 10/2008 |

(Continued)

OTHER PUBLICATIONS

Anthony J. Lisi et al, "A Pulsed Electromagnetic Field Therapy Device for Non-Specific Low Back Pain: A Pilot Randomized Controlled Trial", Mar. 12, 2019, Pain Ther (2019) 8:133-140.

(Continued)

*Primary Examiner* — Alex M Valvis
*Assistant Examiner* — Julie Thi Tran
(74) *Attorney, Agent, or Firm* — Novel IP

(57) ABSTRACT

The present specification discloses a pulsed electromagnetic field system having planar microcoil arrays integrated into clothing. Preferably, each of the planar microcoil arrays has two or more planar microcoils positioned on a substrate. The planar microcoil arrays are connected to a controller configured to generate an electrical current and transmit that electrical current, in accordance with a particular stimulation protocol, to each of the planar microcoil arrays. The system may be used to suppress epileptic seizures or to provide neuroprotection to a person undergoing cardiac arrest or stroke.

22 Claims, 42 Drawing Sheets

Related U.S. Application Data is a continuation-in-part of application No. 16/867,130, filed on May 5, 2020, now Pat. No. 11,517,760, application No. 17/308,426 is a continuation-in-part of application No. 16/867,130, filed on May 5, 2020, now Pat. No. 11,517,760.

(60) Provisional application No. 63/147,861, filed on Feb. 10, 2021, provisional application No. 63/132,756, filed on Dec. 31, 2020, provisional application No. 62/892,751, filed on Aug. 28, 2019, provisional application No. 62/843,727, filed on May 6, 2019.

(56) References Cited

U.S. PATENT DOCUMENTS

| | | | | |
|---|---|---|---|---|
| 5,470,846 | A | 11/1995 | Sandyk | |
| 5,691,324 | A | 11/1997 | Sandyk | |
| 5,691,325 | A | 11/1997 | Sandyk | |
| 5,885,976 | A | 3/1999 | Sandyk | |
| 6,267,720 | B1 * | 7/2001 | Knox | A61N 2/06 600/15 |
| 6,561,968 | B1 | 5/2003 | Dissing | |
| 7,740,574 | B2 | 6/2010 | Pilla | |
| 7,744,524 | B2 | 6/2010 | Pilla | |
| 7,758,490 | B2 | 7/2010 | Pilla | |
| 7,896,797 | B2 | 3/2011 | Pilla | |
| 8,039,031 | B2 | 10/2011 | Baianu | |
| 8,262,556 | B2 | 9/2012 | Fischell | |
| 8,343,027 | B1 | 1/2013 | Dimino | |
| 8,415,123 | B2 | 4/2013 | Pilla | |
| 8,460,167 | B2 | 6/2013 | Chornenky | |
| 8,690,748 | B1 | 4/2014 | Fu | |
| 8,827,886 | B2 | 9/2014 | Chornenky | |
| 8,932,196 | B2 | 1/2015 | Chornenky | |
| 8,944,985 | B2 | 2/2015 | Bonmassar | |
| 8,958,882 | B1 | 2/2015 | Hagedorn | |
| 8,961,385 | B2 | 2/2015 | Pilla | |
| 9,320,913 | B2 * | 4/2016 | Dimino | A61N 1/40 |
| 9,403,028 | B2 | 8/2016 | Greff | |
| 9,410,143 | B1 | 8/2016 | Rudd | |
| 9,415,233 | B2 | 8/2016 | Pilla | |
| 9,427,598 | B2 | 8/2016 | Pilla | |
| 9,433,797 | B2 | 9/2016 | Pilla | |
| 9,440,089 | B2 | 9/2016 | Pilla | |
| 9,486,638 | B2 | 11/2016 | Chornenky | |
| 9,550,067 | B1 | 1/2017 | Fischell | |
| 9,656,096 | B2 | 5/2017 | Pilla | |
| 9,873,000 | B2 | 1/2018 | Moss | |
| 9,968,797 | B2 | 5/2018 | Sham | |
| 10,207,122 | B2 | 2/2019 | Pilla | |
| 10,226,640 | B2 | 3/2019 | Pilla | |
| 10,238,867 | B2 | 3/2019 | Ryaby | |
| 10,350,428 | B2 | 7/2019 | Pilla | |
| 10,398,906 | B2 | 9/2019 | Jin | |
| 10,413,816 | B2 | 9/2019 | Moir | |
| 10,426,967 | B2 | 10/2019 | Pilla | |
| 10,441,807 | B2 | 10/2019 | Moffett | |
| 10,471,272 | B2 | 11/2019 | Goetz | |
| 10,556,121 | B2 | 2/2020 | Gurfein | |
| D894,404 | S | 8/2020 | Guger | |
| D897,548 | S | 9/2020 | Liu | |
| 10,806,942 | B2 | 10/2020 | Hochstenbach | |
| 11,020,603 | B2 | 6/2021 | Ansari | |
| D1,006,240 | S | 11/2023 | Ansari | |
| D1,006,241 | S | 11/2023 | Ansari | |
| 2001/0047301 | A1 | 11/2001 | Walker | |
| 2002/0032667 | A1 | 3/2002 | Walker | |
| 2002/0035358 | A1 | 3/2002 | Wang | |
| 2002/0036367 | A1 | 3/2002 | Walmer | |
| 2002/0043301 | A1 | 4/2002 | Walmer | |
| 2002/0052634 | A1 | 5/2002 | March | |
| 2002/0066702 | A1 | 6/2002 | Liu | |
| 2002/0165583 | A1 | 11/2002 | Tepper | |
| 2002/0165771 | A1 | 11/2002 | Walker | |
| 2002/0188164 | A1 | 12/2002 | Loos | |
| 2003/0054888 | A1 | 3/2003 | Walker | |
| 2003/0094911 | A1 | 5/2003 | Chukanov | |
| 2003/0153965 | A1 | 8/2003 | Supronowicz | |
| 2003/0158583 | A1 * | 8/2003 | Burnett | A61N 2/006 607/2 |
| 2003/0158585 | A1 | 8/2003 | Burnett | |
| 2003/0233122 | A1 | 12/2003 | Azure | |
| 2004/0034388 | A1 | 2/2004 | Azure | |
| 2004/0039639 | A1 | 2/2004 | Walker | |
| 2004/0116176 | A1 | 6/2004 | Tulley | |
| 2004/0140352 | A1 | 7/2004 | Walker | |
| 2004/0176803 | A1 | 9/2004 | Whelan | |
| 2004/0176805 | A1 | 9/2004 | Whelan | |
| 2004/0181115 | A1 | 9/2004 | Sandyk | |
| 2004/0210254 | A1 | 10/2004 | Burnett | |
| 2004/0241311 | A1 | 12/2004 | Baianu | |
| 2005/0024260 | A1 | 2/2005 | Johnston | |
| 2005/0043994 | A1 | 2/2005 | Walker | |
| 2005/0049640 | A1 | 3/2005 | Gurtner | |
| 2005/0084962 | A1 | 4/2005 | Simon | |
| 2005/0104768 | A1 | 5/2005 | Johnston | |
| 2005/0110837 | A1 | 5/2005 | Silverbrook | |
| 2005/0187012 | A1 | 8/2005 | Walker | |
| 2005/0220674 | A1 | 10/2005 | Shafirstein | |
| 2005/0271738 | A1 | 12/2005 | Simon | |
| 2006/0030896 | A1 | 2/2006 | Simon | |
| 2006/0052658 | A1 | 3/2006 | Ozpapu | |
| 2006/0057693 | A1 | 3/2006 | Simon | |
| 2006/0063963 | A1 | 3/2006 | Brunelle | |
| 2006/0129205 | A1 * | 6/2006 | Boveja | A61N 1/3605 607/45 |
| 2006/0129456 | A1 | 6/2006 | Walker | |
| 2006/0223616 | A1 | 10/2006 | Tulley | |
| 2006/0223617 | A1 | 10/2006 | Tulley | |
| 2006/0224456 | A1 | 10/2006 | Walker | |
| 2006/0229944 | A1 | 10/2006 | Walker | |
| 2006/0229945 | A1 | 10/2006 | Walker | |
| 2006/0241333 | A1 | 10/2006 | Hunter | |
| 2006/0241720 | A1 | 10/2006 | Woods | |
| 2006/0241965 | A1 | 10/2006 | Walker | |
| 2006/0241966 | A1 | 10/2006 | Walker | |
| 2006/0246991 | A1 | 11/2006 | Tulley | |
| 2007/0010314 | A1 | 1/2007 | Tulley | |
| 2007/0026929 | A1 | 2/2007 | Tulley | |
| 2007/0050711 | A1 | 3/2007 | Walker | |
| 2007/0060477 | A1 | 3/2007 | Pedersen | |
| 2007/0066995 | A1 | 3/2007 | Strother | |
| 2007/0067004 | A1 | 3/2007 | Boveja | |
| 2007/0073773 | A1 | 3/2007 | Walker | |
| 2007/0073774 | A1 | 3/2007 | Walker | |
| 2007/0073775 | A1 | 3/2007 | Walker | |
| 2007/0104694 | A1 | 5/2007 | Quijano | |
| 2007/0105769 | A1 | 5/2007 | Simon | |
| 2007/0125851 | A1 | 6/2007 | Walker | |
| 2007/0167213 | A1 | 7/2007 | Tulley | |
| 2007/0167214 | A1 | 7/2007 | Tulley | |
| 2007/0167990 | A1 | 7/2007 | Mangrum | |
| 2007/0187539 | A1 | 8/2007 | Hoppe | |
| 2007/0260107 | A1 * | 11/2007 | Mishelevich | A61N 2/004 600/14 |
| 2007/0282388 | A1 | 12/2007 | Sandyk | |
| 2008/0059318 | A1 | 3/2008 | Packes | |
| 2008/0103558 | A1 | 5/2008 | Wenzel | |
| 2008/0125617 | A1 | 5/2008 | Puchek | |
| 2008/0201232 | A1 | 8/2008 | Walker | |
| 2008/0204021 | A1 * | 8/2008 | Leussler | G01R 33/3415 324/318 |
| 2008/0208663 | A1 | 8/2008 | Walker | |
| 2008/0217263 | A1 | 9/2008 | Higgins | |
| 2008/0229795 | A1 | 9/2008 | Toeniskoetter | |
| 2008/0249879 | A1 | 10/2008 | Walker | |
| 2008/0280826 | A1 | 11/2008 | O'Connor | |
| 2008/0288035 | A1 | 11/2008 | Gill | |
| 2008/0300912 | A1 | 12/2008 | Packes, Jr. | |
| 2009/0013583 | A1 | 1/2009 | Leung | |
| 2009/0163762 | A1 | 6/2009 | Setti | |
| 2009/0171417 | A1 | 7/2009 | Philipson | |
| 2009/0208598 | A1 | 8/2009 | Novitsky | |

(56) References Cited

U.S. PATENT DOCUMENTS

2009/0224037 A1 9/2009 Walker
2009/0227831 A1 9/2009 Burnett
2009/0254531 A1 10/2009 Walker
2009/0299128 A1 12/2009 Setti
2009/0304542 A1 12/2009 Sterling
2009/0310331 A1 12/2009 Leung
2010/0049262 A1 2/2010 Puchek
2010/0057146 A1 3/2010 Gleim
2010/0121131 A1 5/2010 Mathes
2010/0130945 A1 5/2010 Laniado
2010/0160712 A1 6/2010 Burnett
2010/0185523 A1 7/2010 Tulley
2010/0210893 A1 8/2010 Pilla
2010/0211174 A1 8/2010 Scarborough
2010/0222630 A1 9/2010 Mangrum
2010/0233305 A1 9/2010 Farzamfar
2010/0239544 A1 9/2010 Simon
2010/0274177 A1 10/2010 Rybski
2010/0286470 A1* 11/2010 Schneider .............. A61N 2/006 600/14
2011/0004261 A1 1/2011 Sham
2011/0065976 A1 3/2011 Chornenky
2011/0105959 A1 5/2011 O'Connor
2011/0112352 A1 5/2011 Pilla
2011/0124717 A1 5/2011 O'Connor
2011/0125287 A1 5/2011 Hotter
2011/0130618 A1 6/2011 Ron Edoute
2011/0152667 A1 6/2011 Doerr
2011/0152672 A1 6/2011 Doerr
2011/0152674 A1 6/2011 Doerr
2011/0152972 A1 6/2011 Doerr
2011/0207989 A1 8/2011 Pilla
2011/0248019 A1 10/2011 Chew
2011/0283607 A1 11/2011 Gleim
2011/0302161 A1 12/2011 Walker
2011/0313235 A1 12/2011 Gleim
2012/0010559 A1 1/2012 Higgins
2012/0064594 A1 3/2012 Van Bree
2012/0071235 A1 3/2012 Walker
2012/0101327 A1 4/2012 Dissing
2012/0116149 A1 5/2012 Pilla
2012/0143285 A1 6/2012 Wang
2012/0157747 A1 6/2012 Rybski
2012/0172653 A1 7/2012 Chornenky
2012/0184801 A1* 7/2012 Simon ................ A61N 1/36025 607/45
2012/0184802 A1 7/2012 Gleim
2012/0191159 A1 7/2012 Willeford
2012/0205558 A1 8/2012 Jindal
2012/0209055 A1 8/2012 Gleim
2012/0330090 A1 12/2012 Sham
2012/0330771 A1 12/2012 Walker
2013/0035538 A1 2/2013 Maestu Unturbe
2013/0035539 A1 2/2013 Kornstein
2013/0062193 A1 3/2013 Proudkii
2013/0085317 A1 4/2013 Feinstein
2013/0158634 A1 6/2013 Ron Edoute
2013/0164736 A1 6/2013 Bernardi
2013/0178425 A1 7/2013 Higgins
2013/0211896 A1 8/2013 Walker
2013/0218700 A1 8/2013 Walker
2013/0238062 A1 9/2013 Ron Edoute
2013/0274540 A1 10/2013 Pilla
2013/0289433 A1* 10/2013 Jin ........................ A61N 2/008 600/15
2013/0317282 A1 11/2013 Ron Edoute
2013/0328552 A1 12/2013 Chen
2013/0334857 A1 12/2013 Wolsiefer
2014/0024882 A1 1/2014 Chornenky
2014/0046116 A1 2/2014 Gleim
2014/0072926 A1 3/2014 Valoir
2014/0081070 A1 3/2014 Paukshto
2014/0102947 A1 4/2014 Baym
2014/0152227 A1 6/2014 Tuval
2014/0155680 A1 6/2014 Higgins
2014/0171789 A1 6/2014 Barth
2014/0175330 A1 6/2014 Black
2014/0213843 A1 7/2014 Pilla
2014/0213844 A1 7/2014 Pilla
2014/0221726 A1 8/2014 Pilla
2014/0249354 A1 9/2014 Anderson
2014/0249355 A1 9/2014 Martinez
2014/0274893 A1 9/2014 Woodell-May
2014/0274894 A1 9/2014 Leach
2014/0274895 A1 9/2014 Binder
2014/0276182 A1 9/2014 Helekar
2014/0330067 A1 11/2014 Jordan
2014/0350431 A1 11/2014 Hagedorn
2014/0378812 A1 12/2014 Saroka
2015/0025299 A1 1/2015 Ron Edoute
2015/0141737 A1 5/2015 Willeford
2015/0151136 A1 6/2015 Ruetenik
2015/0198381 A1 7/2015 Kuehl
2015/0217125 A1 8/2015 Chornenky
2015/0297910 A1 10/2015 Dimino
2015/0300299 A1 10/2015 Licitar
2015/0306412 A1* 10/2015 Durschmidt ............. A61N 2/02 600/14
2015/0315539 A1 11/2015 Villanueva
2015/0320697 A1 11/2015 O'Connor
2015/0328447 A1 11/2015 Krekelberg
2015/0328476 A1 11/2015 Anderson
2015/0342661 A1 12/2015 Ron Edoute
2015/0366999 A1 12/2015 Amritphale
2016/0038753 A1 2/2016 Chornenky
2016/0051827 A1 2/2016 Ron Edoute
2016/0074670 A1 3/2016 Mohamed
2016/0121135 A1 5/2016 Pilla
2016/0129273 A1 5/2016 Park
2016/0129274 A1 5/2016 Park
2016/0145571 A1 5/2016 Giampapa
2016/0220083 A1 8/2016 Thorne
2016/0228721 A1 8/2016 Mohamed
2016/0228723 A1 8/2016 Mohamed
2016/0346561 A1 12/2016 Ron Edoute
2016/0372362 A1 12/2016 Signamarcheix
2017/0001201 A1 1/2017 Baym
2017/0043177 A1 2/2017 Ron Edoute
2017/0050019 A1 2/2017 Ron Edoute
2017/0071977 A1 3/2017 Mohamed
2017/0072210 A1 3/2017 Gangwish
2017/0080245 A1 3/2017 Dimino
2017/0087367 A1 3/2017 Weisend
2017/0113060 A1 4/2017 Anderson
2017/0151442 A1 6/2017 Walborn
2017/0157318 A1 6/2017 Balakrishnan
2017/0165496 A1 6/2017 Pilla
2017/0175521 A1 6/2017 Pirolli
2017/0189710 A1 7/2017 Goetz
2017/0225004 A1 8/2017 Casse
2017/0266459 A1 9/2017 Mohamed
2017/0304642 A1 10/2017 Ron Edoute
2017/0333725 A1 11/2017 Hotani
2017/0354830 A1 12/2017 Moffett
2018/0001102 A1 1/2018 Henry
2018/0028831 A1 2/2018 Ron Edoute
2018/0043172 A1 2/2018 Serrano Carmona
2018/0043174 A1 2/2018 Gurfein
2018/0071140 A1 3/2018 Sheydin
2018/0104484 A1 4/2018 Ryaby
2018/0110960 A1 4/2018 Youngblood
2018/0126185 A1 5/2018 Hochstenbach
2018/0133498 A1 5/2018 Chornenky
2018/0140861 A1 5/2018 Dimino
2018/0200503 A1 7/2018 Ryaby
2018/0200531 A1 7/2018 Pilla
2018/0207439 A1* 7/2018 Cook ...................... H01F 7/064
2018/0272149 A1 9/2018 Anderson
2018/0318598 A1 11/2018 Russo
2018/0361144 A1 12/2018 Omar-Pasha
2019/0021277 A1 1/2019 Godfrey
2019/0054308 A1 2/2019 Verma
2019/0082990 A1 3/2019 Poltorak
2019/0091474 A1 3/2019 Zeng

(56) References Cited

U.S. PATENT DOCUMENTS

| | | | |
|---|---|---|---|
| 2019/0126036 | A1 | 5/2019 | Franco-Obregon |
| 2019/0201280 | A1 | 7/2019 | Bak |
| 2019/0217090 | A1 | 7/2019 | Ryaby |
| 2019/0247662 | A1 | 8/2019 | Poltroak |
| 2019/0255363 | A1 | 8/2019 | Gangwish |
| 2019/0290925 | A1 | 9/2019 | Gellman |
| 2019/0296589 | A1 | 9/2019 | Ardavan |
| 2019/0299018 | A1 | 10/2019 | Chornenky |
| 2019/0323345 | A1 | 10/2019 | Pirolli |
| 2019/0329065 | A1 | 10/2019 | Gandel |
| 2019/0336782 | A1 | 11/2019 | Shealy |
| 2019/0343702 | A1 | 11/2019 | Smith |
| 2019/0351249 | A1 | 11/2019 | Pilla |
| 2019/0365803 | A1 | 12/2019 | Melosh |
| 2019/0381331 | A1 | 12/2019 | Gleim |
| 2019/0388676 | A1 | 12/2019 | Babico |
| 2020/0001101 | A1 | 1/2020 | Moffett |
| 2020/0016422 | A1 | 1/2020 | Ron Edoute |
| 2020/0016423 | A1 | 1/2020 | Ron Edoute |
| 2020/0069960 | A1 | 3/2020 | Walborn |
| 2020/0077942 | A1 | 3/2020 | Youngblood |
| 2020/0094066 | A1 | 3/2020 | Heath |
| 2020/0094068 | A1 | 3/2020 | Dimino |
| 2020/0171318 | A1 | 6/2020 | Dimino |
| 2020/0206523 | A1 | 7/2020 | Kirk |
| 2020/0238098 | A1 | 7/2020 | Chornenky |
| 2020/0276435 | A1 | 9/2020 | Ryaby |
| 2020/0285131 | A1 | 9/2020 | Marandi |
| 2020/0289837 | A1 | 9/2020 | Lowin |
| 2020/0289841 | A1 | 9/2020 | Mcintyre |
| 2020/0306554 | A1 | 10/2020 | Ron Edoute |
| 2020/0353274 | A1 | 11/2020 | Ansari |
| 2021/0251850 | A1 | 8/2021 | Sharma |
| 2021/0283411 | A1 | 9/2021 | Dietz |
| 2021/0346711 | A1 | 11/2021 | Ansari |
| 2022/0047883 | A1 | 2/2022 | Dietz |
| 2024/0032848 | A1 | 2/2024 | Hwang |

FOREIGN PATENT DOCUMENTS

| | | | | | |
|---|---|---|---|---|---|
| CN | 104519953 | A | | 4/2015 | |
| EP | 1723985 | B1 | | 3/2008 | |
| KR | 100846091 | B1 | | 7/2008 | |
| WO | WO-0115774 | A2 | * | 3/2001 | ............... A61N 2/02 |
| WO | 2004011631 | A2 | | 2/2004 | |
| WO | 2004103098 | A2 | | 12/2004 | |
| WO | WO-2010017249 | A1 | * | 2/2010 | ......... A61N 1/36014 |
| WO | WO-2010067336 | A2 | * | 6/2010 | ............. A61N 2/006 |
| WO | 2010124234 | A1 | | 10/2010 | |
| WO | 2011011748 | A1 | | 1/2011 | |
| WO | 2012033932 | A2 | | 3/2012 | |
| WO | 2012045079 | A2 | | 4/2012 | |
| WO | 2015161063 | A1 | | 10/2015 | |
| WO | 2016081952 | A1 | | 5/2016 | |
| WO | 2018075394 | A1 | | 4/2018 | |
| WO | 2020041502 | A1 | | 2/2020 | |
| WO | WO-2020141165 | A1 | * | 7/2020 | ............. A61N 2/004 |
| WO | 2021183410 | A1 | | 9/2021 | |

OTHER PUBLICATIONS

Mingke Jiao et al, "Effects of Low-Frequency Pulsed Electromagnetic Fields on High-Altitude Stress Ulcer Healing in Rats", Hindawi BioMed Research International, vol. 2019, Article ID 6354054, 8 pages.

Sujith Vijayan et al, "Thalamic model of awake alpha oscillations and implications for stimulus processing", PNAS Nov. 6, 2012 109 (45) 18553-18558.

Tommaso Iannitti et al, "Pulsed electromagnetic field therapy for management of osteoarthritis-related pain, stiffness and physical function: clinical experience in the elderly", Published Sep. 26, 2013, Clinical Interventions in Aging 2013:8 1289-1293.

Yvan Touitou et al, "The effects of extremely low-frequency magnetic fields on melatonin and cortisol, two marker rhythms of the circadian system", Dialogues in Clinical Neuroscience—vol. 14 . No. 4 . 2012.

Alanna V Van Huizen et al, "Weak magnetic fields alter stem cell-mediated growth", Sci Adv. Jan. 30, 2019;5(1):eaau7201.

Pierre Le Chapellier et al, "Cellular Perception and Static Magnetic Fields Active Penetration Depth for Pain Magnetotherapy", Piers Online, vol. 6, No. 3, 2010.

Maria Vadala et al, "Mechanisms and therapeutic effectiveness of pulsed electromagnetic field therapy in oncology", Cancer Medicine 2016; 5(11):3128-3139.

Renate Gehwolf et al, "Global Responses of Il-1β-Primed 3D Tendon Constructs to Treatment with Pulsed Electromagnetic Fields", Published: Apr. 30, 2019, Cells 2019, 8(5), 399.

Rachel Lai-Chu Kwan et al, "Efficacy of Biophysical Energies on Healing of Diabetic Skin Wounds in Cell Studies and Animal Experimental Models: A Systematic Review", Jan. 16, 2019, Int. J. Mol. Sci. 2019, 20(2), 368.

Peter Kovacic et al, "Electromagnetic fields: mechanism, cell signaling, other bioprocesses, toxicity, radicals, antioxidants and beneficial effects", Journal of Receptors and Signal Transduction, 2010; 30(4): 214-226.

Wenjun Xu et al, "Effect of pulsed millisecond current magnetic field on the proliferation of C6 rat glioma cells", Electromagnetic Biology and Medicine, 2019, vol. 38, No. 3, 185-197.

Connie X. Wang et al, "Transduction of the Geomagnetic Field as Evidenced from alpha-Band Activity in the Human Brain", eNeuro, Mar./Apr. 2019, 6(2) e0483-18.2019 1-23.

Christina L. Ross et al, "Targeting Mesenchymal Stromal Cells/Pericytes (MSCs) With Pulsed Electromagnetic Field (PEMF) Has the Potential to Treat Rheumatoid Arthritis", Mar. 4, 2019, Frontiers in Immunology, vol. 10: Article 266.

Masoomeh Kazemi et al, "Effects of the Extremely Low Frequency Electromagnetic Fields on NMDA-Receptor Gene Expression and Visual Working Memory in Male Rhesus Macaques", May, Jun. 2018, Basic and Clinical Neuroscience, 9(3), 167-176.

Yue Li et al, "Effects of pulsed electromagnetic fields on learning and memory abilities of STZ-induced dementia rats", Mar. 17, 2019, Electromagnetic Biology and Medicine, 38:2, 123-130.

Igor Jerman et al, "Enhancing Vigilance by Low Intensity Transcranial Pulsed Magnetic Stimulation Applying the Entrainment Model", Oct. 17, 2019, Open Access Library Journal , 6: e5782.

Igor Jerman et al, "Influencing Relaxation by a Low Intensity Transcranial Pulsed Magnetic Stimulation Applying the Entrainment Model", Sep. 17, 2019, Open Access Library Journal, 6: e5741.

Laura Baker-Price et al, "Intermittent Burst-Firing Weak (1 Microtesla) Magnetic Fields Reduce Psychometric Depression in Patients who Sustained Closed Head Injuries: a Replication and Electroencephalographic Validation", Perceptual and MotorSkils, 2003,96,965-974.

Kalina Makowiecki et al, "Low-intensity repetitive transcranial magnetic stimulation requires concurrent visual system activity to modulate visual evoked potentials in adult mice", Apr. 11, 2018, Scientific Reports, vol. 8, Article No. 5792 (2018).

John A. Robertson, "Magnetic Field Effects on the Neuroprocessing of Pain", Aug. 2011, Electronic Thesis and Dissertation Repository, Paper 236.

Mahtab Roohi-Azizi et al, "Changes of the brain's bioelectrical activity in cognition, consciousness, and some mental disorders", Med J Islam Repub Iran. 2017(Sep. 3); 31.53.

G. Bard Ermentrout et al, "Modeling neural oscillations", Sep. 6, 2002, Physiology & Behavior 77 (2002) 629-633.

Nermeen Mohamed Abdelhalim et al, "Short-Term impacts of pulsed electromagnetic field therapy in middle-aged university's employees with non-specific low back pain: A pilot study", Pak J Med Sci. 2019; 35(4):987-991.

Rachel Lai-Chu Kwan et al, "Pulsed Electromagnetic Field Therapy Promotes Healing and Microcirculation of Chronic Diabetic Foot Ulcers: A Pilot Study", May 2015, Advances in Skin & Wound Care, vol. 28, No. 5.

(56) References Cited

OTHER PUBLICATIONS

Magor L. Lörincz et al, “Temporal Framing of Thalamic Relay-Mode Firing by Phasic Inhibition during the Alpha Rhythm”, Neuron. Sep. 10, 2009; 63(5): 683-696.
Chul-Ho Kim et al, “The impact of pulsed electromagnetic field therapy on blood pressure and circulating nitric oxide levels: a double blind, randomized study in subjects with metabolic syndrome”, Aug. 8, 2019, Blood Pressure, 29:1, 47-54.
International Search Report for PCT/US20/31467, Aug. 31, 2020.
Written Opinion of the International Search Authority for PCT/US20/31467, Aug. 31, 2020.
International Search Report for PCT/US21/30826, Sep. 8, 2021.
Written Opinion of the International Search Authority for PCT/US21/30826, Sep. 8, 2021.
OmniPENF—OmniPENF Distibutors; Become an Authorized Distributor. Contact page [online]. Cell Technologies, Inc.; Aug. 22, 2018 [retrieved on Feb. 2, 2022]. Retrieved from the Internet: <URL:https://web.archive.org/web/20180822093113/https://omnipemf.com/>.
OSKA Pulse Buy Now/How It Works; Doctor Recommended OSKA Pulse Clinically Proven Pain Relief. Purchase Page [online]. Oska Wellness; Apr. 5, 2019 [retrived on Feb. 4, 2022]. Retrieved from the Internet: <URL:https://web.archive.org/web/20190405101216/https://www.oskawellness.com/>.

* cited by examiner

Figure 3 Type II micro coil design. The width, spacing and thickness of the coil are 200 μm, 160 μm and 20 μm, respectively.

(a)

(b)

(c)

1600

1800a

2700B

2700A

3002 — EEG electrodes are configured to detect brain waves and generate corresponding analog signals 3004 — Analog signals are transmitted to the controller, which converts it to digital signals, samples the digital signals, and segments the sampled signals into short windows.

3006 — Signals are then subjected to any number of different analytical programs 3008 — Once the controller, executing the EEG detection model, detects a seizure, a signal is generated to initiate current flow to the microcoil arrays, in any one of a number of treatment protocols 3010 — Optionally, EEG detection model is reactivated to continue monitoring for a seizure.

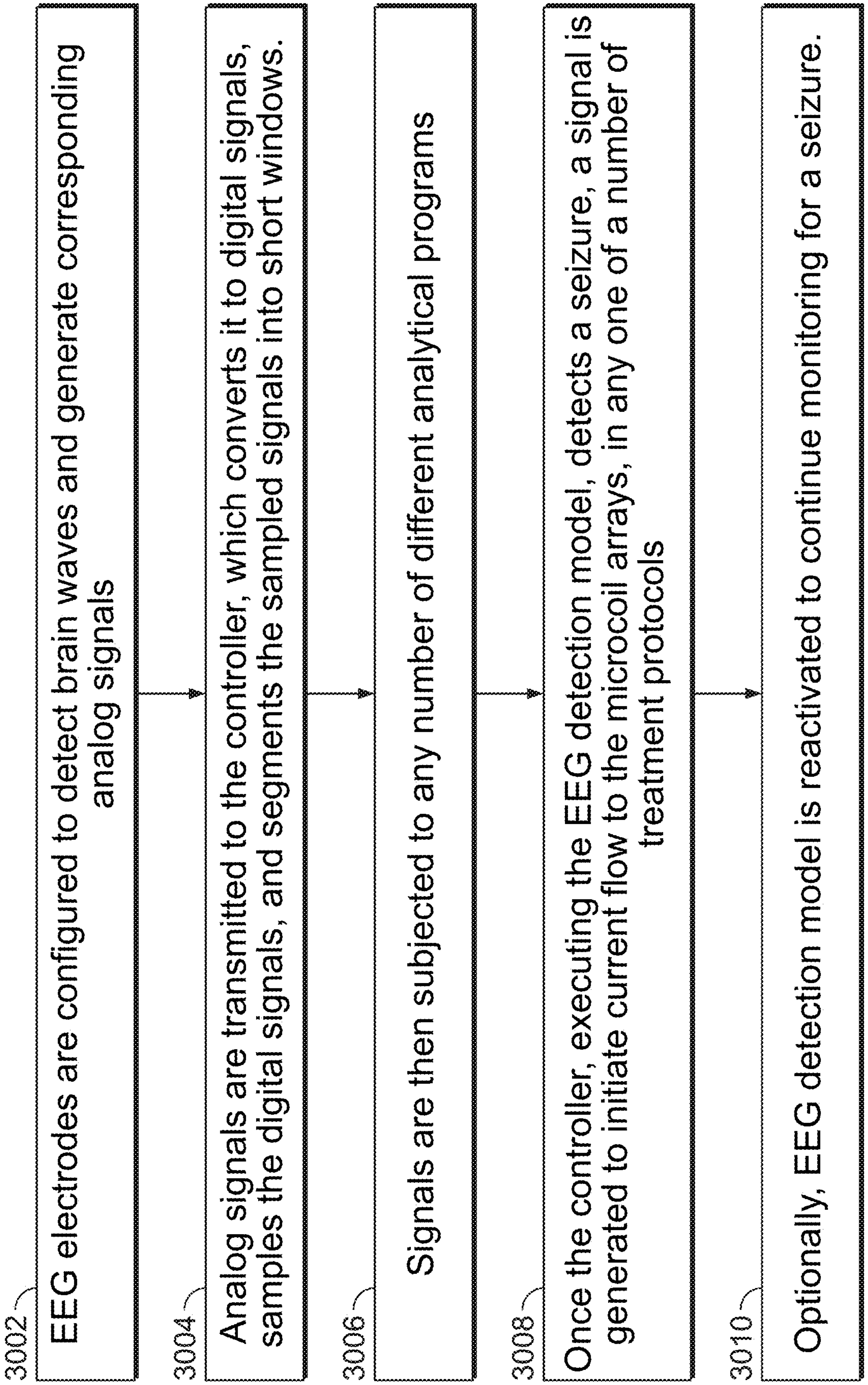

SYSTEMS AND METHODS OF MODULATING FUNCTIONALITY OF AN ANIMAL BRAIN USING ARRAYS OF PLANAR COILS CONFIGURED TO GENERATE PULSED ELECTROMAGNETIC FIELDS AND INTEGRATED INTO HEADWEAR

CROSS-REFERENCE

The present application relies on the following related applications for priority and each of the following applications are incorporated herein by reference:

- US Patent Provisional Application No. 63/147,861, titled "Systems and Methods of Modulating Electrical Impulses in an Animal Brain Using Arrays of Planar Coils Configured to Generate Pulsed Electromagnetic Fields and Integrated into Clothing" and filed on Feb. 10, 2021.
- US Patent Provisional Application No. 63/132,756, titled "Systems and Methods of Modulating Electrical Impulses in an Animal Brain Using Arrays of Planar Coils Configured to Generate Pulsed Electromagnetic Fields and Integrated into Clothing" and filed on Dec. 31, 2020.
- U.S. patent application Ser. No. 17/065,412, titled ""Systems and Methods of Modulating Electrical Impulses in an Animal Brain Using Arrays of Planar Coils Configured to Generate Pulsed Electromagnetic Fields and Integrated into Clothing" and filed on Oct. 7, 2020.
- U.S. patent application Ser. No. 16/867,130, entitled "Systems and Methods of Treating Medical Conditions Using Arrays of Planar Coils Configured to Generate Pulsed Electromagnetic Fields and Integrated into Clothing" and filed on May 5, 2020, which relies on a) US Patent Provisional No. 62/892,751, entitled "Systems and Methods of Treating Medical Conditions Using Arrays of Planar Coils Configured to Generate Pulsed Electromagnetic Fields" and filed on Aug. 28, 2019 and b) US Patent Provisional No. 62/843,727, entitled "Systems and Methods of Treating Medical Conditions Using Arrays of Planar Coils Configured to Generate Pulsed Electromagnetic Fields" and filed on May 6, 2019.

FIELD OF THE INVENTION

The present invention is directed toward modulating brain waves, generated by the brain of an animal, such as a human being, using discrete arrays planar coils. More specifically, the present invention is directed toward the design, creation and use of clothing products, and other devices, that integrate configurations of arrays of planar coils to generate pulsed electromagnetic fields to treat various medical conditions, such as chronic sinus inflammation, anxiety, insomnia, sleep disorders, depression, pain, food cravings, drug dependency, drug addiction, dementia, chronic pain, and/or memory loss and to effectuate improved mood, decreased sinus congestion, increased feelings of well-being, increased energy levels, increased memory, increased creative thinking, decreased anxiety, decreased depression, decreased pain, and/or improved sleep quality of an animal.

BACKGROUND OF THE INVENTION

One recognized approach to treating a number of conditions, including anxiety and depression, is modulating the electrical impulses in a person's brain, typically by electrical stimulation. Electrical stimulation by a transcutaneous electrical stimulation unit (TENS) attached, for example, to a patient's ear has been shown to modulate electrical impulses in the patient's brain, thereby resulting in a modulation of brain wave activity, as shown in electroencephalograms (EEGs).

Certain brain wave profiles are indicative of healthy brain function and may be measured, tracking, and quantified using EEGs. For example, beta waves or rhythms, which are in the range of 13 to 35 Hz, are associated with consciousness, brain activities, and motor behaviors. Alpha waves or rhythms, which are in the range of 7 to 13 Hz, originate from occipital lobes during wakeful relaxation and are associated with relaxation or a meditative state. Theta waves or rhythms, which are in the range of 4 to 7 Hz, are typically recorded when an individual is experiencing low brain activity, sleep, or drowsiness. Delta waves or rhythms, which are in the range of 0 to 4 Hz, are typically recorded during very low activities of the brain and deep sleep. Gamma waves or rhythms, which are in the range of 30 to 100 Hz, are produced by different populations of neurons firing together in a neural network during certain motor or cognitive functions. In particular: 1) mental disorders such as obsessive-compulsive disorder (OCD) can be detected through an EEG, and studies have revealed a decrease in alpha and beta rhythms and an increase in the theta wave in the EGG of OCD patients; 2) anxiety has EEG manifestations including an increased activity of rapid brain waves (beta rhythm), especially in the central part of frontal cortex and the activity of the alpha rhythm is decreased in patients with chronic anxiety; 3) posttraumatic stress disorder (PTSD), which is commonly observed in soldiers and sexual abuse survivors, shows an asymmetry of the alpha rhythm and increased activity of the right parietal lobe, a decrease in alpha rhythms, and an increase in beta rhythms in patients with a long history of PTSD; 4) ADHD patients show a decreased beta activity in comparison with normal children, an increase in theta to beta (θ/β) rhythm and missing alpha wave activity which would otherwise reflect a normal wakeful state; and 5) when a patient's eyes are open, he or she shows a decrease in delta and theta amplitude and frequency waves of alpha and beta in autism spectrum disorder (ASD).

Conventional approaches to beneficially modulating brain wave activity require the use of conspicuous, and often intimidating, medical devices. For example, TENS units exist which require a patient to attach leads to his or her ear, connect to an external stimulator, and periodically apply a current. The application of a current, particularly to the vagus nerve of the patient, may modulate electrical impulses in the brain and, accordingly, modulate brain wave activity. For many people, however, this is intimidating, impractical (particularly in public situations or on the job), and psychologically difficult to do on a regular basis.

Attempts at using pulsed electromagnetic field therapy (PElVfF) therapy are equally conspicuous and undesirable for patients who wish to make treatment a seamless part of daily life. Conventionally, PEMF is delivered by a mat, ring or a small disc device that generates a pulsing electromagnetic field using large cylindrically shaped, non-planar coils, such as Helmholtz coils or butterfly coils, where the winding or turns of the coils extend outward from the surface of the first coil in a Z axis. There are numerous disadvantages with these conventional devices. First, they are difficult to use for long periods of time because they require patients to either lay on a mat or attach a special bulky device to their body, making "therapy" a prominent, conspicuous issue. Therefore, patient compliance is low and extended treatment periods, such as one or more hours, tends to be unrealistic for most active patients. Second, they generate highly localized magnetic fields which tend to only over a small portion of the brain or are substantially non-homogenous across their surface areas. As a result, the surface areas of the devices have regions with very low, non-therapeutic magnetic field dose levels interspersed with regions with sufficiently high, therapeutic doses of magnetic fields, often yielding asymmetrical responses in the patient's anatomy. This can be particularly problematic in the brain where asymmetrically modulating brain wave activity may hurt, rather than help, a patient. Third, these devices often fail to inconspicuously conform to particular body parts, are difficult to position or wear for long periods of time and are challenging to use consistently.

It is therefore desirable to modulate an animal's brain wave activity using a pulse electromagnetic field device that can be comfortably worn for long periods of time, thereby increasing patient compliance and allowing active patients to get the necessary treatment. It would also be desirable to have a pulse electromagnetic field device where the therapeutically effective dose regions are known and/or predictable. Finally, it would also be desirable to have a pulse electromagnetic field device designed to treat a wide range of disorders, particularly disorders with a locus of dysfunction in the brain.

Additionally, chronic pain affects more than 100 million people in the US. The most common underlying biological causes for chronic pain include decreased blood circulation, damaged nerves, and/or increased inflammation. While opioids have been a widely used way of alleviating chronic pain, the medical community now recognizes the substantial disadvantages of prescribing opioids. According to the National Institute of Health, more than 130 people in the United States die every day after overdosing on opioids, 21 to 29 percent of patients prescribed opioids for pain misuse them, and between 8 and 12 percent develop an opioid use disorder. The Centers for Disease Control and Prevention estimates that the total economic burden of prescription opioid misuse alone in the United States is $78.5 billion a year, including the costs of healthcare, lost productivity, addiction treatment, and criminal justice involvement. Therefore, the search is on for a better way to treat pain without relying on highly addictive drugs.

One conventional approach to treating pain is applying pulsing, low frequency electromagnetic fields (PEMF), non-invasively, to the area of the patient's skin where the patient is feeling pain. PEMF therapy uses bursts of low-level electromagnetic radiation to heal damaged tissues and bone and to relieve injury-related pain. The idea is that, when low frequency pulses pass through the skin and penetrate into muscle, nerves, bone and/or tendons, the body's natural repair mechanisms are activated, possibly by normalizing electrical charge distribution in cells, increasing blood perfusion in the affected areas, or improving signaling and/or conduction in nerves.

PEMF therapy has been shown to be effective in regenerating nerves, treating back pain, improving wound healing, countering the effects of Parkinson's disease, and treating peripheral neuropathy, using magnetic fields ranging from picoTesla to Tesla levels. PEMF is a recognized therapy for treating pseudoarthrosis, diabetes mellitus induced complications, delayed wound healing, pain and neurodegenerative disorders and arthritis, and for regenerating musculoskeletal tissues such as cartilage, bone, tendon and ligaments.

As discussed above, conventionally, PEMF therapy is delivered by a mat, ring or a small disc device that generates a pulsing electromagnetic field using large cylindrically shaped, non-planar coils, such as Helmholtz coils or butterfly coils, where the winding or turns of the coils extend outward from the surface of the first coil in a Z axis. There numerous disadvantages with these conventional devices discussed above also apply to the treatment of these conditions.

First, they generate highly localized magnetic fields which tend to only over a small portion of the body or are substantially non-homogenous across their surface areas. As a result, the surface areas of the devices have regions with very low, non-therapeutic magnetic field dose levels interspersed with regions with sufficiently high, therapeutic doses of magnetic fields. Patients, however, are unaware of what surface areas emit therapeutic doses and what surface areas emit non-therapeutic doses, resulting in suboptimal therapy. For example, a patient with a need for PEMF therapy in his or her feet may lay on a mat in a way that the feet are not sufficiently exposed to the requisite magnetic field dose levels.

Second, for patients with extensive peripheral neuropathies, it is very difficult to get all over body PEMF therapy in an efficient manner. For example, a patient with pain all around his or her torso would have to lay on a mat in the right alignment with the surface areas emitting the right therapeutic doses, assuming such areas can be identified, for at least a period of time ranging from 20 minutes to 3 hours and then have to flip over and repeat the process. Again, this is highly inefficient for active patients.

Third, these devices are not specifically designed to treat, or be applied to, specific parts of the body. As such, they often fail to conform to particular body parts, are difficult to position or wear for long periods of time and are to use consistently.

Fourth, commercial PEMF devices, designed for at home use, to treat anxiety disorders, obsessive compulsive disorder, post-traumatic stress disorder, memory degeneration, schizophrenia, Parkinson's disease, stroke rehabilitation, drug addiction, including addiction to, or cravings for, nicotine, cocaine, alcohol, heroine, methamphetamines, stimulants, and/or sedatives, depression and depression-related conditions, such as post-partum depression or bipolar depression, auditory hallucinations, multiple sclerosis, fibromyalgia, Alzheimer's disease, spinocerebellar degeneration, epilepsy, urinary incontinence, movement disorders, chronic tinnitus, and sleep apnea are simply not available and have generally been deemed to be untreatable using PEMF devices.

It is therefore desirable to have a pulse electromagnetic field device that can generate substantially homogenous magnetic fields across large surface areas. It is further desirable to have a pulse electromagnetic field device that can be comfortably worn for long periods of time, thereby increasing patient compliance and allowing active patients to get the necessary treatment. It would also be desirable to have a pulse electromagnetic field device where the therapeutically effective dose regions are known and/or predictable. Finally, it would also be desirable to have a pulse electromagnetic field device designed to treat a wide range of disorders, particularly disorders with a locus of dysfunction in the brain.

SUMMARY OF THE INVENTION

The present specification discloses a pulsed electromagnetic field device configured to direct pulsed electromagnetic fields toward a user's brain, comprising: a hat comprising a crown having an internal surface configured to receive the user's head; a controller configured to be attached to a surface of the hat and configured to generate an electrical current; and at least two planar flexible arrays, wherein: each of the at least two planar flexible arrays comprises at least two planar microcoils integrated into a flexible substrate; the at least two planar microcoils are positioned in a same plane and the plane does not intersect a surface of the user's head; each array of the at least two planar flexible arrays is physically separate and coupled to the internal surface of the crown; each array of the at least two planar flexible arrays is in electrical communication with the controller; and each of the at least two planar microcoils on each of the at least two planar flexible arrays is configured to receive the electrical current to generate separate pulsed electromagnetic fields.

Optionally, the controller is configured to direct the electrical current to each of the at least two planar flexible arrays at different times.

Optionally, the controller is configured to direct the electrical current to each of the at least two planar microcoils in each of the at least two planar flexible arrays in parallel.

Optionally, the controller is configured to direct the electrical current to each of the at least two planar microcoils in each of the at least two planar flexible arrays serially.

Optionally, the controller is configured to direct the electrical current to each of the at least two planar flexible arrays at the same time.

Optionally, the single treatment session is less than 6 contiguous hours.

Optionally, the controller is configured to direct the electrical current to each of the at least two planar flexible arrays such that, over a single treatment session, a same volume of the user's brain is exposed to pulsed electromagnetic fields that change directions depending on which of the at least two planar flexible arrays is receiving the electrical current.

Optionally, the controller is adapted to generate an electrical pulse train having a frequency in a range of 0.1 Hz to 60 Hz and to deliver the electrical pulse train to each array of the at least two planar flexible arrays. Optionally, the electrical pulse train comprises at least two pulses having different peak levels of current wherein the different peak levels of current are in a range of 5 mA to 500 mA. Optionally, a shape of each of the at least two pulses is rectangular.

Optionally, each array of the at least two planar flexible arrays comprises at least 4 spiral-shaped planar microcoils that are each embedded into the flexible substrate. Optionally, the controller is adapted to generate an electrical pulse train that is currently delivered to each of the at least 4 planar microcoils concurrently.

Optionally, the at least two planar flexible arrays comprises at least 5 planar flexible arrays and wherein: a first array of the at least 5 planar flexible arrays is positioned at a front portion of the crown such that, when the hat is worn on the user's head, the first array of the at least 5 planar flexible arrays is positioned adjacent a frontal lobe of the brain within the user's head; a second array of the at least 5 planar flexible arrays is positioned at a right side portion of the crown such that, when the hat is worn on the user's head, the second array of the at least 5 planar flexible arrays is positioned adjacent a right temporal lobe of the brain within the user's head; a third array of the at least 5 planar flexible arrays is positioned at a left side portion of the crown such that, when the hat is worn on the user's head, the third array of the at least 5 planar flexible arrays is positioned adjacent a left temporal lobe of the brain within the user's head; a fourth array of the at least 5 planar flexible arrays is positioned at a top side portion of the crown such that, when the hat is worn on the user's head, the fourth array of the at least 5 planar flexible arrays is positioned adjacent the frontal lobe or a parietal lobe of the brain within the user's head; and a fifth array of the at least 5 planar flexible arrays is positioned at a back side portion of the crown such that, when the hat is worn on the user's head, the fifth array of the at least 5 planar flexible arrays is positioned adjacent a occipital lobe of the brain within the user's head.

Optionally, the controller is adapted to generate an electrical pulse train having a frequency in a range of 0.1 Hz to 100 Hz and to sequentially deliver the electrical pulse train to each of the at least 5 planar flexible arrays.

Optionally, the controller is adapted to generate an electrical pulse train having a frequency in a range of 0.1 Hz to 100 Hz and to concurrently deliver the electrical pulse train to at least 2 of each of the at least 5 planar flexible arrays.

Optionally, the hat comprises two or more layers of material wherein each of the at least 5 planar flexible arrays is positioned between the two or more layers of material.

Optionally, the controller is adapted to generate an electrical pulse train having a frequency and to deliver the electrical pulse train to each array of the at least 5 planar flexible arrays, wherein the electrical pulse train comprises a first pulse having a first amplitude, a second pulse having a second amplitude, and a third pulse having a third amplitude, wherein the first amplitude is less than the second amplitude and the second amplitude is less than the third amplitude. Optionally, each of the first pulse, second pulse, and third pulse has a substantially rectangular shape.

Optionally, each array of the at least 5 planar flexible arrays comprises an input terminal configured to receive current from the controller, an output terminal, and at least two traces to electrically connect each of the at least two planar microcoils positioned on each of the at least 5 planar flexible arrays to the input terminal and the output terminal. Optionally, each array of the at least 5 planar flexible arrays comprises at least four planar microcoils integrated therein, wherein each of the at least four planar microcoils is positioned in the same plane that does not intersect a surface of the user's head.

The present specification also discloses a pulsed electromagnetic field device comprising: a hat comprising a crown having an internal surface configured to receive a human head; a controller configured to be attached to an external surface of the hat; and a plurality of planar microcoil arrays, wherein each array of the plurality of planar microcoil arrays comprises at least one planar microcoil positioned on a substrate, wherein each array of the plurality of planar microcoil arrays is coupled to the internal surface of the crown and wherein each array of the plurality of planar microcoil arrays is in electrical communication with the controller.

Optionally, each array of the plurality of planar microcoil arrays is physically separate and configured to independently receive an electrical current from the controller.

Optionally, the controller is adapted to generate an electrical pulse train having a frequency and to deliver the electrical pulse train to each array of the plurality of planar microcoil arrays. Optionally, the electrical pulse train comprises at least two pulses having different peak levels of current and wherein the different peak levels of current are in a range of 5 mA to 500 mA. A shape of each of the at least two pulses may be rectangular. The frequency may be in a range of 1 Hz to 60 Hz.

Optionally, each array of the plurality of planar microcoil arrays comprises at least 4 spiral-shaped microcoils. Optionally, the controller is adapted to generate an electrical pulse train that is currently delivered to each of the at least 4 microcoils concurrently.

Optionally, the plurality of planar microcoil arrays comprises at least 5 planar microcoil arrays wherein: a first array of the at least 5 planar microcoil arrays is positioned at a front portion of the crown such that, when the hat is worn on the human head, the first array of the at least 5 planar microcoil arrays is positioned adjacent a frontal lobe of a brain within the human head; a second array of the at least 5 planar microcoil arrays is positioned at a right side portion of the crown such that, when the hat is worn on the human head, the second array of the at least 5 planar microcoil arrays is positioned adjacent a right temporal lobe of the brain within the human head; a third array of the at least 5 planar microcoil arrays is positioned at a left side portion of the crown such that, when the hat is worn on the human head, the third array of the at least 5 planar microcoil arrays is positioned adjacent a left temporal lobe of the brain within the human head; a fourth array of the at least 5 planar microcoil arrays is positioned at a top side portion of the crown such that, when the hat is worn on the human head, the fourth array of the at least 5 planar microcoil arrays is positioned adjacent the frontal lobe or a parietal lobe of the brain within the human head; and a fifth array of the at least 5 planar microcoil arrays is positioned at a back side portion of the crown such that, when the hat is worn on the human head, the fifth array of the at least 5 planar microcoil arrays is positioned adjacent a occipital lobe of the brain within the human head. The controller may be adapted to generate an electrical pulse train having a frequency in a range of 1 Hz to 100 Hz and to sequentially deliver the electrical pulse train to each of the at least 5 planar microcoil arrays. The controller may be adapted to generate an electrical pulse train having a frequency in a range of 1 Hz to 100 Hz and to concurrently deliver the electrical pulse train to at least 2 of each of the at least 5 planar microcoil arrays.

Optionally, the hat comprises two or more layers of material and the plurality of planar microcoil arrays is positioned between the two or more layers of material.

Optionally, the controller is adapted to generate an electrical pulse train having a frequency and to deliver the electrical pulse train to each array of the plurality of planar microcoil arrays, wherein the electrical pulse train comprises a first pulse having a first amplitude, a second pulse having a second amplitude, and a third pulse having a third amplitude, wherein the first amplitude is less than the second amplitude and the second amplitude is less than the third amplitude. Each of the first pulse, second pulse, and third pulse may have a substantially rectangular shape. Optionally, upon receiving the electrical pulse train, each array of the plurality of planar microcoil arrays is configured to generate a magnetic field in a range of 100 microTesla to 300 microTesla as measured 1 mm or less from a surface of the each array of the plurality of planar microcoils arrays. The generated magnetic field may be adapted to degrade in air to less than 80 microTesla over a distance of at least 10 mm.

Optionally, each array of the plurality of planar microcoil arrays comprises an input terminal configured to receive current from the controller, an output terminal, and at least two traces to electrically connect each of the microcoils positioned on each array of the plurality of planar microcoil arrays to the input terminal and the output terminal. A first set of each of the microcoils may be configured to direct current clockwise and a second set of each of the microcoils may be configured to direct current counterclockwise. Each of the microcoils may be configured to direct current in a same direction. Each of the microcoils may be at least one of a spiral circular planar microcoil, a rectangular circular planar microcoil, a non-spiral circular planar microcoil, or a non-spiral rectangular planar microcoil.

Optionally, the pulsed electromagnetic field device further comprises a set of programmatic instructions stored on a separate computing device, wherein, when executed by the separate computing device, the programmatic instructions generate a display for prompting a user to input data indicative of a physiological state, wherein the physiological state is representative of at least one of the user's state of stress, state of anxiety, state of relaxation or whether the user has a headache.

Optionally, the controller is adapted to generate an electrical pulse train having a frequency, to deliver the electrical pulse train to each array of the plurality of planar microcoil arrays in accordance with a programmed time period, and to automatically terminate generating the electrical pulse train after the programmed time period elapses.

Optionally, the pulsed electromagnetic field device further comprises a liner configured to be attached to the internal surface of the crown, wherein the liner comprises a plurality of cells and wherein each cell of the plurality of cells is defined by a pocket made of a first material bounded by a second material, and wherein the first material is more flexible than the second material. The plurality of cells may be divided into a first set of cells and a second set of cells, wherein each cell of the first set of cells comprises one array of the plurality of planar microcoils arrays and a cushioning material, and wherein each cell of the second set of cells comprises cushioning material without any array of the plurality of planar microcoils arrays.

Optionally, the substrate is flexible and each of the at least one planar microcoil is embedded, layered, or printed on the flexible substrate.

Optionally, the hat further comprises a brim attached to the crown and the controller is adapted to be coupled to a portion of the brim.

Optionally, the pulsed electromagnetic field device further comprises a set of programmatic instructions stored on a separate computing device, wherein, when executed by the separate computing device, the programmatic instructions generate a display for prompting a user to input data indicative of a desired type of treatment, wherein the desired type of treatment includes at least one of relaxation, improved sleep or sleep assist (which assists a user in falling asleep), mediation assist (which assists a user into getting into a meditative state), improved memory, or improved mental acuity. The controller may be adapted to receive the data indicative of the desired type of treatment from the separate computing device, to generate an electrical pulse train having a frequency based on the data indicative of the desired type of treatment, to deliver the generated electrical pulse train to each array of the plurality of planar microcoil arrays, and to automatically terminate generating the electrical pulse train after a programmed time period elapses. The programmed time period may be based on the data indicative of the desired type of treatment.

Optionally, the controller comprises a switch, wherein a position of the switch is representative of a desired type of treatment, wherein the desired type of treatment includes at least one of relaxation, improved sleep or sleep assist (which assists a user in falling asleep), mediation assist (which assists a user into getting into a meditative state), improved memory, or improved mental acuity, and wherein the controller is adapted to generate an electrical pulse train having a frequency based on the position of the switch, to deliver the generated electrical pulse train to each array of the plurality of planar microcoil arrays, and to automatically terminate generating the electrical pulse train after a programmed time period elapses.

The present specification also discloses a pulsed electromagnetic field device comprising: an article of clothing; a controller removably attachable to the article of clothing; and a plurality of planar microcoil arrays, wherein each of the plurality of planar microcoil arrays comprises two or more planar microcoils positioned on a flexible substrate, wherein each of the plurality of planar microcoil arrays is integrated into the article of clothing; and wherein each of the plurality of planar microcoil arrays is in electrical communication with the controller.

Optionally, the pulsed electromagnetic field device further comprises a docking station, wherein the docking station is configured to releasably receive the controller. Optionally, the docking station comprises a first mechanical connector and a first electrical interface, wherein the controller comprises a second mechanical connector and a second electrical interface, and wherein, upon the first mechanical connector and the second mechanical connector latching, the first electrical interface is automatically placed in electrical communication with the second electrical interface.

Optionally, the article of clothing comprises two or more layers of material and the plurality of planar microcoil arrays is positioned between the two or more layers of material.

Optionally, the article of clothing is at least one of a sock, a shoe, a shirt, a pant, a glove, a mask, a neck covering, a head covering, a headband, a sleeve, or a brace configured to fit over an elbow, an ankle, or a knee.

Optionally, the controller is configured to generate a pulse train, wherein each pulse train comprises a plurality of pulses having an amplitude in a range of 1 mA to 200 mA. Optionally, the pulse train comprises a first pulse having a first amplitude, a second pulse having a second amplitude, and a third pulse having a third amplitude, wherein the first amplitude is less than the second amplitude and the second amplitude is less than the third amplitude. Each of the first pulse, second pulse, and third pulse may have a square shape. Each of the two or more planar microcoils may be configured to generate a magnetic field in a range of 1 microTesla to 100 microTesla upon receiving the pulse train.

Optionally, each of the plurality of planar microcoil arrays comprises at least six planar microcoils. Each of the plurality of planar microcoil arrays may comprise an input terminal configured to receive current from the controller, an output terminal, and at least two traces to electrically connect each of the at least six planar microcoils to the input terminal and the output terminal. Optionally, a first set of the at least six planar microcoils is configured to direct current clockwise and a second set of the at least six planar microcoils is configured to direct current counterclockwise. Optionally, the first set of the at least six planar microcoils is less than the second set of the at least six planar microcoils. Optionally, the first set of the at least six planar microcoils is equal to the second set of the at least six planar microcoils. All of the at least six planar microcoils may be configured to direct current in a same direction.

Optionally, each of the two or more planar microcoils is at least one of a spiral circular planar microcoil, a rectangular circular planar microcoil, a non-spiral circular planar microcoil, or a non-spiral rectangular planar microcoil.

Optionally, each of the plurality of planar microcoil arrays is physically separate and a first subset of the plurality of planar microcoil arrays has a different surface area than a second subset of the plurality of planar microcoil arrays.

Optionally, each of the plurality of planar microcoil arrays is physically separate and has a same surface area.

The controller may be configured to generate a time varying current in order to create a time varying magnetic field at each of the plurality of planar microcoil arrays. Optionally, the time varying current is defined by square waves having substantially equal peak amplitude values. Optionally, the time varying current is defined by sinusoidal waves having substantially equal peak amplitude values. Optionally, the time varying current is defined by square waves having substantially different peak amplitude values. Optionally, the time varying current is defined by a train of square waves wherein, in each train, the square waves have peak values that ramp from a low peak amplitude value to a higher peak amplitude value.

The controller may be configured to cause an electrical current to be concurrently transmitted to all of the plurality of planar microcoil arrays.

The controller may be configured to cause an electrical current to be transmitted to all of the plurality of planar microcoil arrays at different times.

Optionally, the pulsed electromagnetic field device further comprises a set of programmatic instructions stored on a separate computing device, wherein, when executed by the separate computing device, the programmatic instructions generate a display for prompting a user to input a pain level and a locus of pain. Optionally, when executed by the separate computing device, the programmatic instructions determine which of the plurality of planar microcoil arrays should receive an electrical current based on at least one of the pain level or the locus of pain. Optionally, when executed by the separate computing device, the programmatic instructions generate data indicative of which of the plurality of planar microcoil arrays should receive an electrical current based on at least one of the pain level or the locus of pain and transmit the data to the controller. Optionally, the controller generates an electrical current based on the data and in a predefined pattern based on at least one of the pain level or the locus of pain.

Optionally, the pulsed electromagnetic field device further comprises a plurality of traces integrated into the article of clothing and extending from each of the plurality of planar microcoil arrays to the controller.

The present specification also discloses a method of treating a condition, comprising: attaching an article of clothing to a portion of a patient's body, wherein the article of clothing comprises a plurality of planar microcoil arrays, wherein each of the plurality of planar microcoil arrays comprises two or more planar microcoils positioned on a flexible substrate, wherein each of the plurality of planar microcoil arrays is integrated into the article of clothing; and wherein each of the plurality of planar microcoil arrays is in electrical communication with a docking station integrated into the article of clothing; attaching a controller to the docking station, wherein the controller comprises a circuit and a power source; and activating the controller to cause a time varying current to be transmitted to each of the plurality of planar microcoil arrays.

The method condition may be at least one of an anxiety disorder, an obsessive compulsive disorder, a post-traumatic stress disorder, memory degeneration, schizophrenia, Parkinson's disease, stroke rehabilitation, drug addiction, drug cravings, depression, depression-related conditions, postpartum depression, bipolar depression, auditory hallucinations, multiple sclerosis, fibromyalgia, Alzheimer's disease, spinocerebellar degeneration, epilepsy, urinary incontinence, movement disorders, chronic tinnitus, or sleep apnea.

Optionally, the method further comprises attaching the article of clothing such that at least one of the two or more planar microcoils in at least one of the plurality of planar microcoil arrays is positioned over an acupoint of the patient's body.

Optionally, upon attaching the controller to the docking station, the circuit automatically electrically interfaces with at least one of the plurality of planar microcoil arrays.

The present specification also discloses a pulsed electromagnetic field system comprising: a plurality of planar microcoil arrays, wherein each of the plurality of planar microcoil arrays comprises two or more planar microcoils positioned on a flexible substrate and wherein one of the plurality of planar microcoil arrays is connected to another of the plurality of planar microcoil arrays; and a controller configured to generate an electrical current and transmit that electrical current, in accordance with a particular stimulation protocol, to each of the plurality of planar microcoil arrays.

Optionally, the planar microcoil is at least one of a spiral circular planar microcoil, a rectangular circular planar microcoil, a non-spiral circular planar microcoil, or a non-spiral rectangular planar microcoil.

Optionally, a first subset of the plurality of planar microcoil arrays has a different surface area than a second subset of the plurality of planar microcoil arrays.

Optionally, each of the plurality of planar microcoil arrays has a same surface area.

Optionally, the stimulation protocol comprises a time varying magnetic field. Optionally, the time varying magnetic field is defined by square waves having substantially equal peak values. Optionally, the time varying magnetic field is defined by a sinusoidal wave. Optionally, the time varying magnetic field is defined by square waves having different peak values. Optionally, the time varying magnetic field is defined by a train of square waves wherein, in each train, the square waves have peak values that ramp from a low peak value to a higher peak value.

Optionally, the controller is configured to cause an electrical current to be transmitted substantially currently to all of the plurality of planar microcoil arrays.

Optionally, the controller is configured to cause an electrical current to be transmitted to the plurality of planar microcoil arrays at different times.

Optionally, the pulsed electromagnetic field system further comprises a set of programmatic instructions stored on a separate computing device, wherein, when executed by the separate computing device, the programmatic instructions generate a display for prompting a user to input a pain level and a locus of pain. Optionally, when executed by the separate computing device, the programmatic instructions determine which of the plurality of planar microcoil arrays should receive an electrical current based on the pain level and/or locus of pain. Optionally, when executed by the separate computing device, the programmatic instructions generate data indicative of which of the plurality of planar microcoil arrays should receive an electrical current based on the pain level and/or locus of pain and transmit said data to the controller. Optionally, the controller generates an electrical current based on said data and in a predefined pattern based on the pain level and/or locus of pain.

The present specification also discloses a sock, shirt, pant, glove, head covering, head band, helmet, mask, neck covering, sleeve, and garment comprising the pulsed electromagnetic field system described above.

The present specification also describes a repetitive transcranial magnetic stimulation system for detecting and suppressing epileptic seizures comprising a hat comprising a crown having an internal surface configured to receive a human head, a controller configured to be attached to an external surface of the hat, electroencephalogram (EEG) sensors distributed around, and coupled to the internal surface, and a plurality of planar microcoil arrays, wherein each array of the plurality of planar microcoil arrays comprises at least one planar microcoil positioned on a substrate, wherein each array of the plurality of planar microcoil arrays is coupled to the internal surface of the crown in positions where the EEG sensors are not located, and wherein each array of the plurality of planar microcoil arrays is in electrical communication with the controller, wherein the controller is configured to receive data from the EEG sensors, determine if a seizure is occurring or is imminent based on the EEG sensor data, and based on said determination, direct current to at least one of the plurality of planar microcoil arrays.

Optionally, each array of the plurality of planar microcoil arrays is physically separate and configured to independently receive an electrical current from the controller. Optionally, the controller is adapted to generate an electrical pulse train having a frequency and to deliver the electrical pulse train to each array of the plurality of planar microcoil arrays. Optionally, the electrical pulse train comprises at least two pulses having different peak levels of current and wherein the different peak levels of current are in a range of 5 mA to 500 mA. Optionally, the shape of each of the at least two pulses is rectangular. Optionally, the frequency is in a range of 0.1 Hz to 5 Hz. Optionally, each array of the plurality of planar microcoil arrays comprises at least 4 spiral-shaped microcoils. Optionally, the controller is adapted to generate an electrical pulse train that is currently delivered to each of the at least 4 microcoils concurrently. Optionally, the controller is adapted to generate an electrical pulse train having a frequency in a range of 0.1 Hz to 5 Hz and to sequentially deliver the electrical pulse train to each of the at least 5 planar microcoil arrays. Optionally, the controller is adapted to generate an electrical pulse train having a frequency in a range of 0.1 Hz to 5 Hz and to concurrently deliver the electrical pulse train to at least 2 of each of the at least 5 planar microcoil arrays. Optionally, the hat comprises two or more layers of material and wherein the plurality of planar microcoil arrays and EEG sensors are positioned between the two or more layers of material. Optionally, the controller is adapted to generate an electrical pulse train having a frequency and to deliver the electrical pulse train to each array of the plurality of planar microcoil arrays, wherein the electrical pulse train comprises a first pulse having a first amplitude, a second pulse having a second amplitude, and a third pulse having a third amplitude, wherein the first amplitude is less than the second amplitude and the second amplitude is less than the third amplitude. Optionally, each of the first pulse, second pulse, and third pulse has a substantially rectangular shape.

In another embodiment, the present specification discloses a method of increasing cerebral oxygenation levels in a person undergoing cardiac arrest, comprising: acquiring a disposable repetitive transcranial magnetic stimulation system for detecting and suppressing epileptic seizures comprising a cap that has a crown having an internal surface configured to receive a human head, a controller configured to be attached to an external surface of the cap, and a plurality of planar microcoil arrays, wherein each array of the plurality of planar microcoil arrays comprises at least one planar microcoil positioned on a substrate, wherein each array of the plurality of planar microcoil arrays is coupled to the internal surface of the crown, and wherein each array of the plurality of planar microcoil arrays is in electrical communication with the controller, and activating the controller to initiate current to one or more of the plurality of planar microcoil arrays.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings:

FIG. 30 shows a process for automatically detecting and treating an epileptic seizure;

DETAILED DESCRIPTION

Figure 1B:
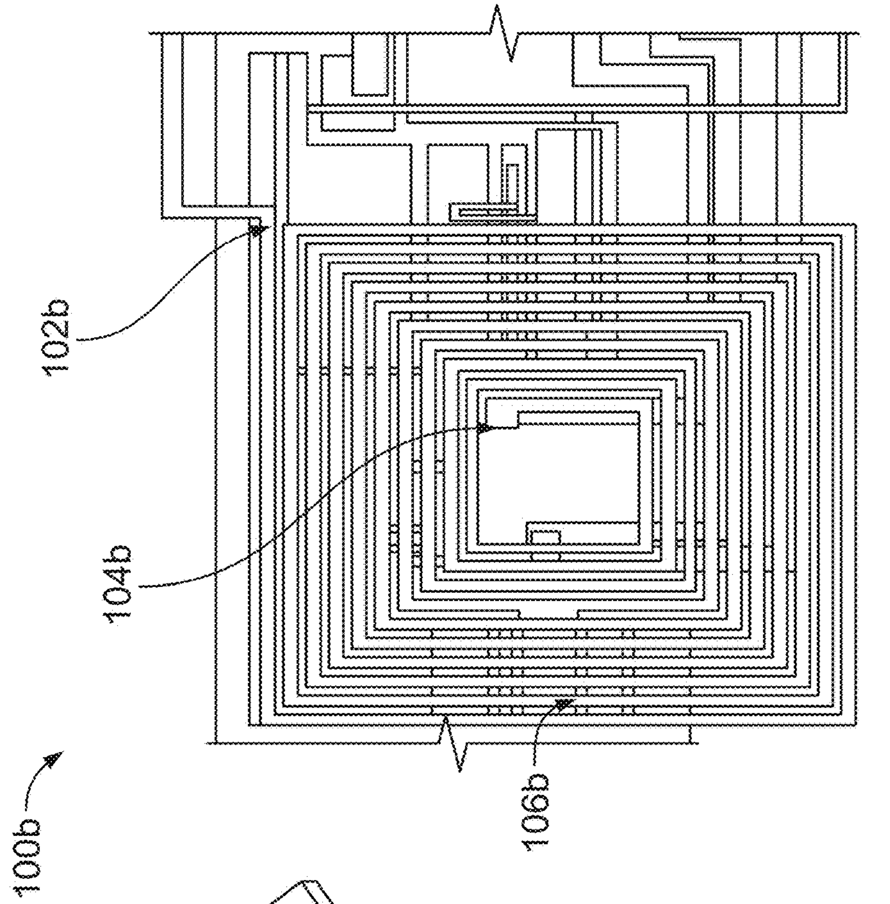
FIG. 1B depicts an exemplary planar microcoil in a first rectangular configuration.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

As used herein, the term "planar coil" or "planar microcoil" both refer to a conductive pathway with curves or turns where the entirety of the conductive pathway is substantially positioned within the same plane. Stated differently, the turns, curves, or coils of the conductive pathway occupy varied positions within an X-Y plane but are of the same thickness or have a thickness within a range of 20% of each other. Accordingly, such a planar microcoil is differentiated from conventional coil structures because the windings or turns of the coil do not extend substantially upward or outward from the innermost or first coil in the Z direction or normal to the X-Y plane defined by the innermost or first coil. The terms "extend substantially upward or outward", "within the same plane", or "within the same X-Y plane" are defined as within +/−20 mm, within +/−15 mm, within +/−10 mm, or more preferably within +/−5 mm of a 0 point on the Z axis and therefore includes a coil that winds upwards through layers of a thin flexible substrate, where the thickness of the thin flexible substate is less than 20 mm, less than 15 mm, less than 10 mm, or preferably less than 5 mm. The planar footprint area of a "planar coil" or "planar microcoil" is preferably greater than 1 $cm^2$, more preferably between 1 $cm^2$ and 9 $cm^2$, and even more preferably between 2 $cm^2$ and 4 $cm^2$.

As used herein, the term "magnetic flux" refers to a quantity or strength of magnetic lines produced by a current passing through one or more planar coils and the term "magnetic flux density" refers to the amount of that magnetic flux in an area taken perpendicular to the magnetic flux's direction, typically measured in Tesla. It should be appreciated that, throughout this specification and in each embodiment taught here, all magnetic fields, and corresponding magnetic flux and magnetic flux densities, are generated by a current passing through one or more planar coils and are not generated by one or more permanent magnets unless otherwise stated. It should further be appreciated that each embodiment described herein may further include an optional version which expressly does not include, incorporate, or otherwise use permanent magnets but, yet, which still generate magnetic fields.

Planar Microcoil Structure

Figure 1A:
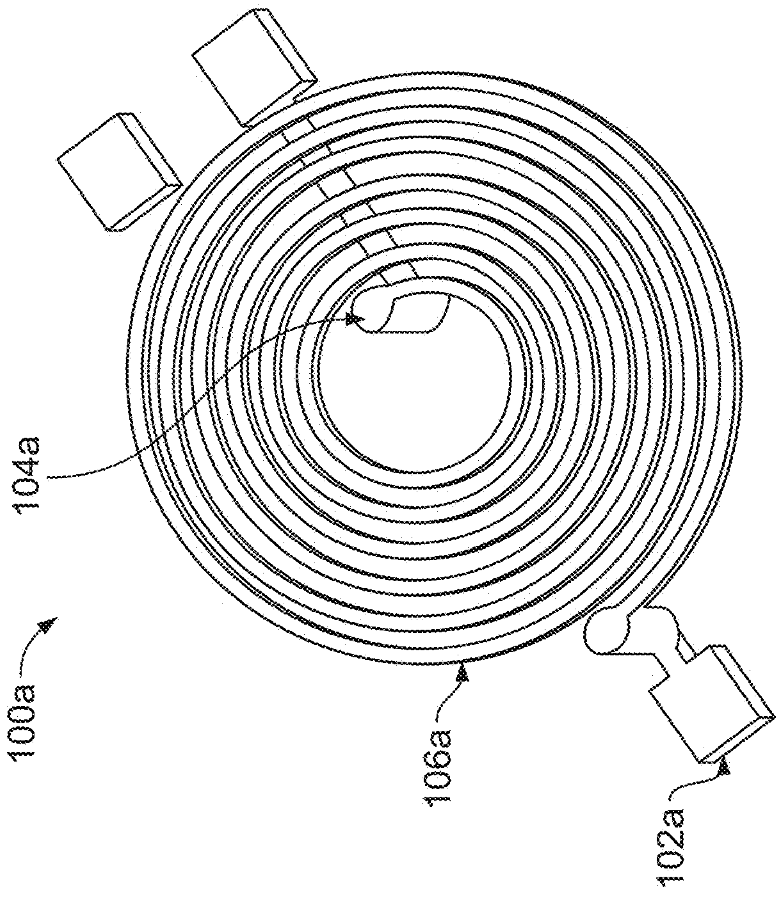
FIG. 1A depicts an exemplary planar microcoil in a first circular configuration.

Referring to FIGS. 1A, 1B, 2A, and 2B, the planar microcoils may have a plurality of different shapes and dimensions. FIG. 1A shows a spiral circular planar microcoil 100*a* having six turns where the conductive pathway follows a spiral shape from a first part of the circuit 102*a*, or where the spiral coil conductive pathway begins, to a second part of the circuit 104*a*, or where the spiral coil conductive pathway terminates. Each turn forms a circle, except that the beginning and end of the circle are offset from each other, thereby creating a spiral across all turns. The spiral shaped conductive pathway 106*a* is substantially entirely positioned within the same X-Y plane.

Similarly, FIG. 1B shows a spiral rectangular planar microcoil 100*b* having 10 turns where the conductive pathway follows a spiral shape from a first part of the circuit 102*b*, or where the spiral coil conductive pathway begins, to a second part of the circuit 104*b*, or where the spiral coil conductive pathway terminates. Each turn forms a rectangle, except that the beginning and end of the circle are offset from each other, thereby creating a spiral across all turns. The spiral shaped conductive pathway 106*b* is substantially entirely positioned within the same X-Y plane.

It should be appreciated that the present invention is directed toward any spiral shaped planar microcoil, including polygonal, elliptical, or other shapes, having a plurality of turns where the conductive pathway follows a spiral shape from a first part of the circuit, or where the spiral coil conductive pathway begins, to a second part of the circuit, or where the spiral coil conductive pathway terminates. In such embodiments, each turn would form the same polygonal, elliptical, or other shape, except that the beginning and end of the shape are offset from each other, thereby creating a spiral across all turns. The spiral shaped conductive pathway would also be substantially entirely positioned within the same X-Y plane.

Figure 2B:
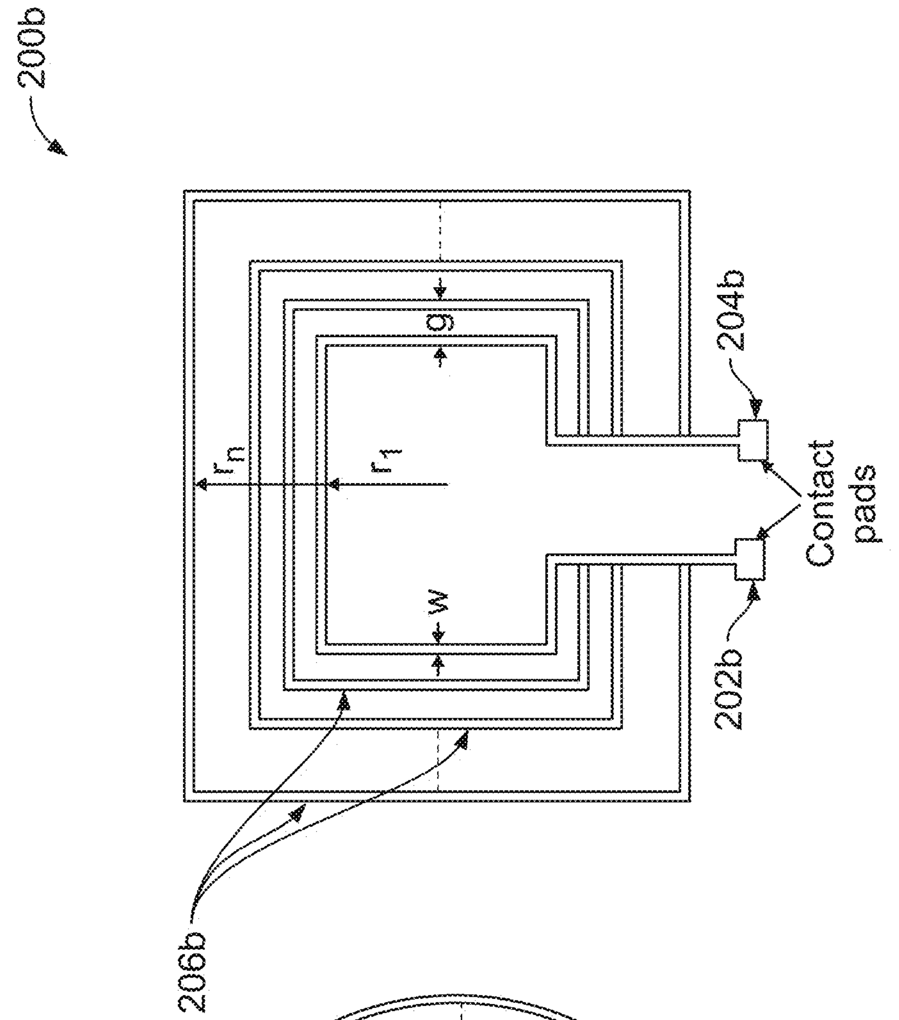
FIG. 2B depicts an exemplary planar microcoil in a second rectangular configuration.
Figure 2A:
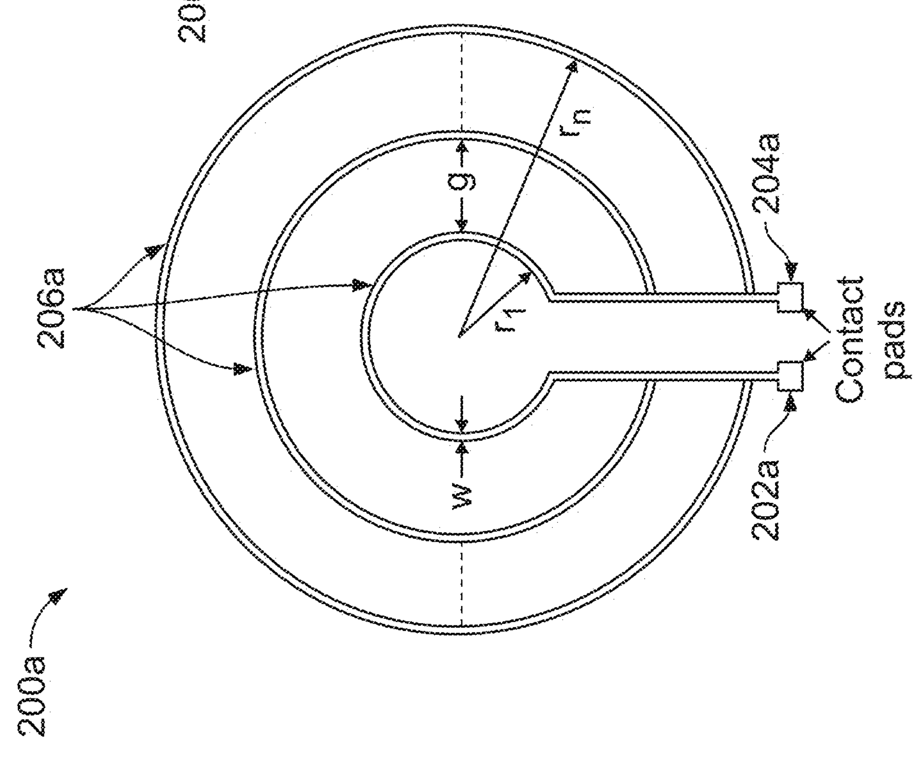
FIG. 2A depicts an exemplary planar microcoil in a second circular configuration.

FIG. 2A shows a non-spiral circular planar microcoil 200*a* having three turns where the conductive pathway follows a curved, or circular, shape from a first part of the circuit 202*a*, or where the coil conductive pathway begins, to a second part of the circuit 204*a*, or where the coil conductive pathway terminates. Each turn forms an incomplete circle and shares a common electrical input and electrical output with the adjacent turns, thereby creating a set of nested incomplete circles, each in electrical communication with a common electrical input 202*a* and electrical output 204*a* and each having a progressively smaller (or larger) radius. The conductive pathway of nested incomplete circles 206*a* is substantially entirely positioned within the same X-Y plane.

Similarly, FIG. 2B shows a non-spiral rectangular planar microcoil 200*b* having four turns where the conductive pathway follows a polygonal, or rectangular, shape from a first part of the circuit 202*b*, or where the coil conductive pathway begins, to a second part of the circuit 204*b*, or where the coil conductive pathway terminates. Each turn forms an incomplete rectangle and shares a common electrical input and electrical output with the adjacent turns, thereby creating a set of nested incomplete rectangles, each in electrical communication with a common electrical input 202*b* and electrical output 204*b* and each having a progressively smaller (or larger) length and width. The conductive pathway of nested incomplete rectangles 206*b* is substantially entirely positioned within the same X-Y plane.

Figure 3A:
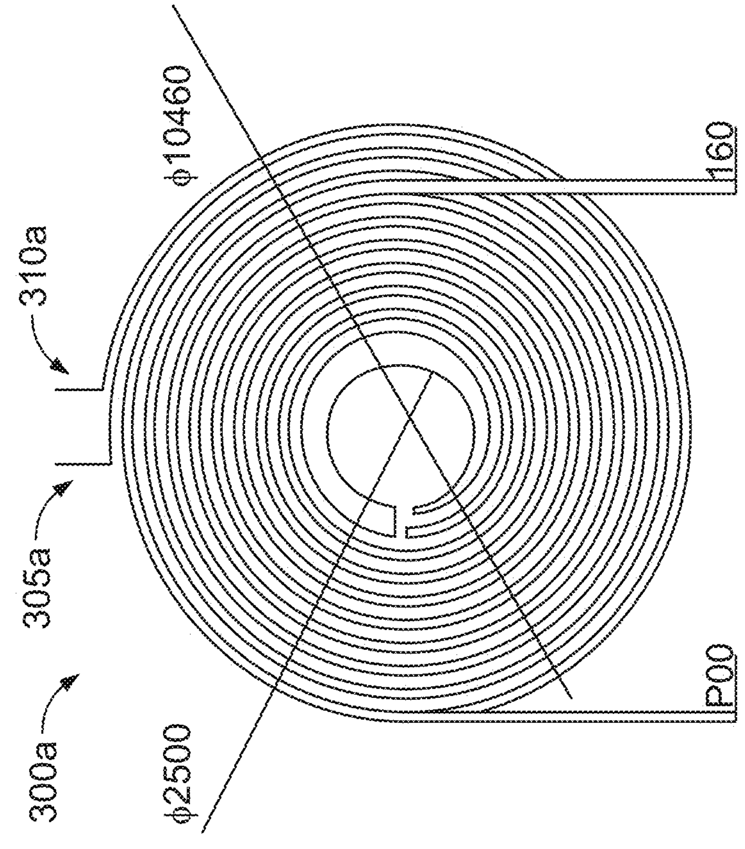
FIG. 3A depicts an exemplary planar microcoil in a third circular configuration.
Figure 3B:
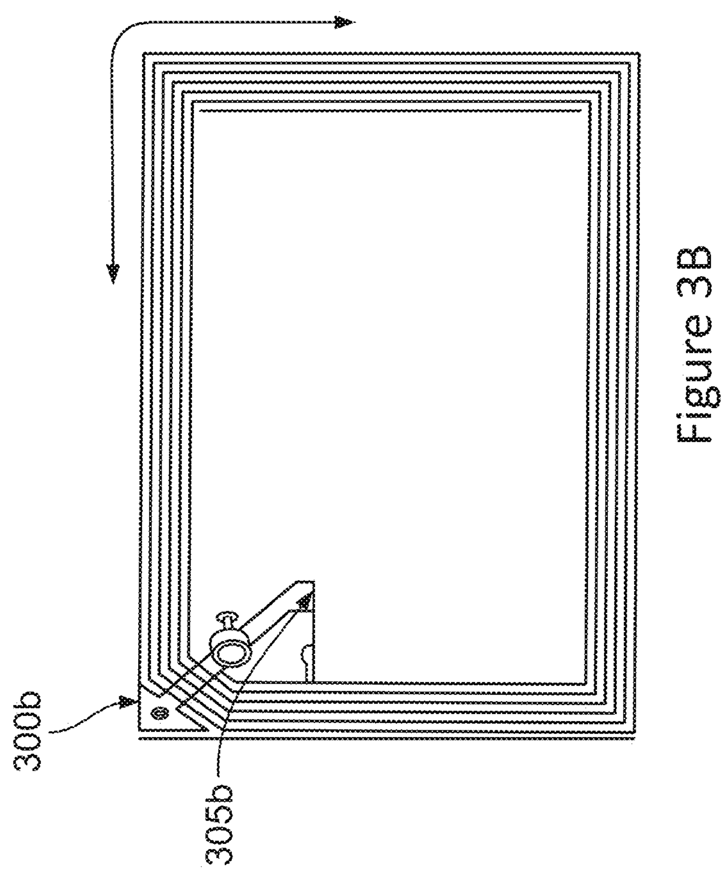
FIG. 3B depicts an exemplary planar microcoil in a third rectangular configuration.
Figure 3C:
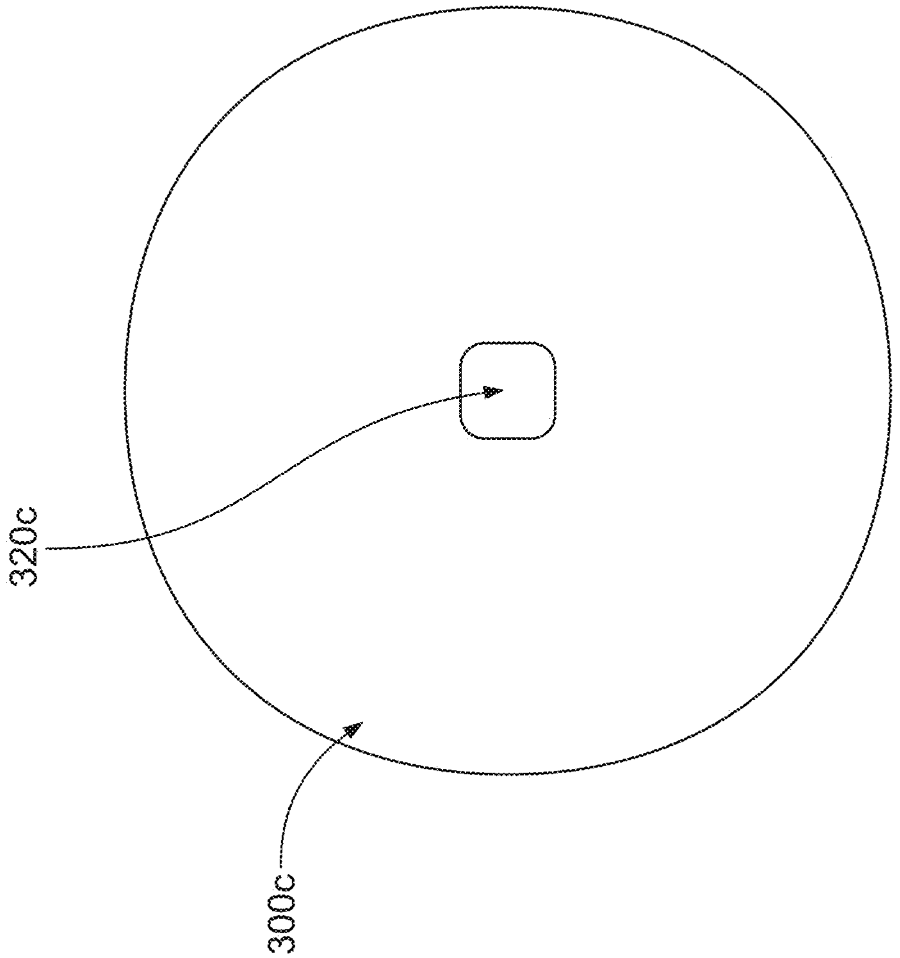
FIG. 3C depicts an exemplary planar microcoil in a fourth configuration.
Figures 4A, 4B, 4C:
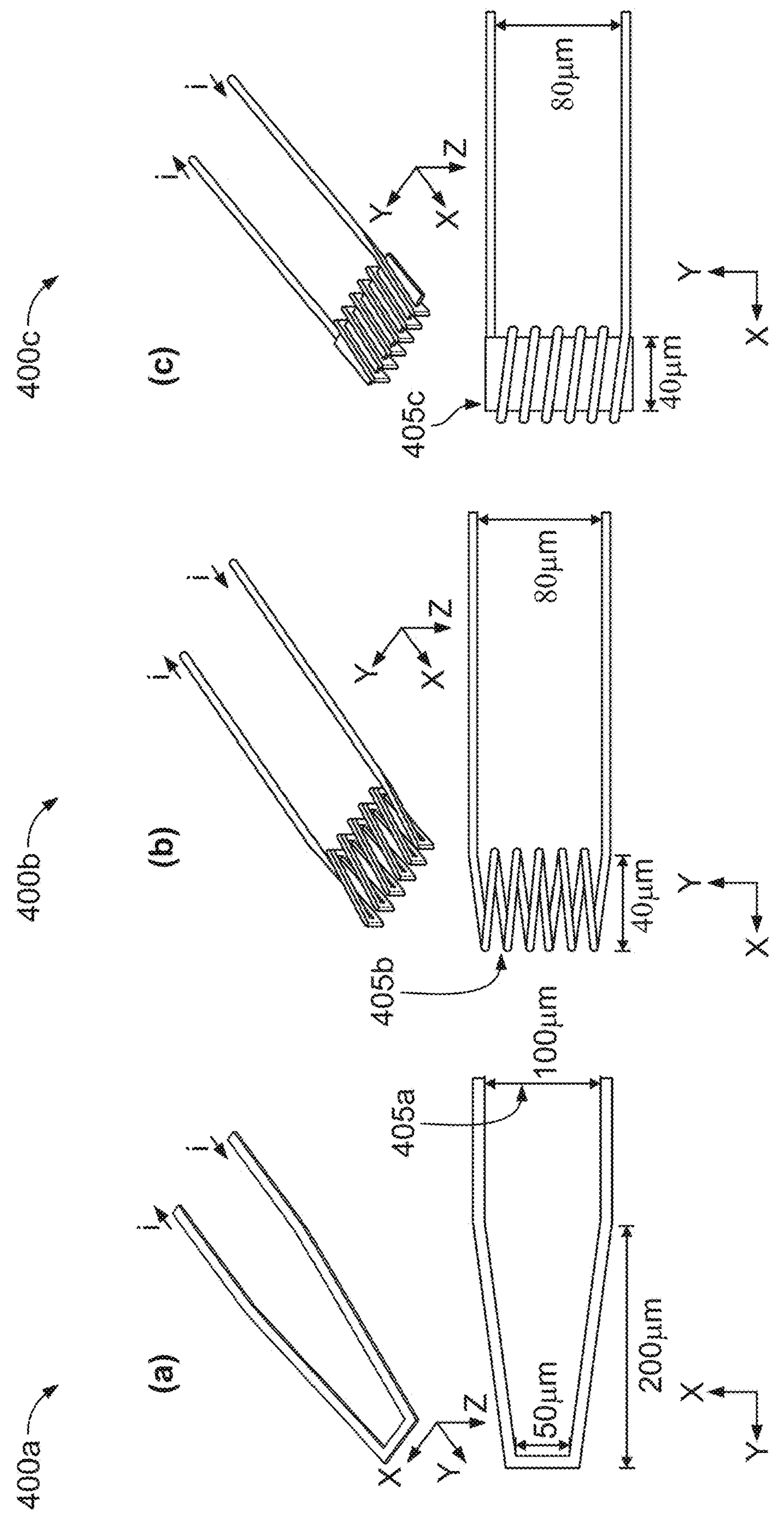
FIG. 4A depicts an exemplary planar microcoil in a first alternative configuration.
FIG. 4B depicts an exemplary planar microcoil in a second alternative configuration.
FIG. 4C depicts an exemplary planar microcoil in a third alternative configuration.
Figure 7B:
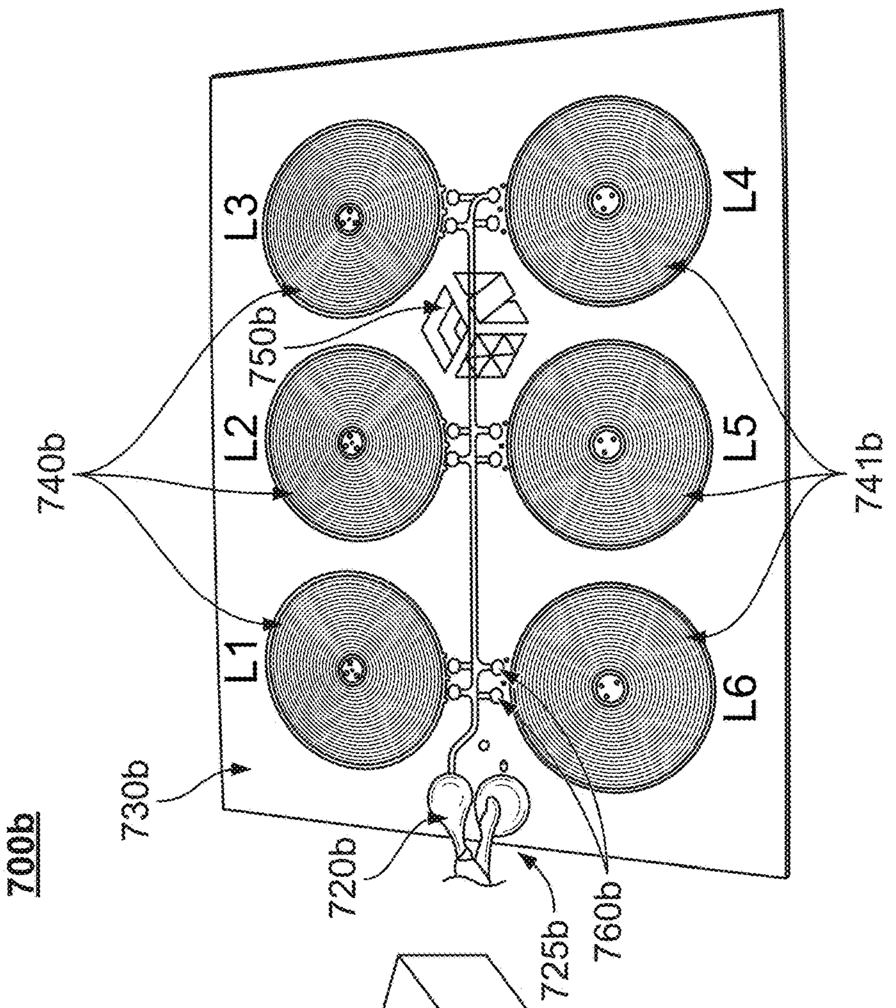
FIG. 7B depicts an exemplary set of planar microcoils positioned on a substrate.
Figure 7A:
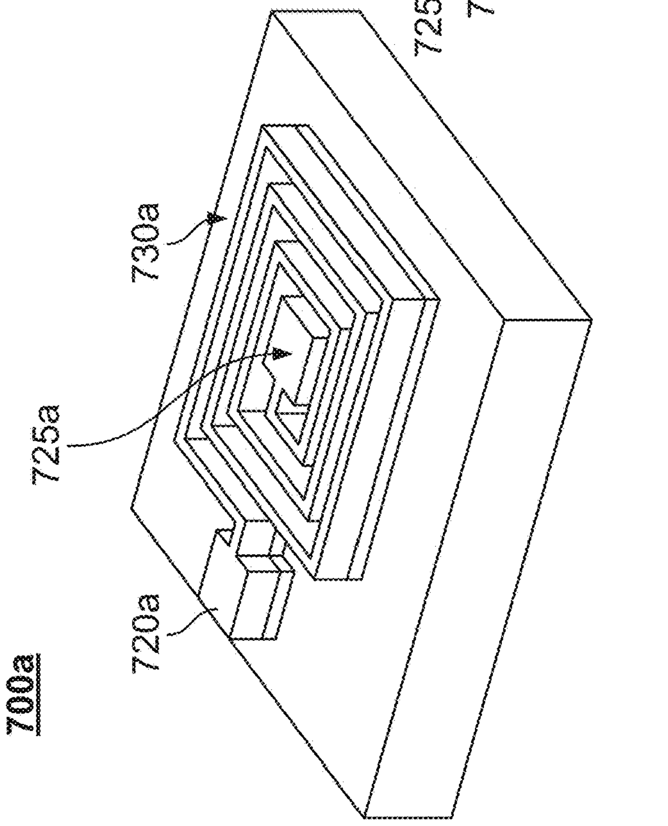
FIG. 7A depicts an exemplary planar microcoil positioned on a substrate.
Figure 8:
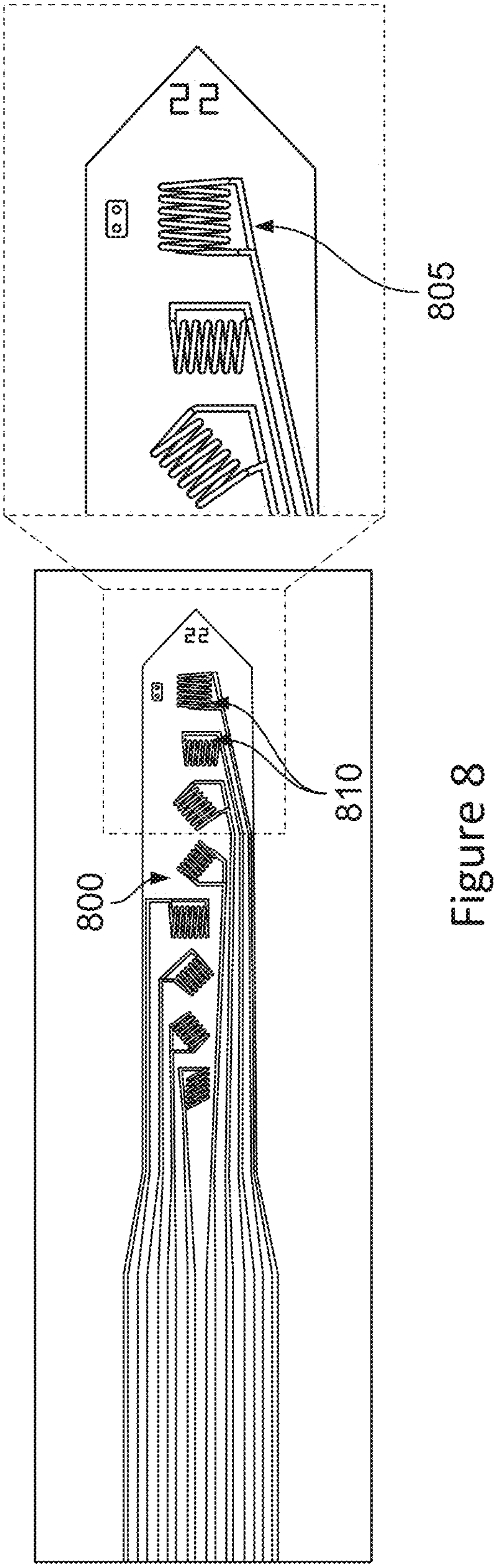
FIG. 8 depicts exemplary planar microcoils positioned on a second substrate.

It should be appreciated that the present invention is directed toward any non-spiral shaped planar microcoil, including polygonal, elliptical, or other shapes, having a plurality of turns where the conductive pathway follows a polygonal, elliptical, or other shape from a first part of the circuit, or where the coil conductive pathway begins, to a second part of the circuit, or where the coil conductive pathway terminates. In such embodiments, each turn would form the same incomplete polygonal, elliptical, or other shape and would share a common electrical input and electrical output with the adjacent turns, thereby creating a set of nested incomplete polygonal, elliptical, or other shapes, each in electrical communication with a common electrical input and electrical output and each having a progressively smaller (or larger) length and width or radius. The conductive pathway of nested incomplete polygonal, elliptical, or other shapes would be substantially entirely positioned within the same X-Y plane FIGS. 3A, 3B, 3C, 4A, 4B, 4C, 5A, 5B, 7A, 7B and 8 show additional exemplary microcoil embodiments and configurations. Referring to FIG. 3A, a circular spiral coil is shown 300*a* with a current input 305*a* and current output 310*a* on the same side and parallel to each other. FIG. 3B shows a rectangular spiral coil 300*b* with a current input or output 305*b* in the interior of the coil 300*b*. FIG. 3C shows a high-density spiral coil with an interior, wireless region 320*c* that is rectangular with curved corners. FIGS. 4A-4C show less preferred embodiments where 400*a* shows a two pronged coil with the two parallel ends of the coil separated by an open space 405*a*, 400*b* shows a two pronged coil with the two parallel ends of the coil separated by a zig-zag coil 405*b*, and 400*c* shows a two pronged coil with the two parallel ends of the coil separated by a zig-zag coil and having a conductive material positioned therein 405*c*. Referring to FIG. 8, a multi-coil planar array 800 may include two or more pronged coils 810 with the two ends of the coil separated by a zig-zag coil 805.

Figure 5B:
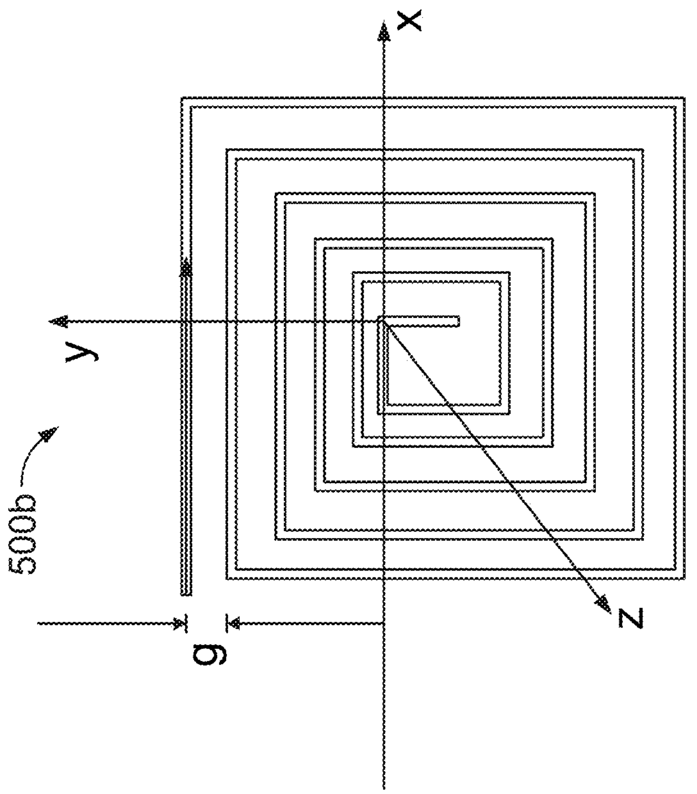
FIG. 5B depicts a second exemplary set of dimensions associated with an exemplary rectangular planar microcoil.
Figure 5A:
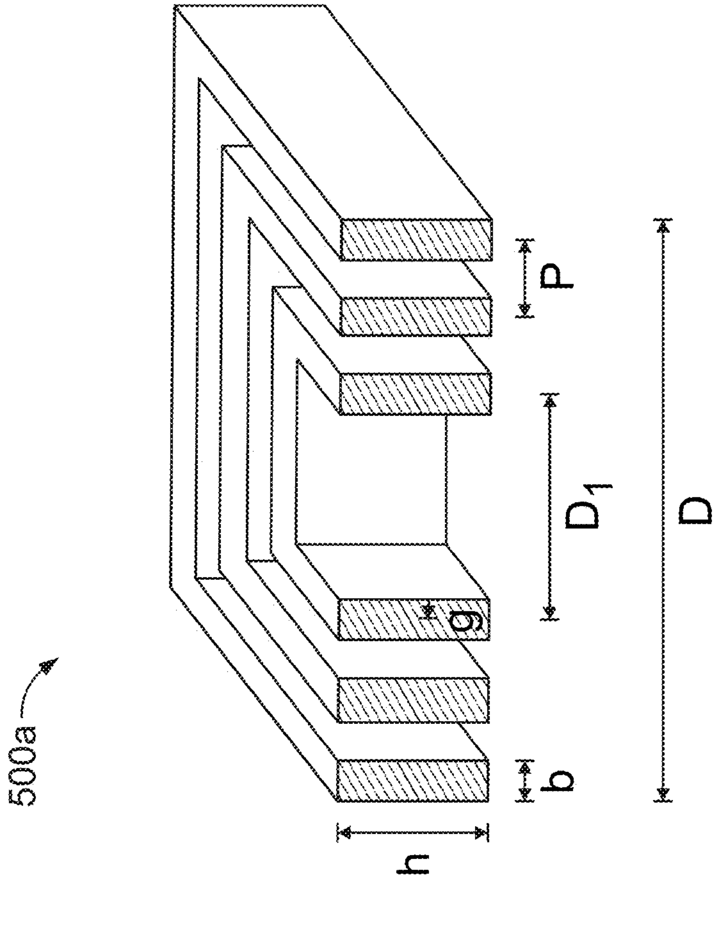
FIG. 5A depicts a first exemplary set of dimensions associated with an exemplary rectangular planar microcoil.

FIG. 5A shows a side perspective view of a planar coil 500*a* with coil depth in the Z the direction, as denoted by the variable "h". The variable D denotes a dimension indicative of the distance from one exterior side of the coil to the opposing exterior side of the coil. The variable b denotes a dimension indicative of the thickness of the coil. The variable p denotes a dimension indicative of the distance between coils, referred to as a pitch. The variable Di denotes a dimension indicative of the distance from one interior side of the innermost coil to the opposing interior side of the innermost coil. Referring to FIG. 5B, the variable g also shows a spacing between coils. The arrow indicates a flow of current from an outside current coil connection to an inside current coil output. Referring to FIG. 7A, a single coil 700*a* mounted on a substrate 730*a*, where the coil is rectangular and has an input/output, 720*a*, 725*a*, on the exterior of the coil and in the interior of the coil. Referring to FIG. 7B, six coil 700*a* mounted on a substrate 730*a*, where the coil is rectangular and has an input/output, 720*a*, 725*a*, on the exterior of the coil and in the interior of the coil. FIG. 7B represents the preferred embodiment of a planar multi-coil array 700*b* and is discussed in greater detail with respect to FIG. 15. Six circular planar coils, 740*b*, 741*b*, are mounted on a flexible substrate 730*b*. Three coils 740*b* are on a top side and three coils 741*b* are on a bottom side. All coils are electrically connected, via traces 750*b* which run across the substrate, and 760*b* which connect from trace 750*b* to an individual coil, to a current input 720*b* and a current output 725*b*. In one embodiment, the current input 720*b* and output 725*b* are on the same side of the substrate 730*b*. In another embodiment, the current input 720*b* and output 725*b* may be on the different sides of the substrate 730*b*.

Table 1 has a list of preferred attributes of each of the spiral circular coil (FIG. 1A), spiral rectangular coil (FIG. 1B), non-spiral circular coil (FIG. 2A), and non-spiral rectangular coil (FIG. 2B). It should be appreciated that one or more of the other coils, as described herein, may have one or more of the preferred attributes described in Table 1 below.

TABLE 1

| Coil Attributes | | | | |
|---|---|---|---|---|
| Variables | Spiral circular coil Figure 1A | Spiral rectangular coil Figure 1B | Non-spiral circular coil Figure 2A | Non-spiral rectangular coil Figure 2B |
| Width of the coil segments (note that the widths may be constant or variable) | 1 to 200 microns (preferably 25 to 100 microns, preferably 50 microns) | 1 to 200 microns (preferably 25 to 100 microns, preferably 50 microns) | 1 to 200 microns (preferably 25 to 100 microns, preferably 50 microns) | 1 to 200 microns (preferably 25 to 100 microns, preferably 50 microns) |
| Distance from center of coil to innermost coil segment | 10 to 500 microns (preferably 100 microns) | 10 to 500 microns (preferably 100 microns) | 10 to 500 microns (preferably 100 microns) | 10 to 500 microns (preferably 100 microns) |
| Distance from center to the outermost coil segment | 43 to 800250 microns, where the max distance is calculated using 100 microns for the width of the coil segment, 250 microns for the distance from the center of the coil to the innermost coil segment, pitch is 1500 microns, number of turns is 500 | 43 to 800250 microns, where the max distance is calculated using 100 microns for the width of the coil segment, 250 microns for the distance from the center of the coil to the innermost coil segment, pitch is 1500 microns, number of turns is 500 | 43 to 800250 microns, where the max distance is calculated using 100 microns for the width of the coil segment, 250 microns for the distance from the center of the coil to the innermost coil segment, pitch is 1500 microns, number of turns is 500 | 43 to 800250 microns, where the max distance is calculated using 100 microns for the width of the coil segment, 250 microns for the distance from the center of the coil to the innermost coil segment, pitch is 1500 microns, number of turns is 500 |
| Distance between each coil segment, referred to as pitch (note that the pitch may be constant or variable) | 10 to 3000 microns (preferably 50, 200, 650, 1150 microns) | 10 to 3000 microns (preferably 50, 200, 650, 1150 microns) | 10 to 3000 microns (preferably 50, 200, 650, 1150 microns) | 10 to 3000 microns (preferably 50, 200, 650, 1150 microns) |
| Height of the coil segments | 0.1 to 20 microns (preferably 1 micron) | 0.1 to 20 microns (preferably 1 micron) | 0.1 to 20 microns (preferably 1 micron) | 0.1 to 20 microns (preferably 1 micron) |
| Number of turns (defined as the number of times a coil travels around the center of the coil at least 270 degrees) | 3 to 500 (preferably 5, 20, 48, 94) | 3 to 500 (preferably 5, 20, 48, 94) | 3 to 500 (preferably 5, 20, 48, 94) | 3 to 500 (preferably 5, 20, 48, 94) |
| Support structure | $SiO_2$/Si, wafer, Kapton, flexible | $SiO_2$/Si, wafer, Kapton, flexible | $SiO_2$/Si, wafer, Kapton, flexible | $SiO_2$/Si, wafer, Kapton, flexible |

Referring back to FIG. 3C, in another embodiment, a copper coil 300*c* that is substantially circular with a substantially rectangular inner air core (having rounded internal edges) is provided. In one embodiment, it has the following attributes:

1. The coil, including any hard-plastic backing, has a footprint no greater than 2 cm by 2 cm, preferably no greater than 1.65 by 1.65 centimeters.

2. The coil comprises a plurality of wire turns, where the diameter of the coil in the plane of the coil is 0.04 mm.

3. The coil will have a minimum of 100 turns, preferably 175 windings, and even more preferably greater than 150 windings.

4. Each corner of the coil will have 1 quarter-circle with a radius of 0.18125 cm.

5. The inductance is in a range of 200 to 700 μH, preferably around 373 μH and the resistance is in a range of 50 to 800 ohms, preferably around 144 ohms.

6. The inner air core has dimensions in a range of 0.2 cm by 0.2 cm with each corner of the inner air core being 1 quarter-circle with a radius of 0.00625 cm.

Profile of the Magnetic Field

Referring to FIGS. 22A-22F, preferred planar microcoil arrays preferably generate high intensity, sharply peaking fields at a small vertical distance from the surface of the planar microcoil that rapidly flatten and decrease in intensity as the vertical distance from the surface of the planar microcoil array increases.

Figure 22A:
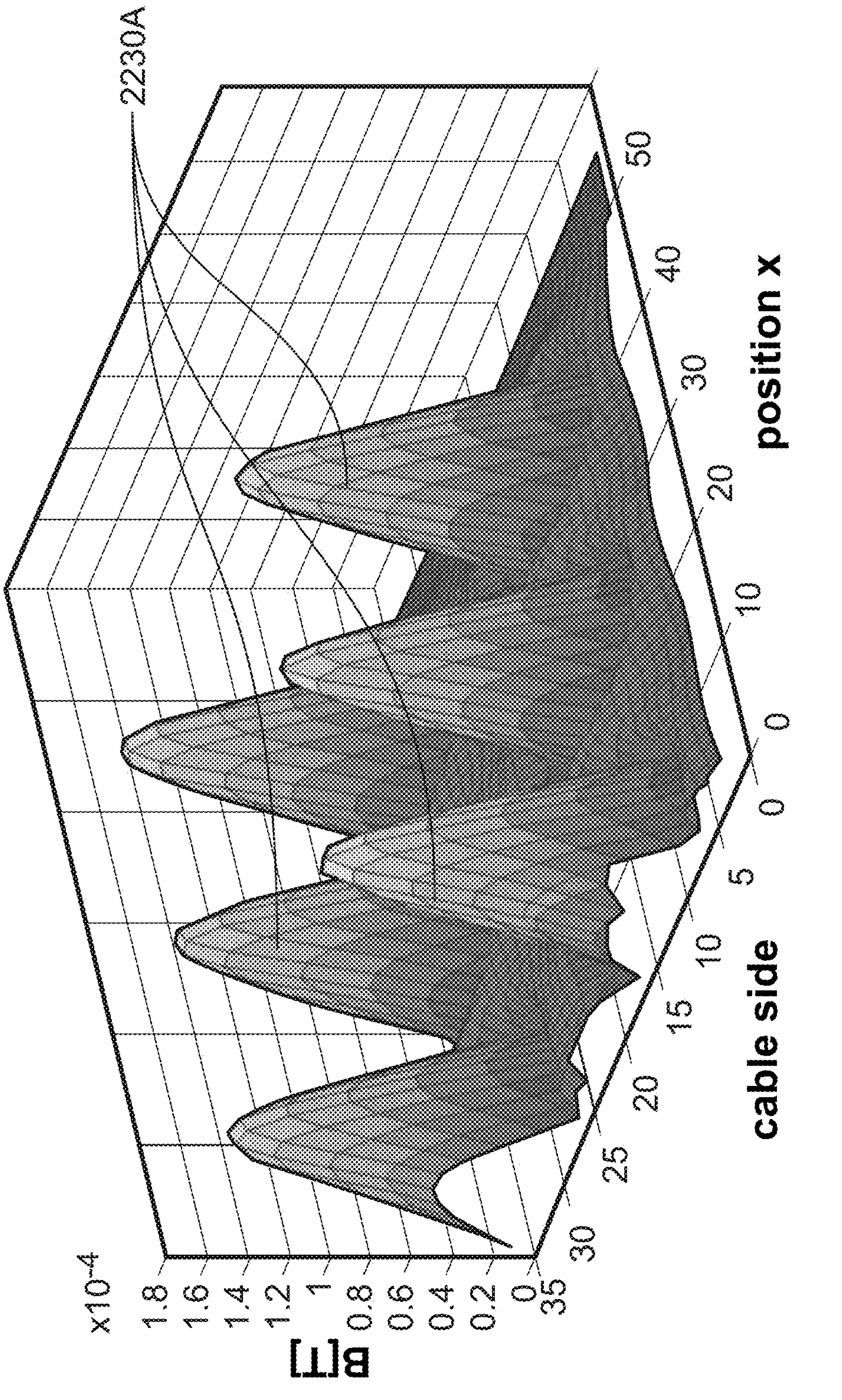
FIG. 22A shows a magnetic field profile of a preferred planar microcoil array approximately 1 mm from the surface of the array.
Figure 22B:
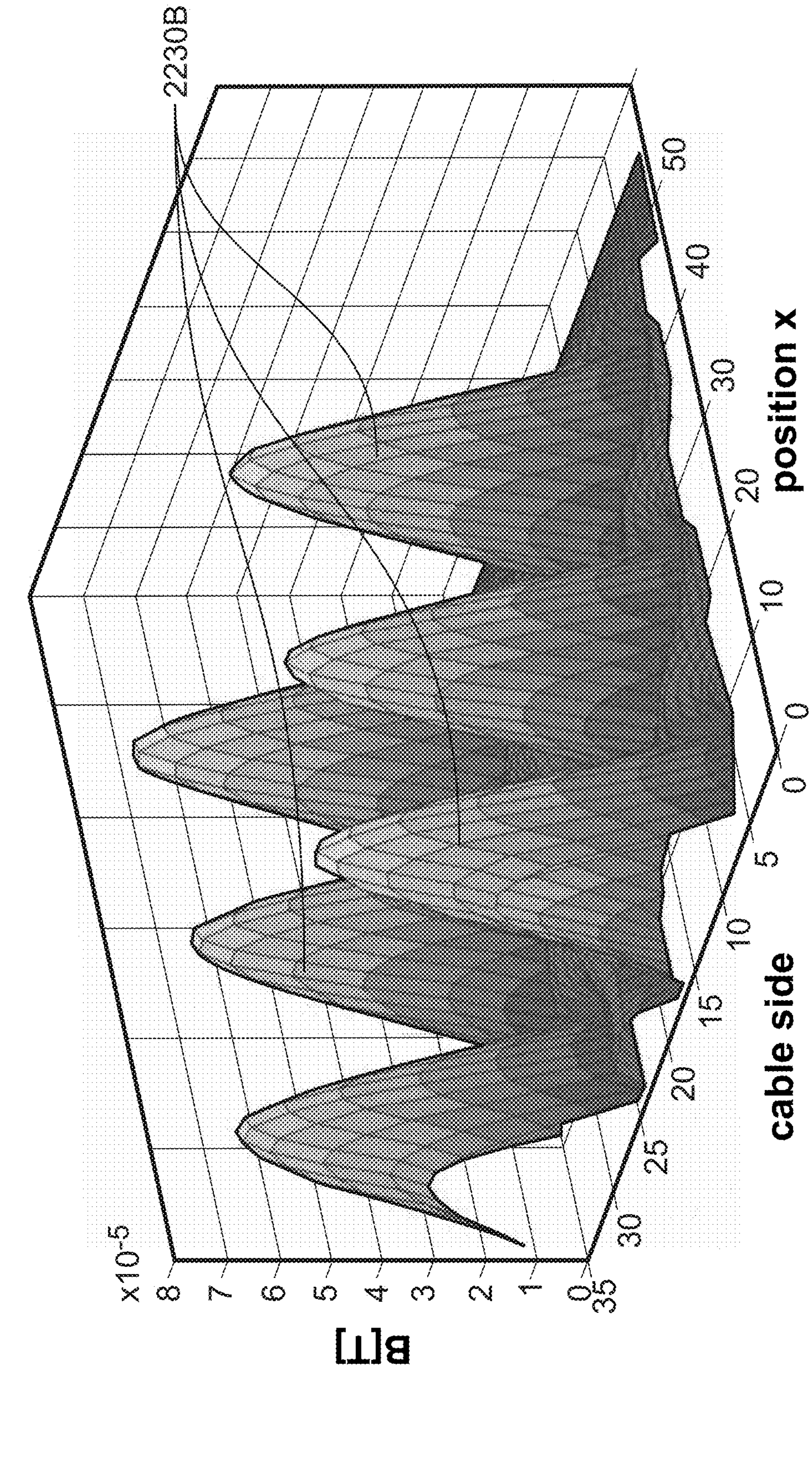
FIG. 22B shows a magnetic field profile of a preferred planar microcoil array approximately 3 mm from the surface of the array.
Figure 22C:
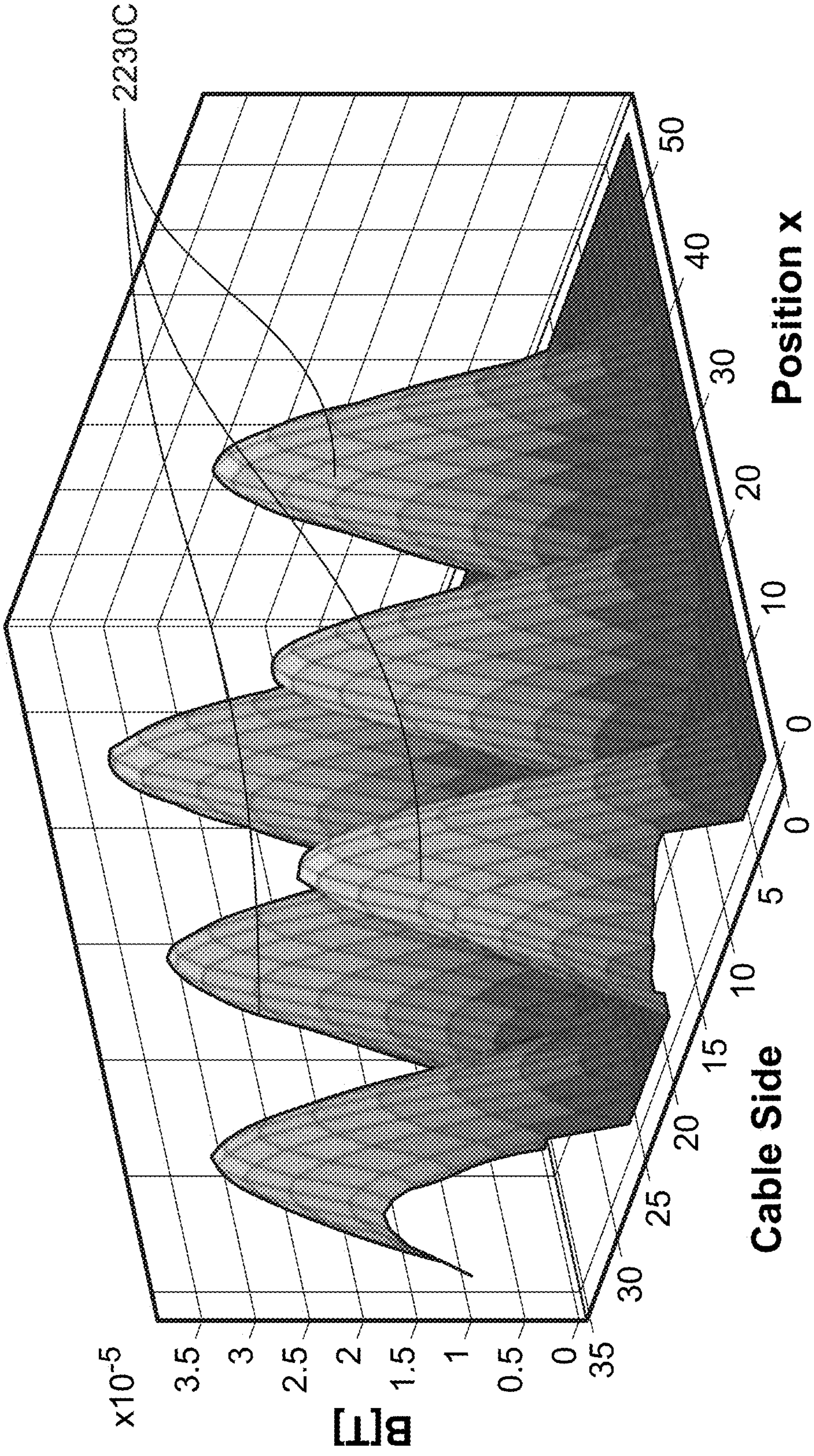
FIG. 22C shows a magnetic field profile of a preferred planar microcoil array approximately 5 mm from the surface of the array.
Figure 22D:
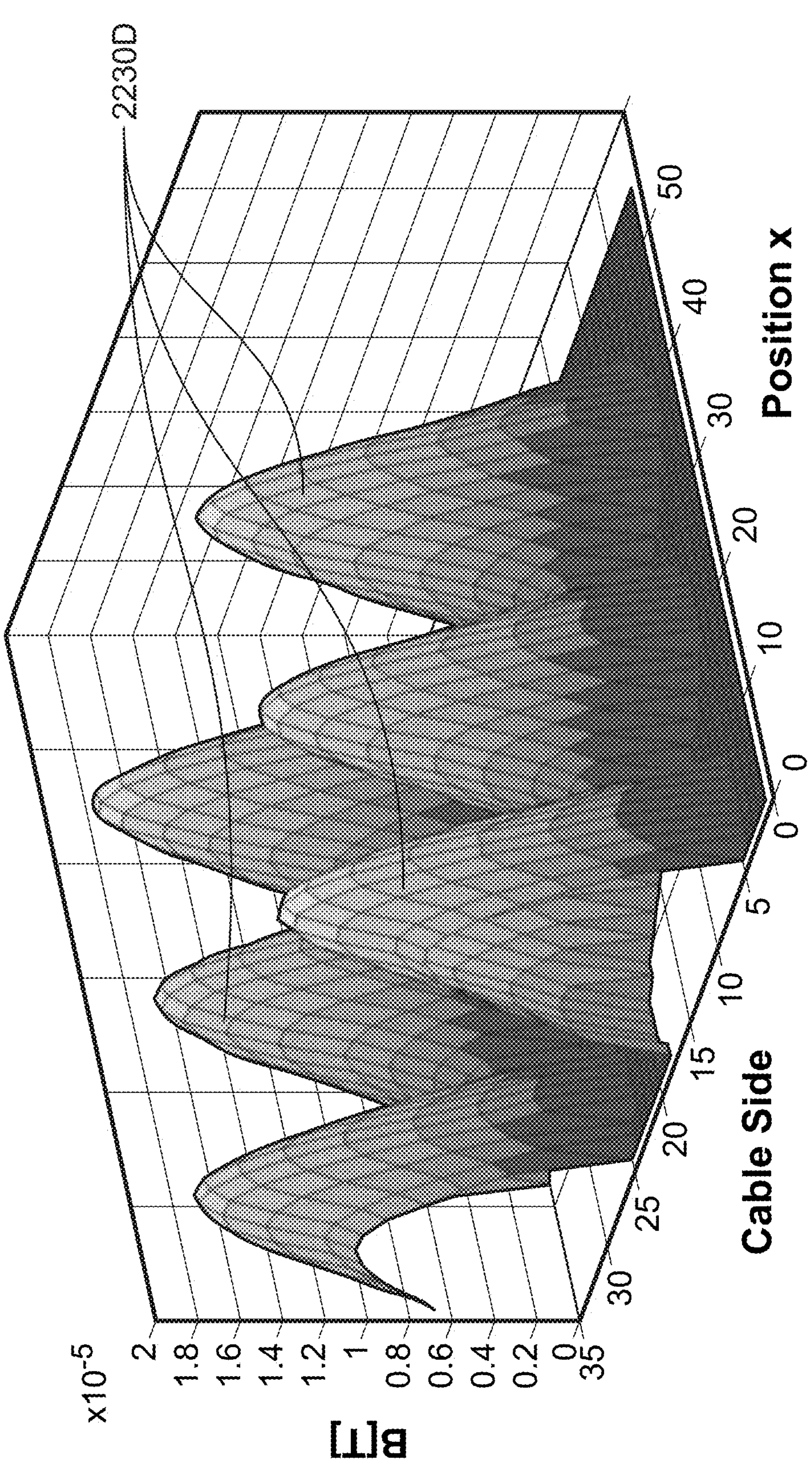
FIG. 22D shows a magnetic field profile of a preferred planar microcoil array approximately 7 mm from the surface of the array.
Figure 22E:
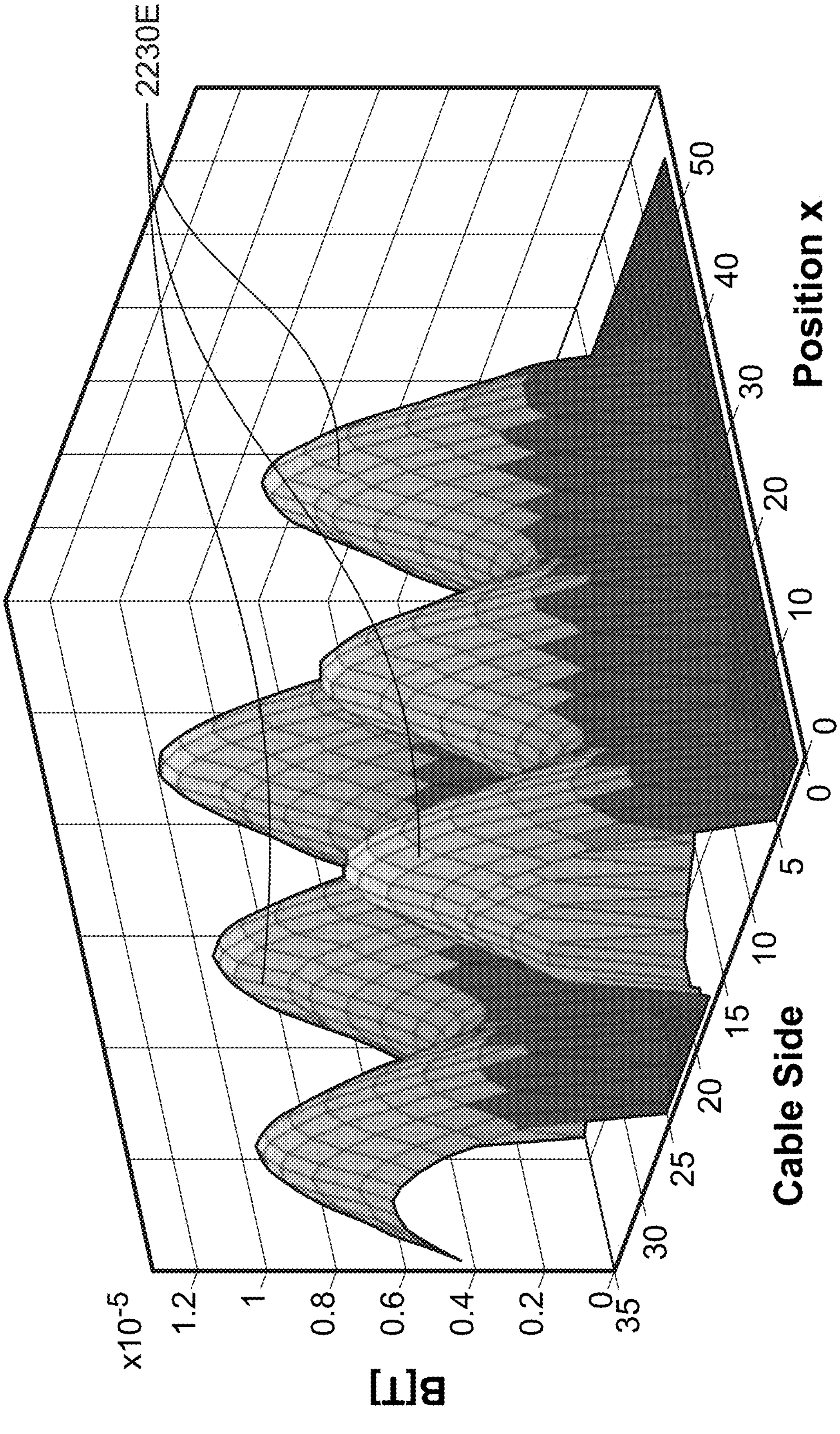
FIG. 22E shows a magnetic field profile of a preferred planar microcoil array approximately 9 mm from the surface of the array.
Figure 22F:
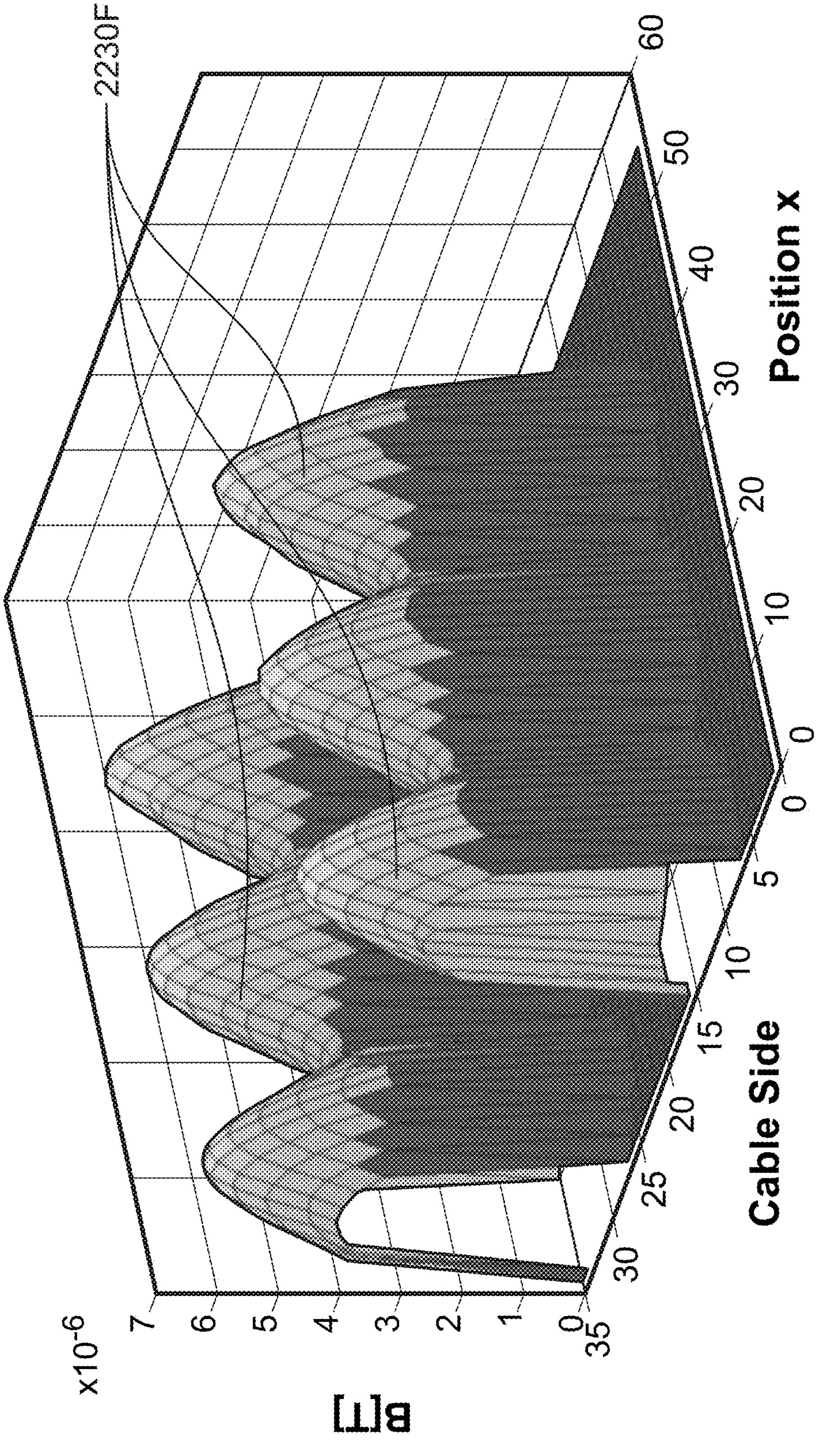
FIG. 22F shows a magnetic field profile of a preferred planar microcoil array approximately 11 mm from the surface of the array.

More specifically, each coil on the planar microcoil array concurrently generates a field which, at a 40 mA current and measured using an AC field measurement of 1kHz, that decreases in a non-linear manner as the vertical distance increases from the surface of the array. As shown in FIG. 22A, each of the coils generates a field 2230A in a range of 120 to 160 microTesla approximately 1 mm above the array and coil surface. Concurrently referring to FIGS. 22B-22F, that field decreases to 50-80 microTesla (at 3 mm, 2230B), to 25-40 microTesla (at 5 mm, 2230C), to 14-20 microTesla (at 7 mm, 2230D), to 8-12 microTesla (at 9 mm, 2230E), and to 5-7 microTesla (at 11 mm, 2230F). Accordingly, as measured vertically from the surface of array, the field of each coil initially decreases at a first rate and then, over 2-4 mm, decreases to a second rate, where the second rate is less than the first rate. Additionally, over 5-8 mm, decreases to a third rate, where the third rate is less than the first and second rates. It should be appreciated that, while a six coil configuration is shown, other numbers of coils (collectively integrated onto a single contiguous substrate) may be used, in a range of 2 to 1000 and every whole number increment therein.

Furthermore, at a given distance normal to the surface of the planar microcoil array, each coil on the planar microcoil array concurrently, yet independently, generates a field having a peak intensity that is within 0.01% to 20% of the average peak intensity of all the coils measured at the same given distance. More preferably, each coil on the planar microcoil array concurrently, yet independently, generates a field having a peak intensity that is within 0.01% to 10%, or any whole number increment therein, of the average peak intensity of all the coils measured at the same given distance.

Furthermore, at a given distance normal to the surface of the planar microcoil array, the peak intensity generated by each coil on the planar microcoil array concurrently, yet independently, decreases at a certain rate as the distance increases from the surface of the planar microcoil array. For example, in one embodiment, the average peak intensity of the magnetic field measured 1 mm normal to the surface of the planar microcoil array decreases from a first value, such as in a range of 200 to 300 microTesla, to a second value measured 2 mm normal to the surface of the planar microcoil array, such as in a range of 80 to 130 microTesla, to a third value measured 3 mm normal to the surface of the planar microcoil array, such as in a range of 50 to 90 microTesla, to a fourth value measured 4 mm normal to the surface of the planar microcoil array, such as in a range of 30 to 70 microTesla, to a fifth value measured 5 mm normal to the surface of the planar microcoil array, such as in a range of 20 to 50 microTesla, to a sixth value measured 6 mm normal to the surface of the planar microcoil array, such as in a range of 10 to 40 microTesla, to a seventh value measured 7 mm normal to the surface of the planar microcoil array, such as in a range of 5 to 35 microTesla, to a eighth value measured 8 mm normal to the surface of the planar microcoil array, such as in a range of 5 to 30 microTesla, to a ninth value measured 9 mm normal to the surface of the planar microcoil array, such as in a range of 1 to 25 microTesla, to a tenth value measured 10 mm normal to the surface of the planar microcoil array, such as in a range of 1 to 20 microTesla, and to an eleventh value measured 11 mm normal to the surface of the planar microcoil array, such as in a range of 1 to 20 microTesla.

Stated differently, the peak intensity generated by each coil on the planar microcoil array concurrently, yet independently, decreases rapidly, such as 70% to 30%, within the first 4 mm of the surface of planar microcoil array. The magnitude of the decrease lessens as one moves further away from the planar microcoil array. For example, the peak intensity generated by each coil on the planar microcoil array concurrently, yet independently, decreases less rapidly, such as 40% to 14%, within the next 4 mm of the surface of planar microcoil array. In a preferred embodiment, the peak intensity generated by each coil on the planar microcoil array concurrently, yet independently, decreases according to the following equation:

$$y = Ax^{-B}$$

where A is in a range of 100 to 600, and more preferably 300 to 400, and every whole number increment therein and where B is in a range of 1 to 2.5 (and every 0.1 decimal increment therein).

Taken together, the preferred magnetic field generated by the planar microcoil arrays are defined by four different vectors: a) the frequency of the pulse train or burst, b) the shape of each pulse in the pulse train or burst itself, c) the relative peak intensities of each pulse in the pulse train or burst itself, and d) the degradation profile from the surface of the planar microcoil arrays. In a preferred embodiment, each embodiment described herein generates a magnetic field by:

a) Using a planar microcoil array having at least one coil positioned thereon, from 2 to 100 coils positioned thereon, and preferably from 4-10 coils where each of the coils may be one or more of the embodiments described herein;

b) Driving a current to the coils positioned on a single array where the current is in the form of a pulse train, where the pulse train may be one or more of the embodiments described herein, and, more preferably, where the pulse train may be a ramping rectangular or sinusoidal pulse having a first pulse, a first time interval, a second pulse, and optionally a second time interval and a third (or more) pulses, as follows:

a. the first pulse and second pulse (and the optional third or more pulses) have pulse widths in a range of 0.001 to 0.2 seconds and preferably in a range of 0.01 to 0.02 seconds. where the first time interval and optional additional time intervals are in a range of 0.01 to 0.04 seconds (preferably a 0.025 second interval), and where the second pulse is greater than the first pulse (or vice-versa) and have current levels in a range of 5 mA to 200 mA; or b. each pulse width may be defined as a function of the period (which is the inverse of the frequency) where each pulse width is in a range of ½ to 1/50 the period length (preferably ⅕ to 1/7 the period length), where each interval between the pulses in the pulse train is in a range of ½ to 1/50 the period length (preferably ⅕ to 1/9), where the dead time between each pulse burst or train is in a range of ½ to 1/20 the period length (preferably ⅓ to ⅕), and where the second pulse is greater than the first pulse (or vice-versa) and have current levels in a range of 5 mA to 200 mA;

c) Activating the pulse train in accordance with a programmed frequency, where the programmed frequency is in a range of 0.01 Hz to 200 Hz and preferably in a range of 1 Hz to 60 Hz; and d) Activating each of the microcoil arrays in parallel or in series (or a combination thereof) such that the peak intensity generated by each coil on the planar microcoil array concurrently, yet independently, decreases according to the following equation:

$$y = Ax^{-B}$$

where A is in a range of 100 to 600, and more preferably 300 to 400, and every whole number increment therein and where B is in a range of 1 to 2.5 (and every 0.1 decimal increment therein). Accordingly, the preferred embodiments generate a magnetic field having at least four vectors of variation, resulting in a rapidly changing magnetic field profile across human tissue: a) the individual pulse shape in a given pulse train (rectangular, sinusoidal or other shaped pulse), b) the ramping (or decreasing) peak intensity between individual pulses in a pulse train, c) the frequency of the pulse train/bursts, and d) the degradation profile of the field from each of the coils over a distance. The combination of these various vectors results in a rapidly varying magnetic field profile (over both time and distance) that results in the beneficial therapeutic effects described herein.

Additionally, it is preferred to have the magnetic field vectors defining the dominant direction of the magnetic fields of the plurality of planar microcoil arrays be non-coplanar. Specifically, it is preferred that:

1. A first of a plurality of planar microcoil arrays generates a first magnetic field defined by a first vector extending in a first direction, a second of the plurality of planar microcoil arrays generates a second magnetic field defined by a second vector extending in a second direction, and a third of the plurality of planar microcoil arrays generates a third magnetic field defined by a third vector extending in a third direction, wherein the first direction, second direction, and third direction are different directions.
2. A first of a plurality of planar microcoil arrays generates a first magnetic field defined by a first vector extending in a first direction, a second of the plurality of planar microcoil arrays generates a second magnetic field defined by a second vector extending in a second direction, and a third of the plurality of planar microcoil arrays generates a third magnetic field defined by a third vector extending in a third direction, wherein the first direction, second direction, and third direction are transverse to each other.
3. Referring to FIG. 18B, a first of a plurality of planar microcoil arrays generates a first magnetic field defined by a first vector 1811 extending in a first direction, a second of the plurality of planar microcoil arrays generates a second magnetic field defined by a second vector 1812 extending in a second direction, and a third of the plurality of planar microcoil arrays generates a third magnetic field defined by a third vector 1813 extending in a third direction, wherein if the first vector 1811 and second vector 1812 were to intersect each other, they would form an angle 1822 having a value greater than 15 degrees and if the second vector 1812 and third vector 1813 were to intersect each other, they would form an angle 1823 having a value greater than 15 degrees.
4. A first of a plurality of planar microcoil arrays generates a first magnetic field defined by a first vector extending in a first direction, a second of the plurality of planar microcoil arrays generates a second magnetic field defined by a second vector extending in a second direction, and a third of the plurality of planar microcoil arrays generates a third magnetic field defined by a third vector extending in a third direction, wherein the first direction, second direction, and third direction are non-parallel and intersect each other.

Planar Microcoil Arrays and Controllers

Figure 6:
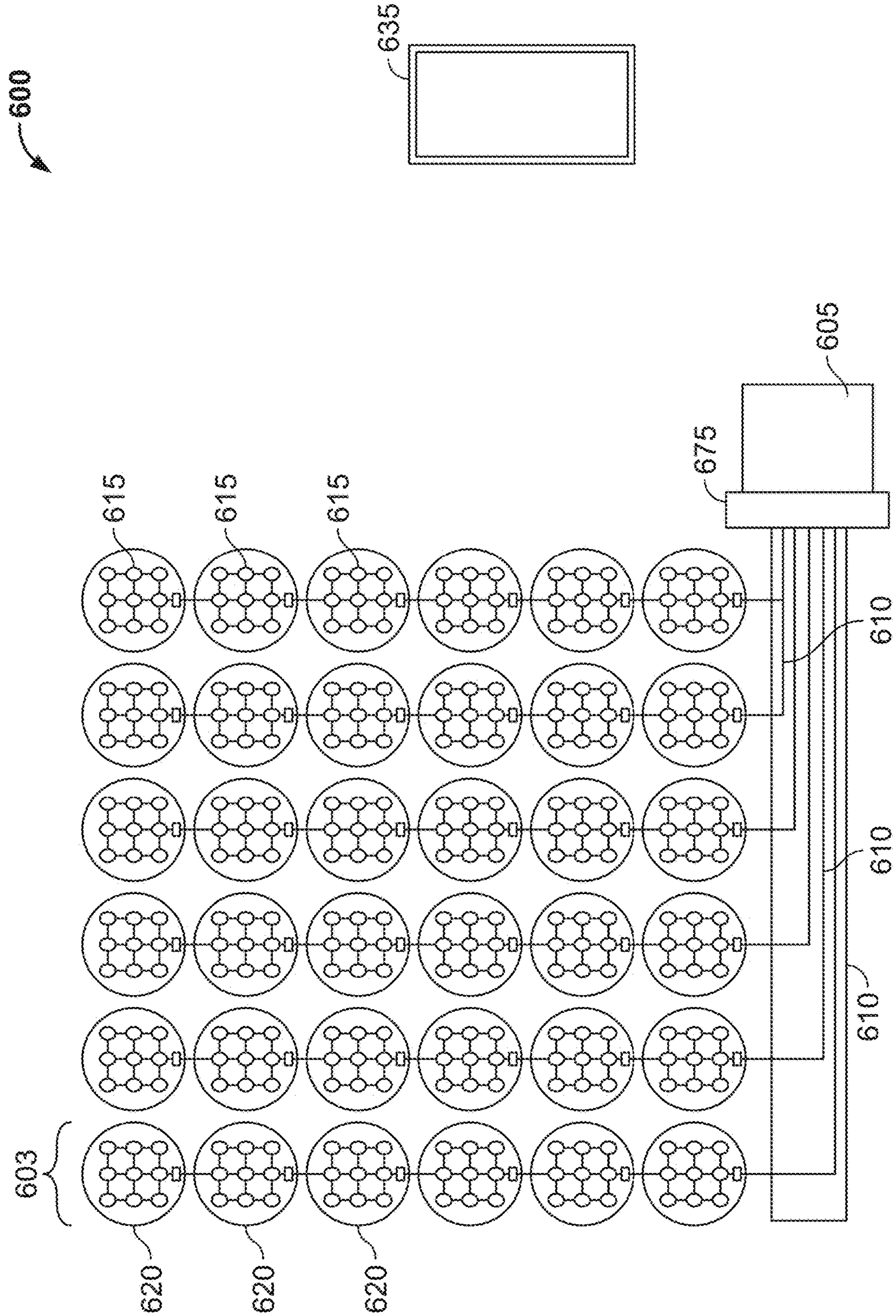
FIG. 6 depicts an exemplary planar microcoil system with multiple arrays of microcoils.
Figure 15:
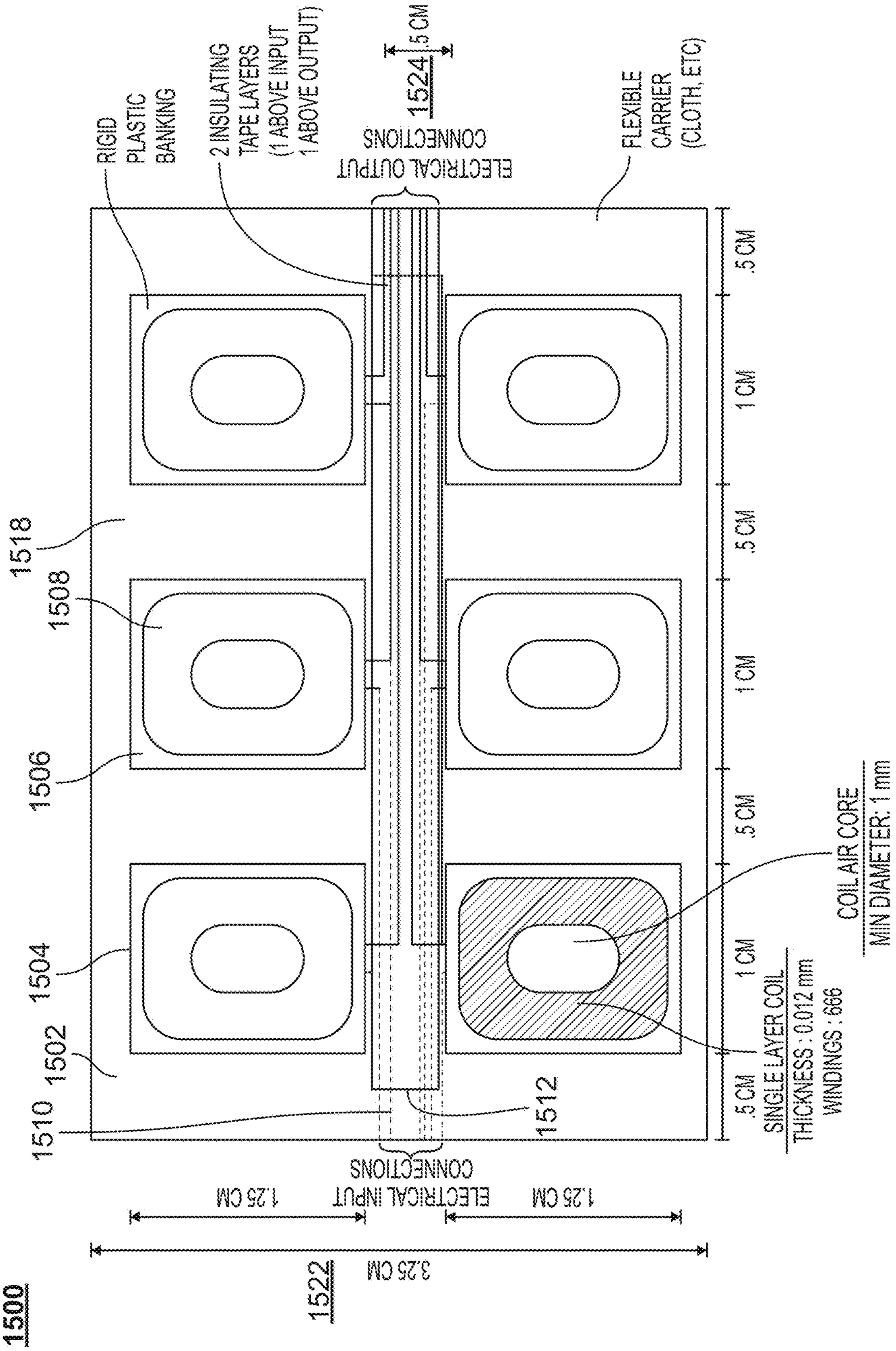
FIG. 15 is an exemplary array of planar coils.

Referring to FIG. 6, the therapeutic system 600 comprises a flexible patch or substrate 620 having one or more planar microcoils 620 positioned thereon. The flexible patch or substrate 620 comprises a flexible material, such as Kapton, polyimide, or any other suitable non-conductive flexible material. A single patch 620 comprising a plurality of planar microcoils 615 constitutes a planar microcoil array 630, as shown in FIGS. 7B and 15. Each of the arrays is connected in parallel or in series to a controller 605. For example, the set of patches 620 in column 603 may be connected serially, while the patches in columns adjacent to column 603 may be connected in parallel to the patches in column 603 via wires, or electrical communication pathways, 610.

In one embodiment, the single patch 620 comprises two or more planar microcoils 615 or between 2 and 100 microcoils or more than 2 planar microcoils. In one embodiment, the set of patches used in any specific application, including in any piece of clothing, may have different sizes (e.g. surface areas), and therefore different numbers of planar microcoils, in order to better fit or suit different parts of a person's anatomy. For example, clothing positioned adjacent to the patient's torso may have larger patches, and more planar microcoils, integrated into a single patch than clothing positioned near the patient's toes or fingers, which may have smaller patches to better contour to the curves and crevices near the patient's toes or fingers, as further discussed in relation to FIGS. 12A to 12E.

Figure 28:
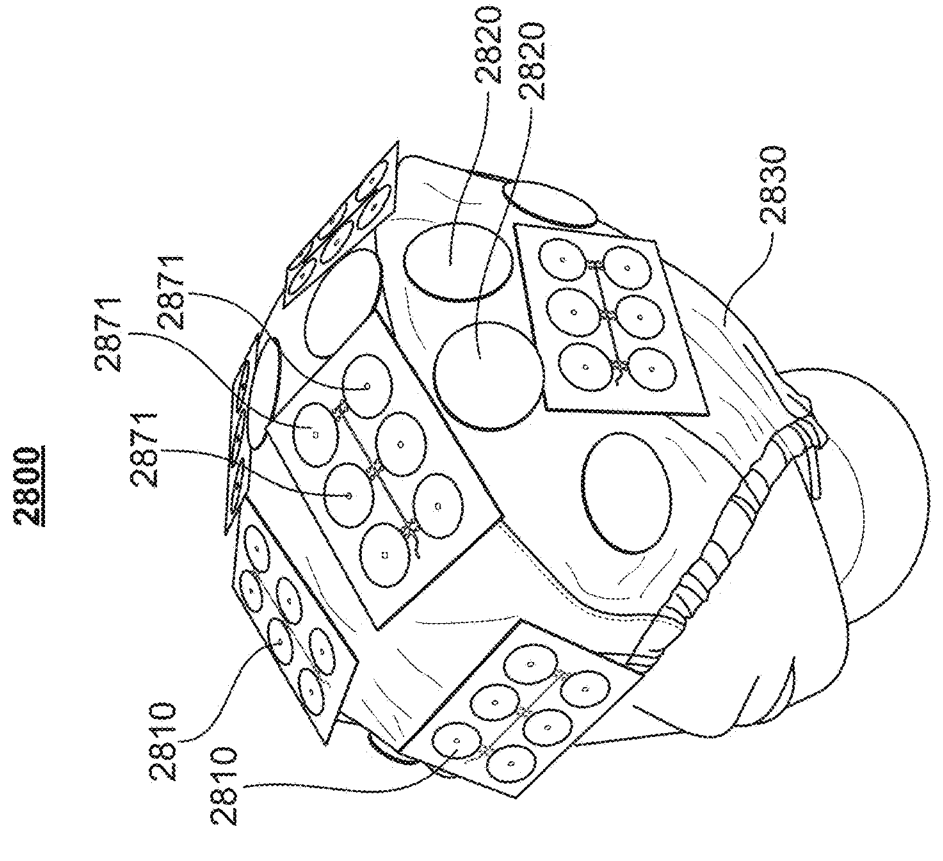
FIG. 28 shows an embodiment with both EEG electrodes and microcoil arrays.

For each of the embodiments disclosed herein, it is preferred that the planar microcoils integrated into the same array or patch are positioned in the same plane relative to the body surface being treated. For example, when directing pulsed electromagnetic fields toward a user's brain, more than one planar microcoil integrated into a single substrate or array are positioned in the same plane relative to the surface of the user's brain. As shown in FIG. 28, a single array 2810 has a plurality (2 or more) discrete planar microcoils 2871 (which are serially energized or energized in parallel) embedded therein and configured such that the plurality of discrete planar microcoils 2871 (which are serially energized or energized in parallel) are in the same plane relative to the user's brain surface, where that same plane does not intersect or pass through the user's brain surface. This "same planar" approach is used on any and all body parts subject to treatment, including arms, legs, feet, ankles, joints, torso, neck, face, or any other anatomical area. This enables the discrete fields created by each of the separate and discrete coils to predictably combine over a distance to yield the preferred magnetic field profile and is more preferable than other configurations such as 2 or more discrete magnetic field emitters positioned in different planes or 2 or more discrete magnetic field emitters positioned in a plane that intersects through the user's brain surface. This approach, where the Z axis of the microcoils is directed perpendicular to the user's anatomical surface, is also preferred relative to emitters that encircle the user's brain, where the Z axis of the emitter coil is parallel with a longitudinal axis passing through the height of the user.

Figure 17:
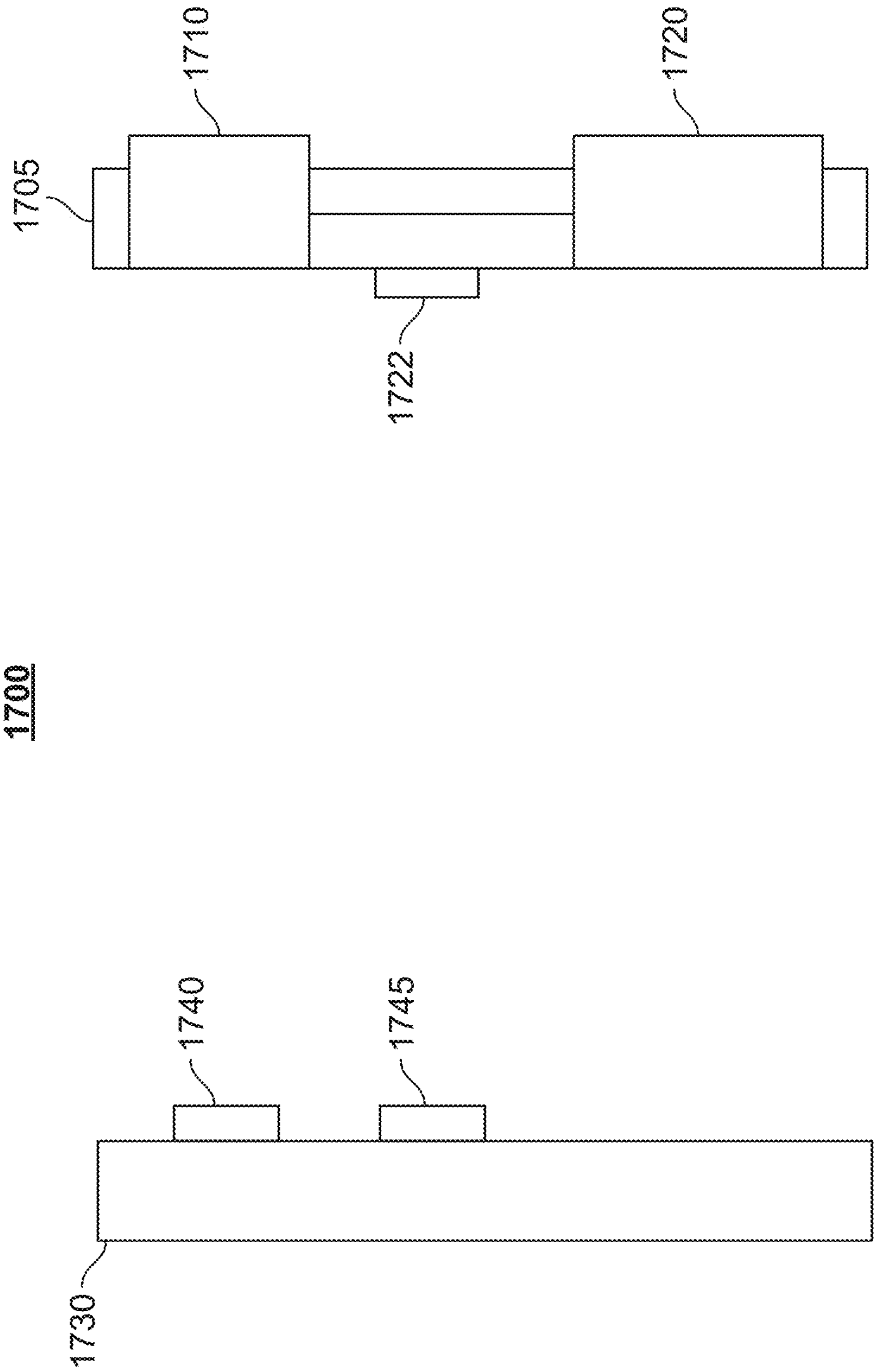
FIG. 17 is an exemplary docking station configured to interface with a controller.

Controller 605 may be programmed to concurrently stimulate all the planar microcoils in all the patches, all planar microcoils on a subset of the patches, or a subset of planar microcoils on a subset of the patches. Further, the controller 605 may be optionally configured to removably interface with a docking station 675. Referring to FIG. 17, a docking system 1700 is comprised of a controller 1705 having circuitry 1710 configured to generate current signals in accordance with the stimulation protocols described herein, a first mechanical connection 1722, and a power source, such as a battery 1720, and a docking station 1730, having an electrical connection 1740 configured to mate to the circuitry 1710 and a second mechanical connection 1745 configured to mate with the first mechanical connection 1722. In one embodiment, the electrical connection 1740 comprises one or more pins having data stored therein indicative of the type of clothing, device, or application the docking station 1730 is integrated into. As described below, the planar microcoil arrays are integrated into clothing and, preferably, the docking station 1730 is as well. The controller 1705 is removably attachable to the docking station 1730 such, upon connecting the first mechanical connection 1722 to the second mechanical connection 1745, the circuit 1710 is automatically placed in electrical communication with, and is therefore capable of driving a current through, electrical interface 1740. Further, upon being automatically interfaced with electrical interface 1740, the circuit 1710 is configured to read the data indicative of the type of clothing or planar array configuration to which the docking station 1730 is connected, thereby allowing a user to use one controller 1705 with multiple different clothing types and further allowing the controller 1705 to be charged or serviced separate from the docking station 1730, planar microcoil arrays, and clothing into which both are integrated. The mechanical connection may be a male/female latch combination, a male/female snap combination, or any other male/female mechanical combination.

In one embodiment, programmatic instructions on a separate computing device, such as a phone, 635, are executed to capture pain data from the patient, analyze the pain data to determine which areas of the patient's anatomy requires pulsed electromagnetic field therapy, and, depending on the garment being worn by the patient, activate one or more planar microcoils on one or more patches to target the determined areas requiring pulsed electromagnetic field therapy.

Figure 13:
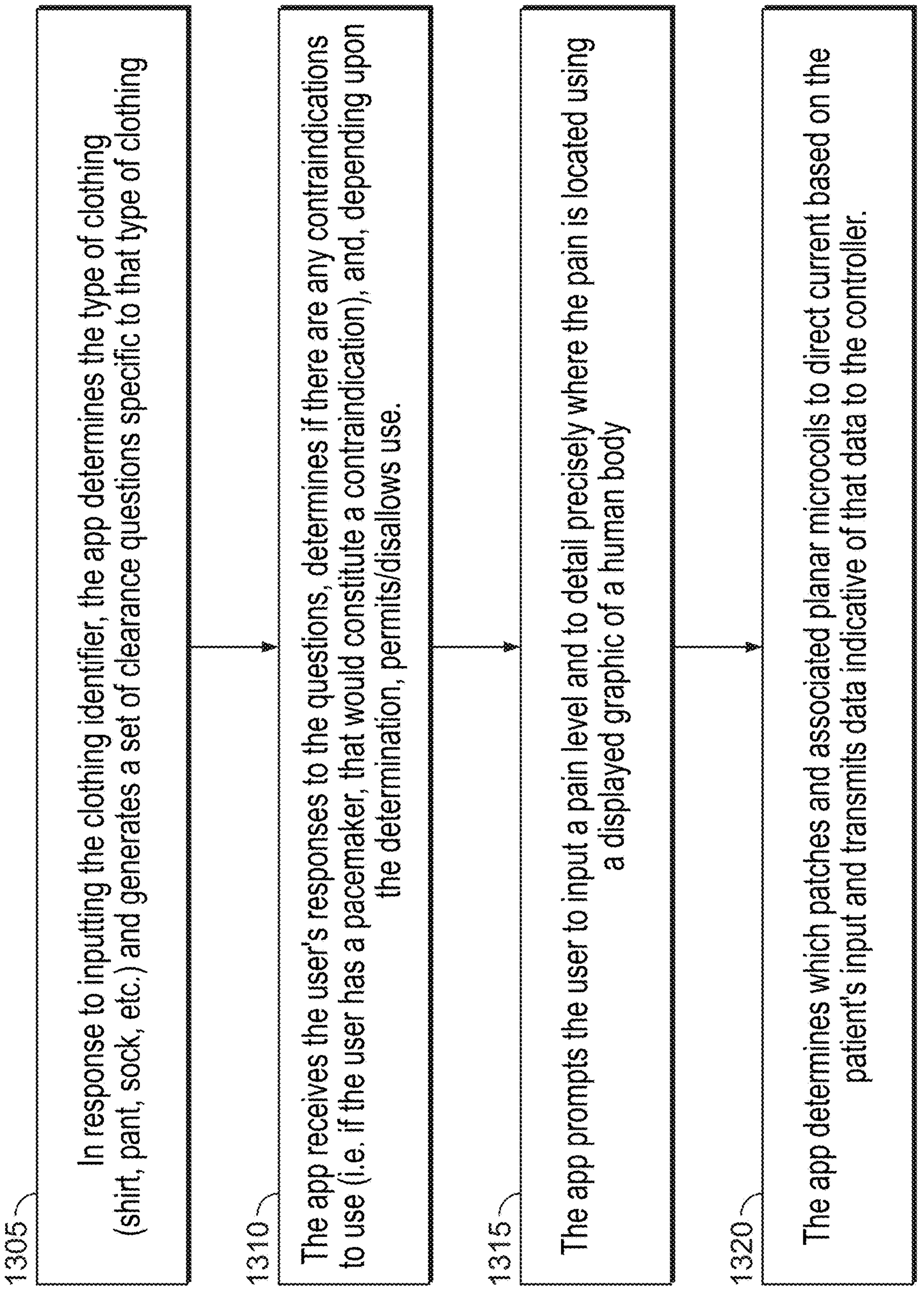
FIG. 13 is a flowchart showing an exemplary use of the system.
Figure 14:
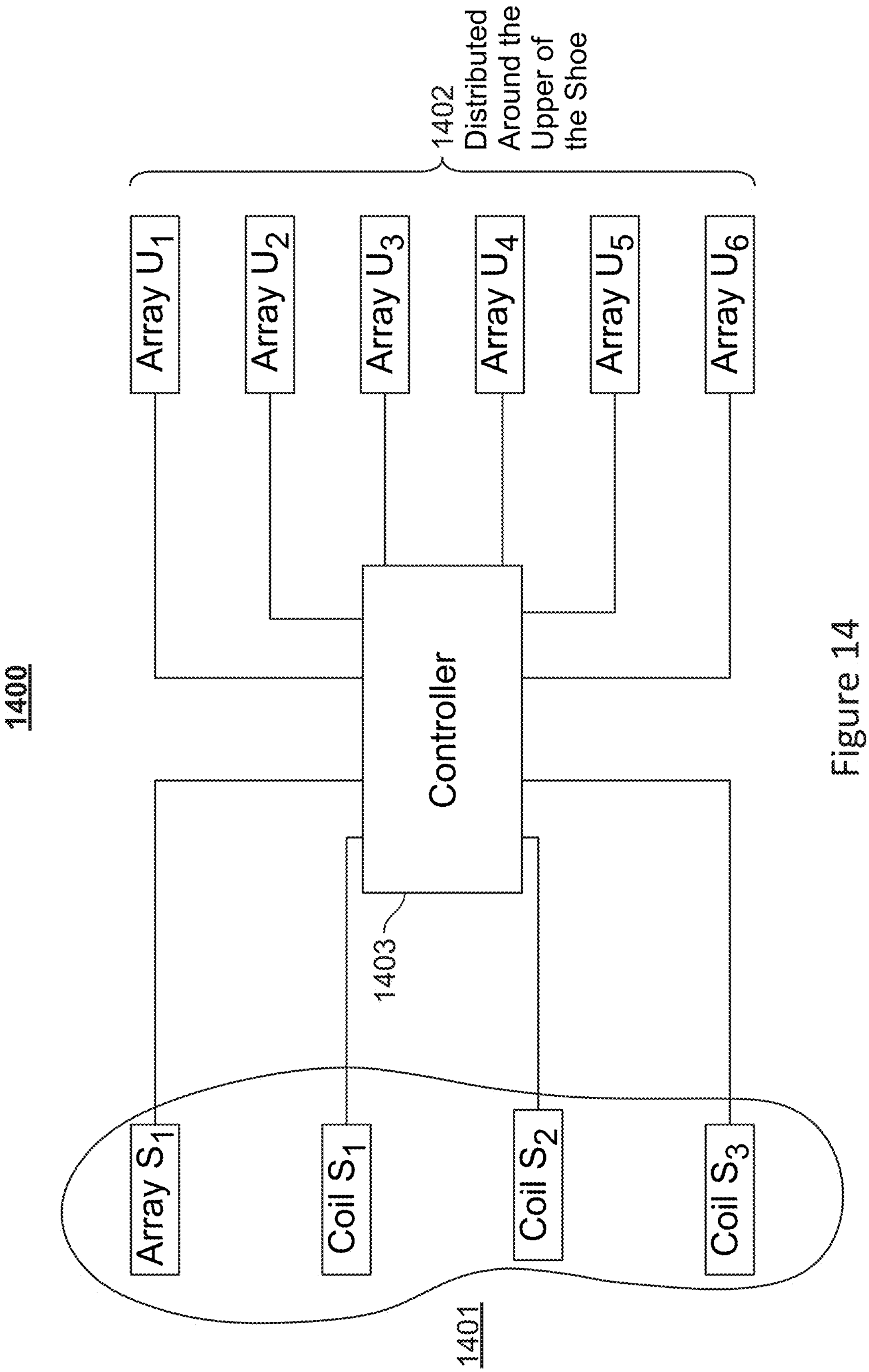
FIG. 14 is an exemplary footwear system.

More specifically, referring to FIG. 13, a patient first acquires a specific piece of clothing with the patches and planar microcoil arrays integrated therein, as further described below. The patient downloads an app onto his or her phone 635, creates an account, and inputs a clothing identifier, using a QR code, RFID tag, serial number or another identifier. In response to inputting the clothing identifier, the app determines the type of clothing (shirt, pant, sock, etc.) and generates a set of clearance questions specific to that type of clothing 1305. Clearance questions may be directed toward making sure the device is not used proximate to implanted devices, metal or other structures that, if positioned on the patient's skin, could experience induced electrical currents if pulsed electromagnetic fields are applied thereto.

After receiving the user's response to the clearance questions, the app determines if there are any contraindications to use (i.e. a pacemaker, spinal implants, pins, or other implanted devices) 1310 and, depending upon the determination, generates an activation code which is transmitted to the controller 605. If the user inputted data is contraindicated for use with the specific piece of clothing, the app recommends the user first activate the device under the supervision of a physician. An override code, which would require the user to actively acknowledge the risks involved, may be provided by the app and either wirelessly transmitted to the controller 605 or displayed to the user who may manually input it into the controller 605.

If user, relative to the identified piece of clothing, is cleared for use and the controller 605 is activated, the app then prompts the user to input data indicative of the patient's pain level and location of the pain 1315. The app may do so by generating a visual analog scale that the user may use to indicate a level of pain being experienced (i.e. on a scale of 1 to 10 or using graphical emoj is) and a graphical image of a human body, or portions thereof, to allow the user to identify, by pointing to the right location on the graphical image, the locus of pain. In one embodiment, the graphical image used is specific to the type of clothing identified using the original code indicative of the clothing acquired. Once the degree and/or locus of pain has been identified, the app may determine which set of patches and/or set of planar microcoils should be energized in order to treat the inputted level and location of pain 1320 and transmit such data to the controller. For other conditions, other questions may be posed, such as degree and timing of memory lapses, degree and timing of tremors, or degree and timing of other symptoms.

Figure 9:
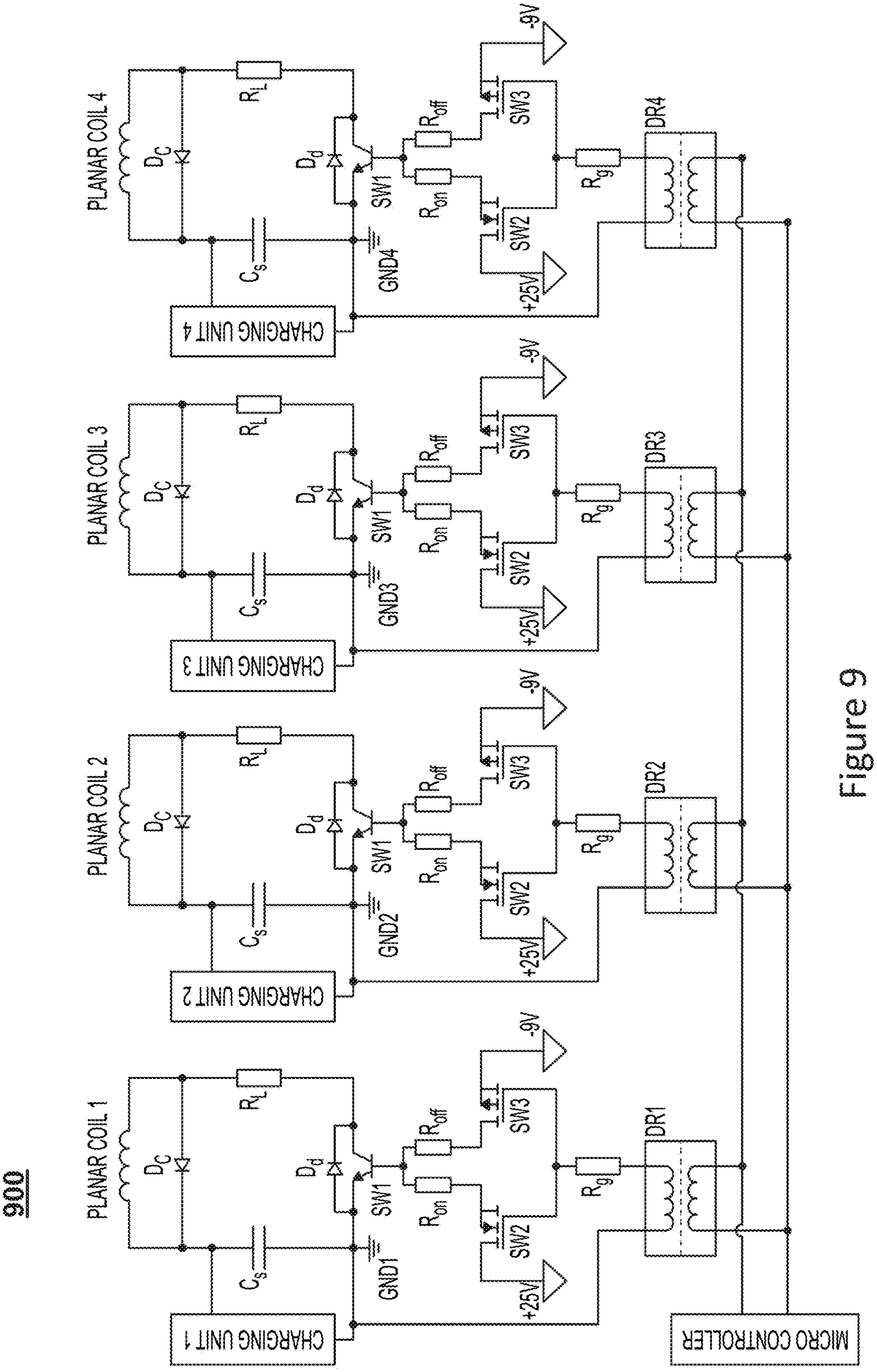
FIG. 9 depicts an exemplary planar microcoil circuit diagram.

FIG. 9 describes an exemplary circuit 900 configured to generate electrical currents, in accordance with stimulation protocols described below. The exemplary circuit may be in the controller 605 or distributed between the controller 605 and patches 620.

Referring to FIG. 15, the coil array 1500 may comprise a flexible substrate 1502 upon which a plurality of coil pieces 1504 are attached. Each coil piece 1504 comprises a backing, such as a hard-plastic backing 1506, upon which a coil 1508 is wound or molded. The coils may be any of the rectangular spiral, rectangular non-spiral, circular spiral, circular non-spiral or other shaped coils. The coil pieces 1504 are preferably spaced from each other in a range of 0.1 cm to 10 cm, preferably 0.5 cm to 2 cm, and preferably less than 15 cm, or any numerical increment therein. Each coil 1508 comprises an input lead and an output lead. The input lead of each coil 1508 may be routed to one side of the array 1510 and may be kept separate from each other by one or more layers of insulation tape 1512. The input leads of all the coils 1508 of the array 1500 are integrated or multiplexed together to form an input terminal 1522 to which electrical current from the controller and energy source may be directed. Accordingly, all the coils 1508 of the array 1500 may be concurrently energized by directing current from a single energy or battery source to just one input terminal 1522.

Similarly, the output lead of each coil 1508 may be routed to one side of the array 1514 and may be kept separate from each other by one or more layers of insulation tape 1512. The output leads of all the coils 1508 of the array 1500 are integrated or multiplexed together to form an output terminal 1524 to which electrical current from the controller and energy source may be directed. Accordingly, the output leads of all the coils 1508 of the array 1500 are integrated or multiplexed together to form an output terminal 1524 to which electrical current may be directed from the array to the controller and energy source. Further, all the coils 1508 of the array 1500 may form a closed circuit by directing current from the array to the single energy or battery source via the one output terminal 1524.

Preferably, positioned between each coil piece 1504 or coil 1508 is a material that may act as a cushion, barrier, or padding 1518 that functions to both prevent the coil pieces from 1504 shifting and to gently position the array 1500 against the user's skin. Additionally, or alternatively, area 1518 may include an adhesive to attach, secure, or otherwise fixedly position the array 1500 against the user's skin. Additionally, or alternatively, area 1518 may include an attachment mechanism, such as Velcro or snaps, to attach area 1518, and therefore array 1500, to another substrate or material to form a piece of clothing, as further discussed below.

Figure 16:
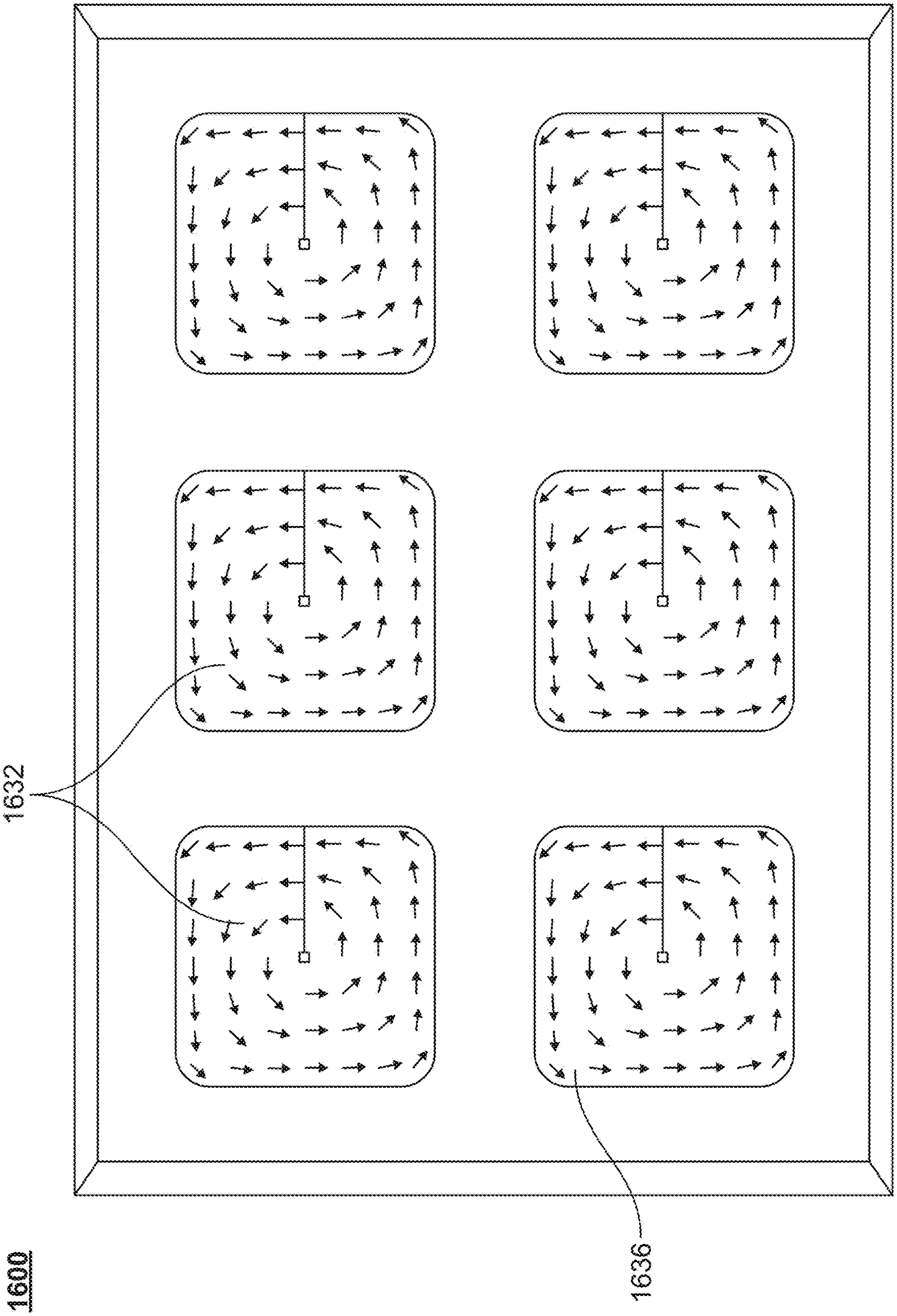
FIG. 16 is an exemplary current directionality of a coil array.

It should be appreciated that the directionality of the current of each coil may be modified to achieve a desired magnetic flux level by properly routing its input lead or output lead to the input or output side of the array 1500. Referring to FIG. 16, in this array 1600, the top coils 1632 and the bottom coils 1636 have counterclockwise currents.

The directionality of the current of a coil may be modified by changing which lead, extending from that coil, is routed to the input terminal and is routed to the output terminal. For example, if lead A is directed to the input terminal and lead B is directed to the output terminal, the current directionality of the corresponding coil may be clockwise. That current directionality may be switched to become counterclockwise by routing lead A to the output terminal and lead B to the input terminal It should further be appreciated that the form factor and range of coil sizes and relative separation between coil pieces are important to achieving two core objectives. First, the coil footprint should not be too large, and the coil separation should not be too small, otherwise the array will not be flexible enough to conform to uneven or non-planar portions of a user's body.

Second, the coil footprint should not be too small, and the coil separation should not be too large, otherwise the array will not generate a sufficiently large magnetic flux for therapeutic purposes. Hence, the dimensions and distances disclosed herein have a distinct utility and are not merely aesthetic in nature.

Stimulation Protocols

Figure 10A:
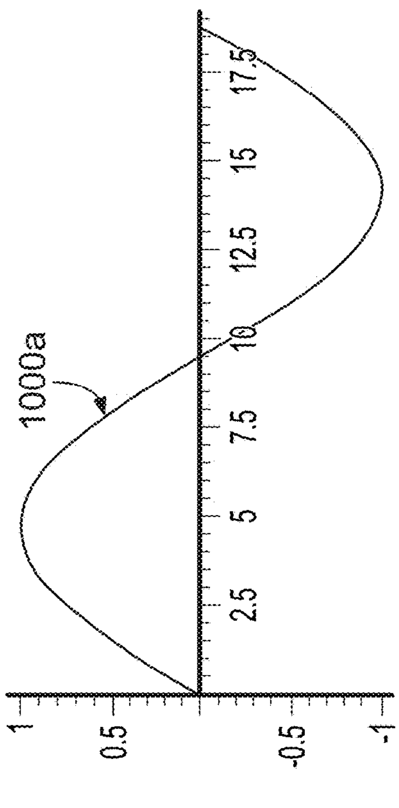
FIG. 10A depicts a first pulsed electromagnetic frequency signal which may be implemented to administer the therapies described herein.
Figure 10B:
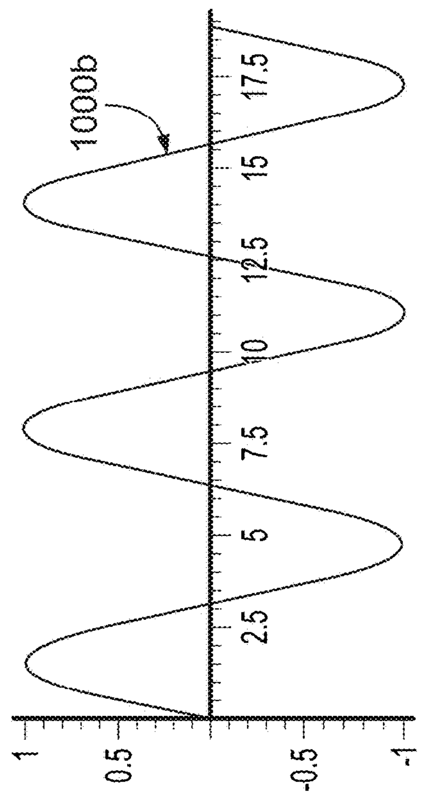
FIG. 10B depicts a second pulsed electromagnetic frequency signal which may be implemented to administer the therapies described herein.
Figure 10C:
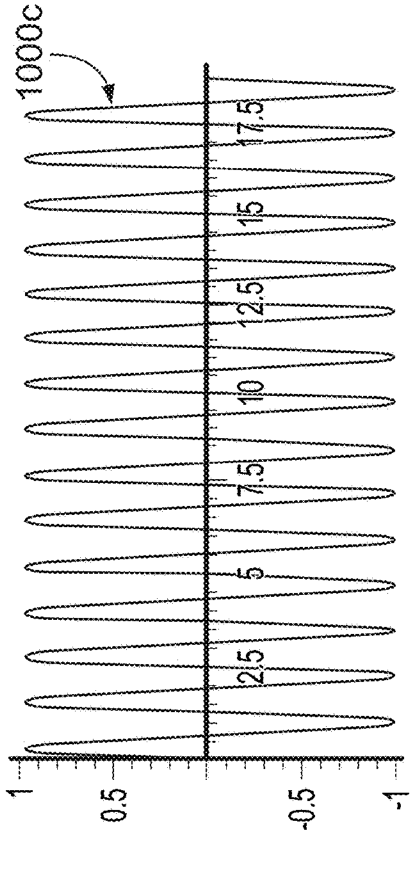
FIG. 10C depicts a third pulsed electromagnetic frequency signal which may be implemented to administer the therapies described herein.
Figure 10D:
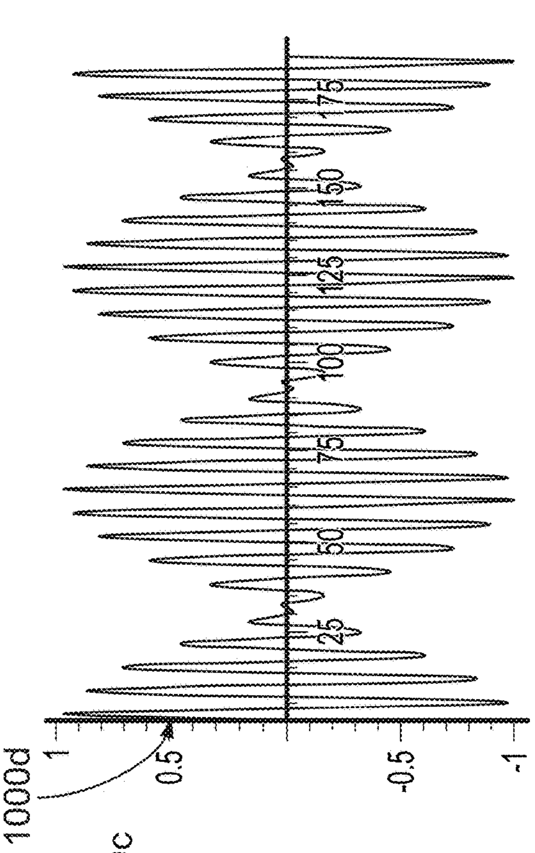
FIG. 10D depicts a fourth pulsed electromagnetic frequency signal which may be implemented to administer the therapies described herein.
Figure 10F:
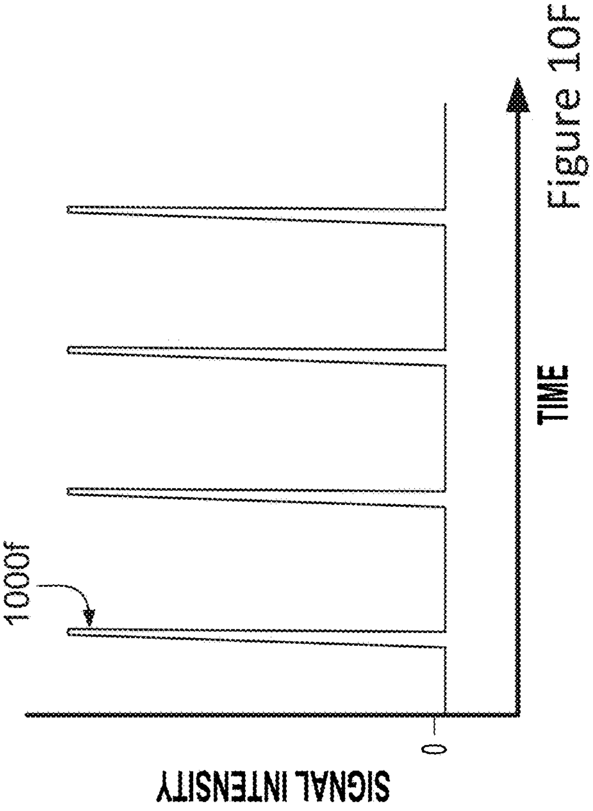
FIG. 10F depicts a sixth pulsed electromagnetic frequency signal which may be implemented to administer the therapies described herein.
Figure 10E:
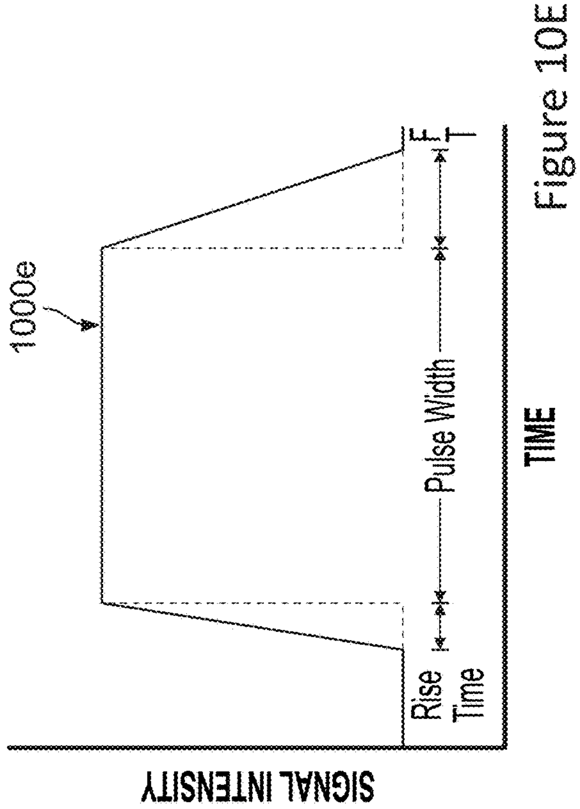
FIG. 10E depicts a fifth pulsed electromagnetic frequency signal which may be implemented to administer the therapies described herein.
Figure 10G:
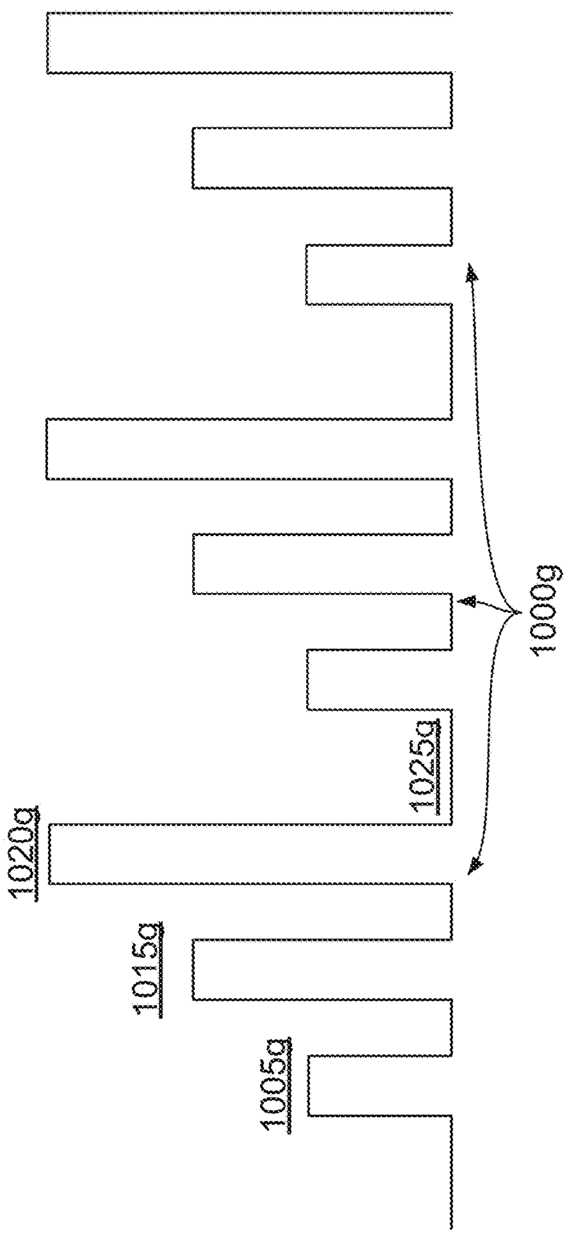
FIG. 10G depicts a seventh pulsed electromagnetic frequency signal which may be implemented to administer the therapies described herein.
Figure 11A:
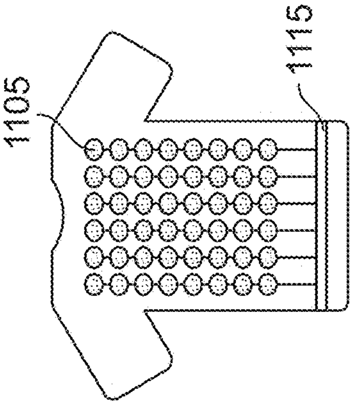
FIG. 11A depicts a shirt with embedded planar microcoil arrays, in accordance with some embodiments of the present specification.
Figure 11B:
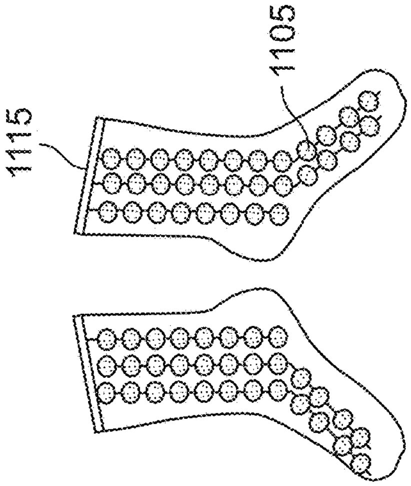
FIG. 11B depicts a pair of socks with embedded planar microcoil arrays, in accordance with some embodiments of the present specification.
Figure 11C:
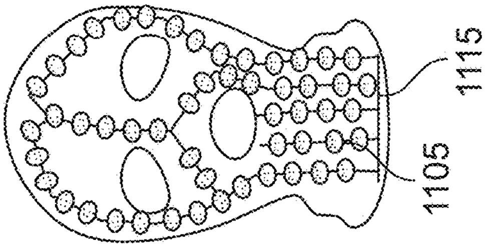
FIG. 11C depicts a head covering with embedded planar microcoil arrays, in accordance with some embodiments of the present specification.
Figure 11D:
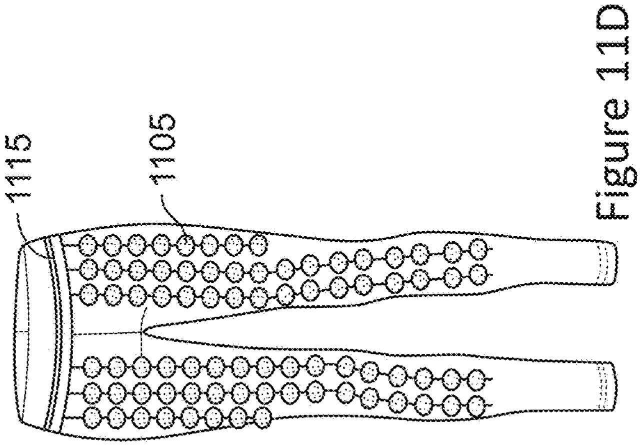
FIG. 11D depicts a pair of pants or leggings with embedded planar microcoil arrays, in accordance with some embodiments of the present specification.
Figure 11E:
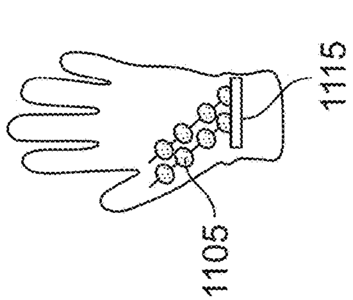
FIG. 11E depicts a glove with embedded planar microcoil arrays, in accordance with some embodiments of the present specification.
Figure 12C:
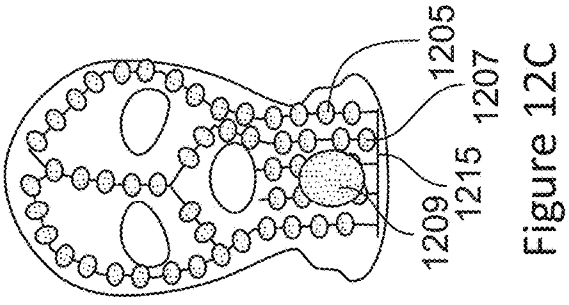
FIG. 12C depicts a head covering with embedded planar microcoil arrays, in accordance with other embodiments of the present specification.
Figure 12B:
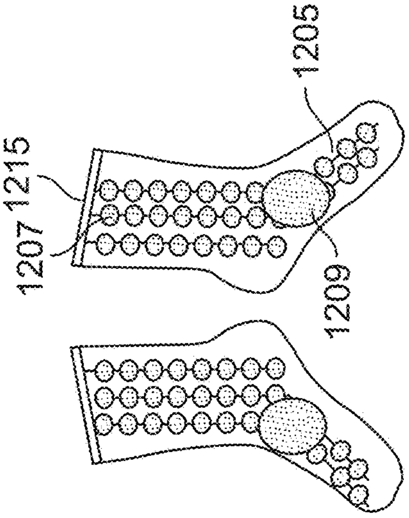
FIG. 12B depicts a pair of socks with embedded planar microcoil arrays, in accordance with other embodiments of the present specification.
Figure 12E:
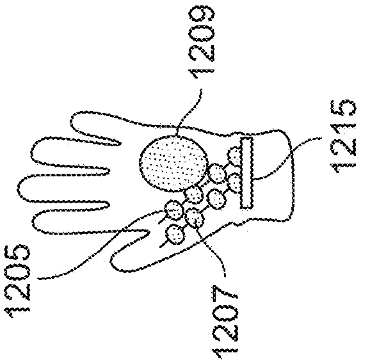
FIG. 12E depicts a glove with embedded planar microcoil arrays, in accordance with other embodiments of the present specification.
Figure 12D:
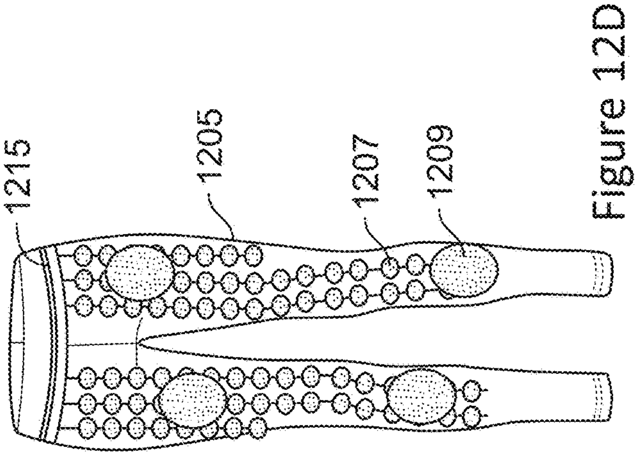
FIG. 12D depicts a pair of pants or leggings with embedded planar microcoil arrays, in accordance with other embodiments of the present specification.
Figure 12A:
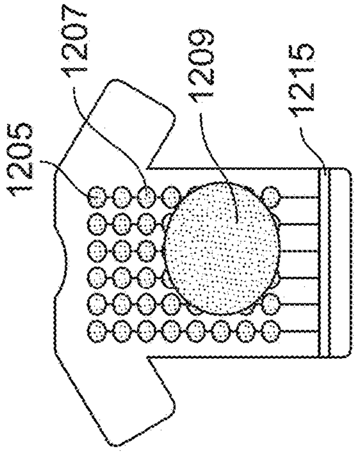
FIG. 12A depicts a shirt with embedded planar microcoil arrays, in accordance with other embodiments of the present specification.

The controller is configured to generate an electrical current, and selectively transmit the electrical current to all of the plurality of planar microcoils, or a subset of the plurality of planar microcoils, in order to generate pulsed electromagnetic fields in accordance with one or more of FIGS. 10A to 10G. The electrical current may be a sinusoidal curve 1000*a* defined by a first period, a sinusoidal curve 1000*b* defined by a second period, or a sinusoidal curve 1000*c* defined by a third period where each of the three periods are of different lengths. The electrical current may also be a sinusoidal curve 1000*d* having a varying amplitude. In other embodiments, the electrical current pulse may be a trapezoidal 1000*e*, a spike 1000*f*, or square shaped 1000*g*. Referring to FIG. 10G, in one embodiment, the stimulation pulse, or shape of the electrical current pulse, may comprise a series of pulse trains 1000*g*, each defined by a set of ramping square pulses, 1005*g*, 1015*g*, 1020*g*. In particular, within a stimulation session, each pulse train 1000*g* may be initiated at a frequency in a range from 5 Hz to 200 Hz, preferably in a range of 8 to 30 Hz. Each pulse train 1000*g* comprises at least 1 square pulse, typically having an amplitude of between 20 and 100 mA. More preferably, each pulse train 1000*g* comprises a series of ramping square pulses, 1005*g*, 1015*g*, 1020*g*, that increase in amplitude from a first pulse in a range of 20 to 50 mA, to a second pulse in a range of 40 to 70 mA, to a third pulse in a range of 60 to 100 mA. It should be appreciated that other ramping configurations could be implemented, including a down ramping pulse that, in the course of the pulse train, decreases in amplitude.

A stimulation session may go from 1 minute to 24 hours. As described above, within a given stimulations session, you may have a series of pulse bursts. A pulse burst may have one or more pulses. Each pulse in the pulse burst may have the same or different pulse shapes, as shown in FIGS. 10A-10F. Each pulse in the pulse burst may have the same or different amplitude. In one preferred stimulation, there are multiple pulses in a pulse burst where the amplitude of each pulse burst ramps from low to high or ramps from high to low. Each pulse amplitude causes a generation of a field in the range of 1 to 10000 microTesla, preferably 3 to 500 microTesla, preferably 10 to 200 microTesla. The frequency of the pulse burst is in a range of 1 to 500 Hz, preferably 5 to 30 Hz, and more preferably 6 to 15 Hz. Amperage is dependent on the selected planar microcoil design but is in a range of 1 mAmp to 5Amp. In embodiments, the pulse bursts may have characteristics as described with reference to Table 2 below:

TABLE 2

| Pulse Burst Characteristics | | | | |
|---|---|---|---|---|
| Amplitude of electrical signal generated by the controller | 1 m Amp to 1 Amp (preferably 0.1, 0.2, 0.4 0.5, 0.55 Amps) | 1 m Amp to 1 Amp (preferably 0.1, 0.2, 0.4 0.5, 0.55 Amps) | 1 m Amp to 1 Amp (preferably 0.1, 0.2, 0.4 0.5, 0.55 Amps) | 1 m Amp to 1 Amp (preferably 0.1, 0.2, 0.4 0.5, 0.55 Amps) |
| Frequency of electrical pulse bursts (each burst contains one or more pulses) | 1 Hz to 500 Hz (preferably 5 to 30 Hz, more preferably 5 to 15 Hz) | 1 Hz to 500 Hz (preferably 5 to 30 Hz, more preferably 5 to 15 Hz) | 1 Hz to 500 Hz (preferably 5 to 30 Hz, more preferably 5 to 15 Hz) | 1 Hz to 500 Hz (preferably 5 to 30 Hz, more preferably 5 to 15 Hz) |
| Number of pulses in each burst | 1 to 20 | 1 to 20 | 1 to 20 | 1 to 20 |
| Ramping | No ramping (all pulses are equal in amplitude), ramping up (first pulse is less than the last pulse in the burst), ramping down (first pulse is more than the last pulse in the burst) | No ramping (all pulses are equal in amplitude), ramping up (first pulse is less than the last pulse in the burst), ramping down (first pulse is more than the last pulse in the burst) | No ramping (all pulses are equal in amplitude), ramping up (first pulse is less than the last pulse in the burst), ramping down (first pulse is more than the last pulse in the burst) | No ramping (all pulses are equal in amplitude), ramping up (first pulse is less than the last pulse in the burst), ramping down (first pulse is more than the last pulse in the burst) |

TABLE 2-continued

| Pulse Burst Characteristics | | | | |
|---|---|---|---|---|
| Shape of each pulse in the pulse burst | Square, Trapezoidal, Sinusoidal | Square, Trapezoidal, Sinusoidal | Square, Trapezoidal, Sinusoidal | Square, Trapezoidal, Sinusoidal |
| Generated EMF field over the surface area of the coil and extending outward from the surface of the coil in a range of 0 mm to 20 mm | 1 microTesla to 10 milliTesla | 1 microTesla to 10 milliTesla | 1 microTesla to 10 milliTesla | 1 microTesla to 10 milliTesla |

Controller Software

In one embodiment, each of the treatment systems disclosed herein, including the coils, coil arrays, and controller circuit configured to generate and deliver electrical current to the coils and coil arrays, are controlled, directly or indirectly, by a software application configured to be installed and execute on a separate computing device, such as a mobile phone, laptop, or external controller, that is in wired or wireless communication with the controller circuit.

In one embodiment, the software application, or controller application, is configured to identify a type of coil system being used by a patient. Operationally, the controller application may be installed on a mobile phone and be configured to use a camera functionality of the mobile phone to capture a bar code, QR code, or other identification or be configured to generate a graphical user interface to receive an alphanumeric identifier of the coil system. Based on the data provided, the controller application may 1) validate the coil system as being a legitimate, authorized, or otherwise acceptable coil system, 2) determine what type of coil system is being used and whether that coil system is specific to a particular anatomical region, e.g. a coil system specific to a neck region, torso region, back region, leg region, foot region, arm region, head region, or other anatomical region, and 3) based upon that determination, generate graphical user interfaces that display anatomical regions specific to the coil system being used, e.g. if the coil system is specific to a neck region the generated graphical user interfaces visually display a neck, if the coil system is specific to a torso region the generated graphical user interfaces visually display a torso, if the coil system is specific to a back region the generated graphical user interfaces visually display a back region, if the coil system is specific to a leg region the generated graphical user interfaces visually display a leg region, if the coil system is specific to a foot region the generated graphical user interfaces visually display one or more feet, if the coil system is specific to an arm region the generated graphical user interfaces visually display one or more arms, and if the coil system is specific to a head region the generated graphical user interfaces (GUIs) visually display a head region.

In one embodiment, the generated GUIs are configured to receive an input from a patient as to a locus or loci of pain relative to the displayed anatomical region. For example, upon displaying the anatomical region in a GUI, a patient may paint, using a stylet or finger pressed upon a display, an area of the anatomical region that may be in pain. One or more GUIs may then be presented to prompt from a patient, and receive from the patient, an indication of the level of the pain via, for example, a visual analog scale where a user may indicate using numbers or icons a degree of the pain.

Based upon the highlighted anatomical region and the level of pain, the controller software determines 1) a desired level of magnetic flux to be delivered, 2) a corresponding set of coils to be energized in what order and at what frequency, and 3) a level of current to be delivered to each coil or coil array to generate the desired level of magnetic flux in the right location and at the right frequency. In particular, different locus or loci of pain may require an increased or decreased intensity or frequency of magnetic flux to be delivered at nerves located upstream or downstream from the locus or loci of pain. The controller software therefore comprises programmatic instructions, and supporting data, that correlates anatomical locations of pain with nerve areas that are co-located with the locus or loci of pain, upstream from the locus or loci of pain and/or downstream from the locus or loci of pain. In one embodiment, the controller software becomes aware of the location of specific coils or coil arrays based on at least one of 1) a preset relationship of the coils/coil arrays that is stored and known to the controller software based on identifying the type of coil system or 2) input by a user that indicates to the controller software where each of the coils are being positioned on a patient—such an indication being provided through a GUI that presents possible anatomical locations either through text or graphically.

In one embodiment, the software application, or controller application, is configured to generate instructions that, when communicated to and executed by the controller circuit, causes the controller circuit to generate electrical current and deliver that electrical current to different coils and/or coil arrays based on the desired frequency, intensity level, order, and location, as described above. For example, if a patient is suffering from acute pain on top of his or her right foot, the controller software may determine that coil arrays positioned on top of his or her right foot need to generate a magnetic flux in a range of 100 microTesla at a frequency of 10 Hz while coils positioned in the sole of the footwear, proximate the bottom of the patient's foot, need only be activated to generate a magnetic flux in a range of 20 microTesla at a frequency of 30Hz.

In another embodiment, the controller circuit may be configured to electrically connect with a coil array or coils and upon making such a connection, to detect and store an identifier of the coil array or coil. The controller circuit preferably stores each of the identifiers and communicates it to the controller software upon connecting. These identifiers may be further used to identify the validity and/or type of coils or coil arrays being used.

To determine desired dosing levels, in another embodiment, the controller software may include a set of programmatic instructions for dose training. In one embodiment, the controller software operates in a training mode in which 1)

a user is prompted to provide real-time feedback on pain levels using a visual analog scale, 2) the controller software modulates, over predefined periods of time, the frequency of pulse signals, the amount of current (and therefore magnetic flux intensity level) and/or the shape of the pulse signals in various combinations over the predefined period of time, and 3) as the parameters change, the user is prompted to input feedback on pain levels through the visual analog scale. For example, once a user identifies a locus of loci of pain, it initiates a cycling process starting with a set of frequency and modulating the current level and therefore the magnetic flux level up and down, prompting the user for feedback on pain levels during the cycling process. The controller software may then change frequency settings and repeat the up and down modulation of current level and magnetic flux level, again concurrently prompting the user for feedback on pain levels during the cycling process. Once the cycling processes are completed, the controller software analyzes the user's feedback to determine an optimal combination of frequency and current level for a given locus or loci of pain.

In another embodiment, the controller may be programmed by a) inputting data into a separate computing device configured to execute a set of programmatic instructions that, when executed by the separate computing device, generate a display for prompting a user to input data indicative of a desired type of treatment, wherein the desired type of treatment includes at least one of relaxation, improved sleep or sleep assist (which assists a user in falling asleep), mediation assist (which assists a user into getting into a meditative state), improved memory, weight loss, or improved mental acuity, b) wirelessly transmitting the inputted data to the controller, c) receiving, in the controller, the inputted data and generating an electrical pulse train having a frequency based on the data indicative of the desired type of treatment, d) delivering the generated electrical pulse train to each of the plurality of planar microcoil arrays, and e) automatically terminating the electrical pulse train after a programmed time period elapses, wherein the programmed time period is based on the data indicative of the desired type of treatment. Alternatively, the controller may comprise a switch (which could be a button, slide switch, or any physical input means), where a position of the switch is representative of a desired type of treatment, where the desired type of treatment includes at least one of relaxation, improved sleep or sleep assist (which assists a user in falling asleep), mediation assist (which assists a user into getting into a meditative state), improved memory, or improved mental acuity, and where the controller is adapted to generate an electrical pulse train having a frequency based on the position of the switch, to deliver the generated electrical pulse train to each of the plurality of planar microcoil arrays, and to automatically terminate generating the electrical pulse train after a programmed time period elapses.

In another embodiment, referring to FIGS. 33A-33D, the software program is configured to generate a plurality of graphical user interfaces. A first graphical user interface 3310 visually presents a first area 3311 which would visually identify or present a last program, treatment or experience that the user programmed the device with and a second area 3323 that shows all the available programs, treatments, or experiences the user can choose from, such as a relaxation program, meditation program, pain relief program, sleep improvement program, memory improvement program, or sinus decongestion program. It should be appreciated that a plurality of other programs may be listed directed to treating any of the conditions listed in this specification or to treating any of the symptoms of the conditions listed in this specification. Each listed program 3323 has a play icon that, when triggered, leads to a second graphical user interface 3330. Referring to 3320, a continuation of the first graphical user interface 3310 is shown with a third area 3325 directed to a listing of custom experiences, programs or treatments. In one embodiment, the software program provides the user with the option of customizing his or her own treatment through, for example, pressing on an icon in the home menu 3302 or an icon option 3337 in the second graphical user interface 3330. When the customization feature is activated, a third graphical user interface 3340 is displayed which provides a user with the ability to name the program 3341, adjust the amount of time the therapy would run 3343, adjust the intensity or level of current sent to the microcoils (and therefore the strength of the magnetic field generated) 3345, and/or adjust the frequency of the magnetic field pulse 3347, and, finally, save the new program 3349. While slider bars are shown as the user input mechanism, one of ordinary skill in the art would appreciate that any other mechanism may be used, including dialog boxes, wheels, visual icons or any other input techniques. Once the customized program is saved, it appears in the third area 3325. Referring back to the first graphical user interface 3310, 3320, when a program 3323 play button is pressed, whether that program is in the second 3323 or third 3325 area, it leads to the second graphical user interface 3330. There, the user may choose to program the controller by pressing icon 3335. The type of program 3331 and duration, or other descriptive information about the treatment program, 3333 is also displayed.

It should be appreciated that, preferably, the controller and the software program are already in wireless communication through, for example, a Bluetooth connection, and the connected state of the controller is actively displayed 3321. Further, it should be appreciated that after the software successfully programs the controller with a new treatment therapy, the controller or software program automatically terminates the Bluetooth connection, the Bluetooth transceiver component integrated into the controller goes into hibernation such that it does not emit any wireless frequencies during the treatment session, and, after the treatment session is complete, the controller is configured to awaken the Bluetooth transceiver to initiate communicate with the software program again. This would enable the software program to receive accurate data from the controller such as length of actual use and compare it with the chosen treatment session.

In an additional embodiment, the software program provides a recommendation, in the form of a notification when the user changes the time period or selects a treatment program, based on the user's age. Specifically, if a user is older than a threshold age, e.g. an age in the range of 50 to 100 or any increment therein or, more specifically, older than 60, the software program will generate a visual notification, warning, or recommendation that the treatment time should be longer than an average or standard treatment time. Therefore, if a standard or average treatment time is 30 minutes and the user is over 60 years old, the software will generate a graphical user interface informing the user that he or she should operate the device for a longer period of time, such as 1 hour. In another embodiment, the software program automatically recommends an experience or treatment program, as described above, that is longer than the average treatment if the person is older in age. Therefore, the software will recommend a treatment time that is shorter for younger people (i.e. younger than a threshold age in a range of 50-100) and longer for older people (i.e. older than that same threshold age).

Integration of Planar Microcoils with Clothing

To improve patient compliance and provide for ease of use, the patches comprising planar microcoil arrays are integrated into clothing. Referring to FIGS. 11A to 11E and 12A to 12E, the patches 1105, 1205 are sandwiched between a first outer layer and a second inner layer (closer to body) where the second layer is the same material as the first layer but thinner or is of a different material and thicker or thinner than the first layer. The patches are connected to a controller strip 1115, 1215 positioned at the base of the shirt (11A, 12A), top of the socks (11B, 12B), the base of a mask or neck covering (11C, 12C), top of pants (11D, 12D), or base of a glove (11E, 12E). Preferably, the controller comprises a rechargeable battery. Alternatively, the patches may be connected to a docking station to which a controller may be removably attached, as described above.

It should be appreciated that the array sizes may be variable. For example, as shown in each of the FIGS. 12A to 12E, one may have a plurality of planar microcoils integrated onto a small substrate surface area 1207, i.e. in a range of 0.5 $in^2$ to 2 $in^2$, or onto a larger substrate surface area 1209, i.e. in a range of 2.01 $in^2$ to 120 $in^2$. The smaller substrate surface areas 1207 are designed to be positioned near crevices, curves, or other non-planar anatomical areas of the patient, such as the areas in or around the toes. The larger substrate surface areas 1209 are designed to be positioned on substantially planar surface areas, such as portions of the arms, legs, and back.

It should further be appreciated that the planar microcoil arrays are preferably integrated into a layer of the clothing and are not directly exposed to the user's skin or to the outside environment. Referring to the shirt, head covering, foot covering, and hand coverings shown in FIGS. 12A-12E and further including elbow, knee, leg, ankle, shoulder, or neck braces made from materials ranging from polyester to Lycra or spandex, the planar microcoil arrays and associated traces may be incorporated into a layer positioned between an innermost layer of clothing, which touches the user's skin, and an outermost layer of clothing, which is exposed to the outside environment.

Footwear

In one embodiment, the present invention is directed toward the integration of coils and/or coil arrays into footwear, such as a shoe, boot, sock, or other foot covering. The sole or base of the footwear 1401 comprises a plurality of individual coils, such as Coil $S_1$, Coil $S_2$, and Coil $S_3$, and/or coil arrays, such as Array $S_1$ that are distributed on a surface of the sole or base. The individual coils, such as Coil $S_1$, Coil $S_2$, and Coil $S_3$, and/or coil arrays, such as Array $S_1$ may be of the type described herein or 1. Coil $S_1$: 6 by 5 cm, inner air core: 0.2 by 1.2 cm, 800 to 1,500 turns (preferably 1200-1300 turns), 0.04 mm wire thickness or larger.
2. Coil $S_2$: 7 by 5.1 cm, inner air core: 0.2 by 2.3 cm, 800 to 1500 turns (preferably 1200-1300 turns), 0.04 mm wire thickness or larger.
3. Coil $S_3$: 3 by 4.5 cm, inner air core: 0.2 by 1.7 cm, 700 turns, 0.04 mm wire thickness Preferably, the individual coils, such as Coil $S_1$, Coil $S_2$, and Coil $S_3$, and/or coil arrays, such as Array $S_1$ are configured to be of different sizes with Coil $S_1$ being larger or having more windings than Coil $S_2$ or Coil $S_3$ and where a distance between the Coil $S_1$, Coil $S_2$, and Coil $S_3$ is between 1 cm and 3 cm, preferably around 2 cm. Each of the Coil $S_1$, Coil $S_2$, and Coil $S_3$ are in electrical communication with the controller 1403. The controller 1403 is also in electrical communication with a plurality of coil arrays $U_1$, $U_2$, $U_3$, $U_4$, $U_5$, and/or $U_6$ 1402 that are integrated into the upper of the footwear and configured to cover the entirety of the user's foot. As discussed above, each of the coil arrays may be energized and/or controller as described above to address a user's foot pain.

Optionally, the ankle region of the footwear device may comprise two large coils which are positioned on opposing sides of the ankle region and are spaced and sized to function as Helmholtz coils.

Headwear

Figure 18A:
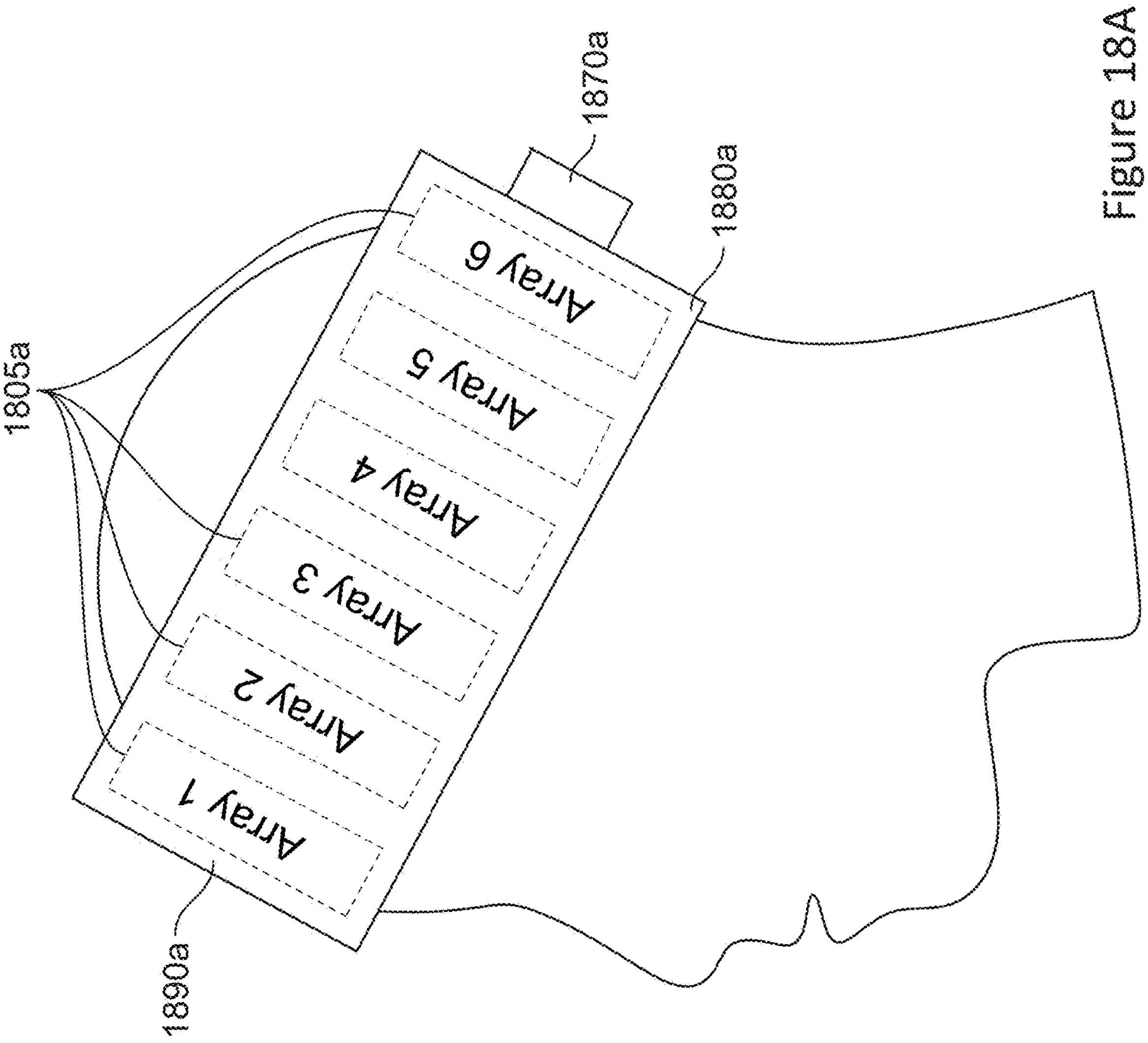
FIG. 18A is an exemplary head covering with planar microcoil arrays integrated therein.
Figure 18B:
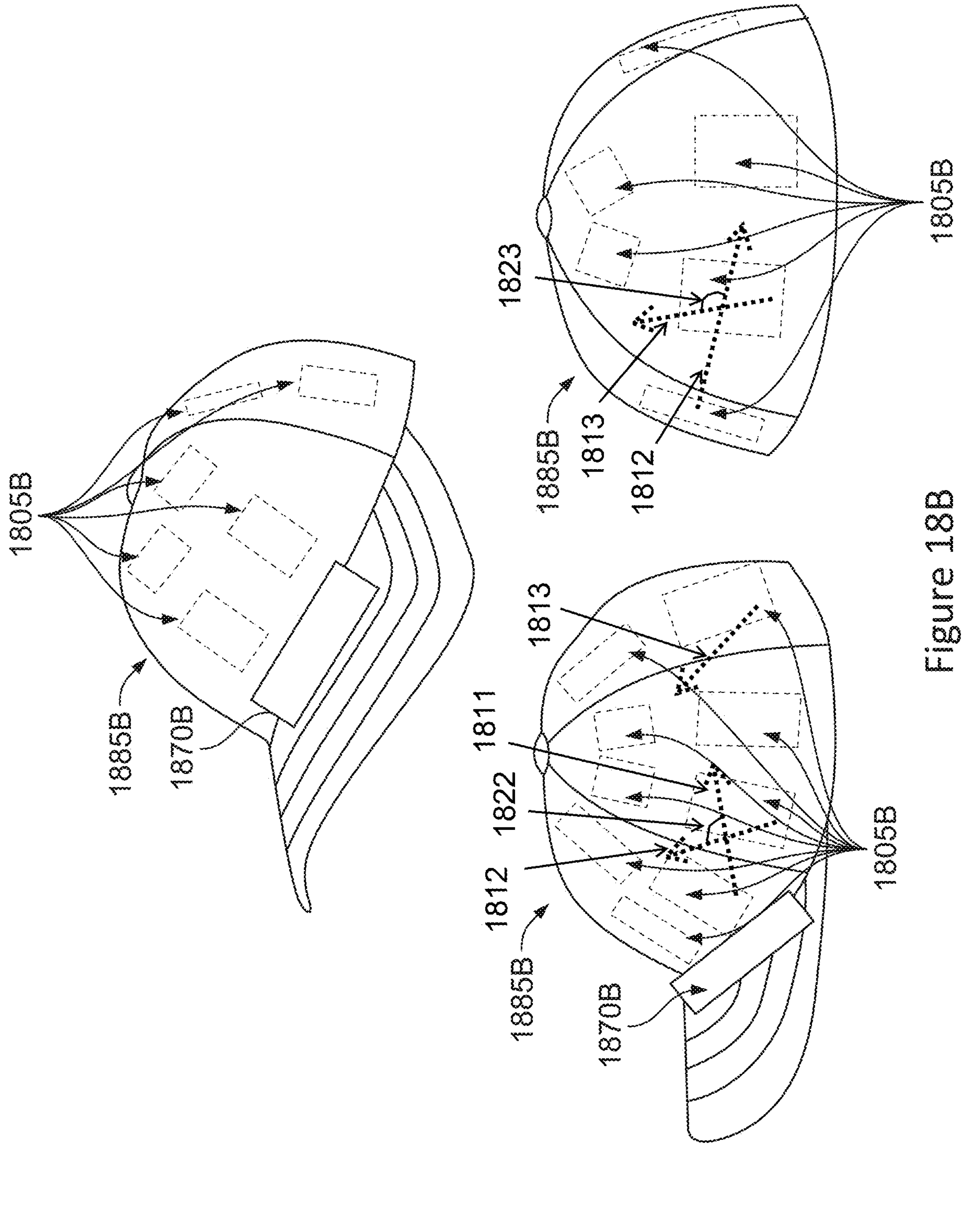
FIG. 18B is another exemplary head covering with planar microcoil arrays integrated therein.

Referring to FIG. 18A, a PEMF device 1800*a* configured to comfortably conform to a patient's head is shown. A flexible material 1880*a* configured as a headband and made out of cotton, terry cloth, polyester, or other materials. Integrated into a layer of the headband 1880*a* are a plurality of planar microcoil arrays 1805*a* which are in electrical communication with a docking station and controller 1870*a*, as described above. The headband may be adjustable by having an attachment mechanism 1890*a* which permits for the relative circumferential extent of the headband to be adjusted. The attachment mechanism 1890*a* can use, for example, a Velcro connection which can thereby adjust to the size of the user's head. Preferably there are enough planar microcoil arrays to extend along the template region of the user's head. More preferably there are enough planar microcoil arrays to extend along the entire circumferential extent of the headband.

In another embodiment, referring to FIG. 18B, a plurality of planar microcoil arrays 1805*b* is positioned in distributed positions around headwear 1885*b*, shown as a cap. It should be appreciated that, while the headwear 1885*b* is shown as a baseball cap, it may also be any of form of headwear, including a head scarf, cowboy hat, fedora hat, sun hat, flat cap hat, newsboy hat, trilby hat, pork pie hat, homburg hat, bowler hat, panama hat, western hat, stockman hat, watch cap, trapper hat, Stormy Kromer® hat, astrakhan hat, hijab scarf, beanie hat, beret hat, bucket hat, cloche hat, cocktail hat, deerstalker hat, cocktail hat, fascinator hat, gatsby hat, visor, or pillbox hat or any other configurations of material adapted to cover portions of a person's skull, including at least one or more (or preferably two or more) of the frontal bone, sphenoid bone, coronal suture, parietal bone, squamous suture, lambdoid suture, occipital bone and/or temporal bone (collectively referred to as headwear).

In one embodiment, the plurality of planar microcoil arrays 1805*b* are positioned about the crown of the headwear 1885*b* such that, when worn, at least one of the plurality of planar microcoil arrays 1805*b* is externally positioned proximate at least one or more of the frontal bone, sphenoid bone, coronal suture, parietal bone, squamous suture, lambdoid suture, occipital bone and/or temporal bone of the wearer's skull. In another embodiment, the plurality of planar microcoil arrays 1805*b* are positioned about the crown of the headwear 1885*b* such that, when worn, at least one of the plurality of planar microcoil arrays 1805*b* is externally positioned proximate at least two or more of the frontal bone, sphenoid bone, coronal suture, parietal bone, squamous suture, lambdoid suture, occipital bone and/or temporal bone of the wearer's skull.

As discussed above, it is preferred that the planar microcoils integrated into the same array are positioned in the same plane relative to the user's brain. A single array has a plurality (2 or more) discrete planar microcoils embedded into the same substrate and configured such that the plurality of discrete planar microcoils (which are serially energized or energized in parallel) are in the same plane relative to the user's brain surface, where that same plane does not intersect or pass through the user's brain surface. This enables the discrete fields created by each of the separate and discrete coils to predictably combine over a distance to yield the preferred magnetic field profile and is more preferable than other configurations such as 2 or more discrete magnetic field emitters positioned in different planes or 2 or more discrete magnetic field emitters positioned in a plane that intersects through the user's brain surface. This approach, where the Z axis of the microcoils is directed perpendicular to the user's anatomical surface, is also preferred relative to emitters that encircle the user's brain, where the Z axis of the emitter coil is parallel with a longitudinal axis passing through the height of the user.

In another embodiment, the plurality of planar microcoil arrays 1805*b* are positioned about the crown of the headwear 1885*b* such that, when worn, at least one of the plurality of planar microcoil arrays 1805*b* is externally positioned proximate at least the frontal bone and the parietal bone of the wearer's skull. In another embodiment, the plurality of planar microcoil arrays 1805*b* are positioned about the crown of the headwear 1885*b* such that, when worn, at least one of the plurality of planar microcoil arrays 1805*b* is externally positioned proximate at least the frontal bone and the parietal bone and at least one of the sphenoid bone and/or temporal bone of the wearer's skull.

In another embodiment, the plurality of planar microcoil arrays 1805*b* are positioned such that they are symmetrically distributed about the crown of the headwear 1885*b* such that, when worn, at least one of the plurality of planar microcoil arrays 1805*b* is externally positioned proximate a left side of the wearer's frontal bone, at least one of the plurality of planar microcoil arrays 1805*b* is externally positioned proximate a right side of the wearer's frontal bone, at least one of the plurality of planar microcoil arrays 1805*b* is externally positioned proximate at a top side of the wearer's parietal bone, at least one of the plurality of planar microcoil arrays 1805*b* is externally positioned proximate a left side of the wearer's parietal bone, and at least one of the plurality of planar microcoil arrays 1805*b* is externally positioned proximate a right side of the wearer's parietal bone.

In another embodiment, the plurality of planar microcoil arrays 1805*b* is positioned such that they are symmetrically distributed about the crown of the headwear 1885*b* such that, when worn, at least two of the plurality of planar microcoil arrays 1805*b* are externally positioned proximate the wearer's frontal bone and at least three of the plurality of planar microcoil arrays 1805*b* are externally positioned proximate the wearer's parietal bone. In another embodiment, the plurality of planar microcoil arrays 1805*b* is positioned such that they are symmetrically distributed about the crown of the headwear 1885*b* such that, when worn, at least four (and preferably between 4 and 10) of the plurality of planar microcoil arrays 1805*b* are externally positioned proximate at least the wearer's frontal bone and the wearer's parietal bone and optionally the temporal bone and occipital bone.

In another embodiment, the plurality of planar microcoil arrays 1805*b* is positioned such that one or more arrays are a) positioned between the front of the crown of the headwear 1885*b* and the right and/or left frontal lobe, b) positioned between the right side of the crown of the headwear 1885*b* and the right temporal lobe, c) positioned between the left side of the crown of the headwear 1885*b* and the left temporal lobe, d) positioned between the top side of the crown of the headwear 1885*b* and the cerebral cortex, e) positioned between the top side of the crown of the headwear 1885*b* and the parietal lobe, and/or f) positioned between the back side of the crown of the headwear 1885*b* and the occipital lobe.

Figure 25B:
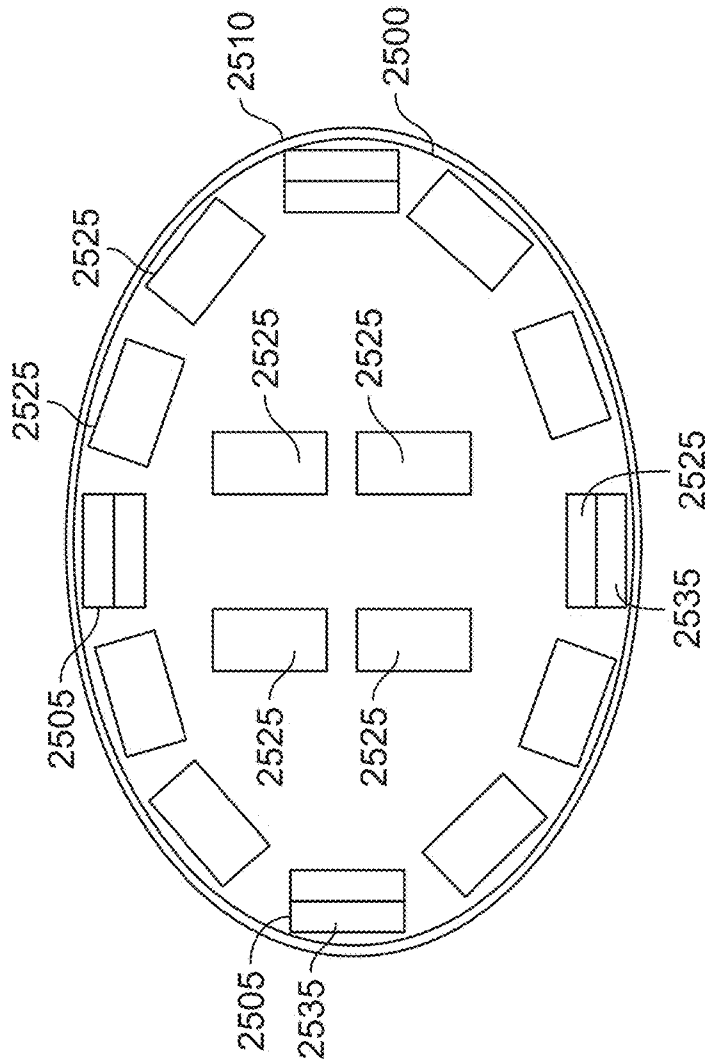
FIG. 25B shows a second view of an exemplary liner configured to be positioned between headwear and a patient's head.
Figure 25A:
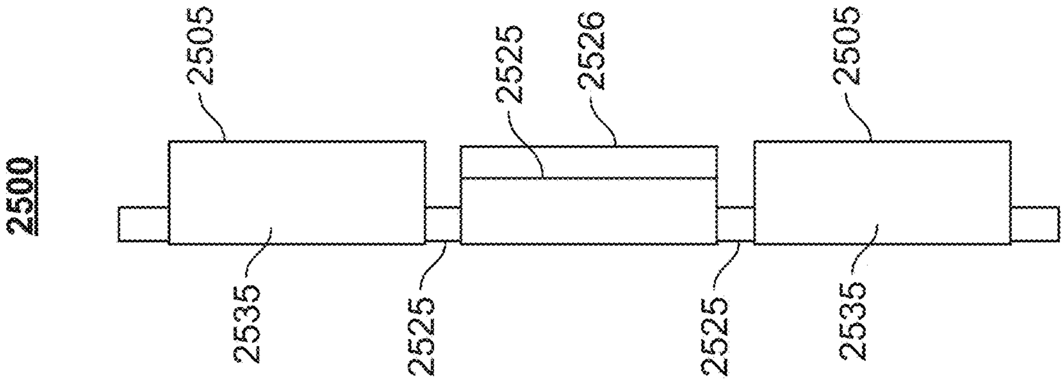
FIG. 25A shows a first view of an exemplary liner configured to be positioned between headwear and a patient's head.

Referring to FIGS. 25A and 25B, in another embodiment, the plurality of planar microcoil arrays are integrated into a liner 2500 having a plurality of cells 2505 wherein each cell is defined by a protrusion from a base material 2525 extending toward a patient's head and where the base material positioned between cells comprises plastic, cardboard, or other rigid non-metallic material to which the material covering the protrusion is attached. Within at least some of the cells, a microcoil array 2525 is positioned with the emitting coil surface 2526 directed inward toward the patient's head. Positioned behind the array is cushioning material 2535, such as cotton or foam, to keep the microcoil array in place. Preferably, there is a minimal amount of material or additional layers between the array and the patient's head. Each cell 2505 is distributed around the liner such that, when the liner is attached to the crown 2510 of the head garment and the head garment plus liner is worn, at least one cell 2505 with an array 2525 is positioned between the front of the crown 2510 of the headwear and the right and/or left frontal lobe, at least one cell 2505 with an array 2525 is positioned between the right side of the crown 2510 of the headwear and the right temporal lobe, at least one cell 2505 with an array 2525 is positioned between the left side of the crown 2510 of the headwear and the left temporal lobe, at least one cell 2505 with an array 2525 is positioned between the top side of the crown 2510 of the headwear and the cerebral cortex, at least one cell 2505 with an array 2525 is positioned between the top side of the crown 2510 of the headwear and the parietal lobe, and/or at least one cell 2505 with an array 2525 is positioned between the back side of the crown 2510 of the headwear and the occipital lobe.

More preferably, one cell 2505 with an array 2525 is positioned in the front of the crown, 2510 adjacent the frontal lobe when worn; one cell 2505 with an array 2525 is positioned in the top, forward right section of the crown 2510, adjacent the right top portion of the frontal lobe when worn; one cell 2505 with an array 2525 is positioned in the top, forward left section of the crown 2510, adjacent the left top portion of the frontal lobe when worn; one cell 2505 with an array 2525 is positioned in the top, back right section of the crown 2510, adjacent the right top portion of the parietal lobe when worn; one cell 2505 with an array 2525 is positioned in the top, back left section of the crown 2510, adjacent the left top portion of the parietal lobe when worn; one cell 2505 with an array 2525 is positioned in the right-side section of the crown 2510, adjacent the right temporal lobe when worn; one cell 2505 with an array 2525 is positioned in the left-side section of the crown 2510, adjacent the left temporal lobe when worn; and one cell 2505 with an array 2525 is positioned in the back of the crown 2510, adjacent the occipital lobe when worn. The use of a cushioned matrix of cells has several benefits, including a) providing a degree of flexibility to accommodate different sized heads and b) insuring a constant directional orientation of the array relative to the patient's head.

A controller 1870*b* is in electrical communication with each of the plurality of planar microcoil arrays 1805*b* and is programmed to direct an electrical current to each of the plurality of planar microcoil arrays 1805*b* in accordance with a certain frequency, a certain current intensity, a certain pulse width or shape, and a certain sequence, as described throughout this specification. More specifically, the controller 1870*b* directs an electrical current from an energy source, such as a battery, to each of the plurality of planar microcoil arrays 1805*b* in accordance with stored programmatic instructions. The stored programmatic instructions define a current level (preferably in a range of 5 mA to 200 mA), define a pulse shape (preferably rectangular, sinusoidal, or a flat pulse with a sloped activation and deactivation), define a pulse frequency (preferably in a range of 0.1 Hz to 200 Hz), and define a sequence of activating each of the plurality of planar microcoil arrays 1805*b* such as clockwise around the wearer's skull, counterclockwise around the wearer's skull, sequentially such that only one of the plurality of planar microcoil arrays 1805*b* has current driven thereto at one time, concurrently such that at least two of the plurality of planar microcoil arrays 1805*b* has current driven thereto at one time, concurrently such that at least three of the plurality of planar microcoil arrays 1805*b* has current driven thereto at one time, concurrently such that all of the plurality of planar microcoil arrays 1805*b* has current driven thereto at one time, concurrently such that planar microcoil arrays 1805*b* on opposing sides of the wearer's skull has current driven thereto at one time, or concurrently such that planar microcoil arrays 1805*b* separated by at least 2 inches across the wearer's skull has current driven thereto at one time.

In one embodiment, the controller 1870*b* and energy source may be integrated into the brim of the headwear 1885*b* such that the controller and energy source lay flat along a surface of the brim and largely perpendicular to the crown. By doing so, the controller 1870*b* and energy source will seamlessly integrate into the headwear 1885*b* and not be conspicuous. The controller 1870*b* and energy source may increase the thickness of the brim, but, otherwise, the brim will appear to be normal and the controller and energy source will not be visible on the crown of the headwear 1885*b*. In one embodiment, the controller 1870*b* and energy source is at least partially encased in silicone at a top surface and its bottom surface is in physical contact with the brim material, which may comprise plastic and/or fabric.

As described above, the controller is programmed to generate a magnetic field via the planar microcoil arrays by four different vectors: a) the frequency of the pulse train or burst, b) the shape of each pulse in the pulse train or burst itself, c) the relative peak intensities of each pulse in the pulse train or burst itself, and d) the degradation profile from the surface of the planar microcoil arrays. In a preferred embodiment, each embodiment described herein generates a magnetic field by:

a) Using a planar microcoil array having at least one coil positioned thereon, from 2 to 100 coils positioned thereon, and preferably from 4-10 coils where each of the coils may be one or more of the embodiments described herein;

b) Driving a current to the coils positioned on a single array where the current is in the form of a pulse train, where the pulse train may be one or more of the embodiments described herein, and, more preferably, where the pulse train may be a ramping rectangular or sinusoidal pulse having a first pulse, a first time interval, a second pulse, and optionally a second time interval and a third (or more) pulses, as follows:

a. the first pulse and second pulse (and the optional third or more pulses) have pulse widths in a range of 0.001 to 0.2 seconds and preferably in a range of 0.01 to 0.02 seconds. where the first time interval and optional additional time intervals are in a range of 0.01 to 0.04 seconds (preferably a 0.025 second interval), and where the second pulse is greater than the first pulse (or vice-versa) and have current levels in a range of 5 mA to 200 mA; or b. each pulse width may be defined as a function of the period (which is the inverse of the frequency) where each pulse width is in a range of ½ to 1/50 the period length (preferably ⅕ to ⅐ the period length), where each interval between the pulses in the pulse train is in a range of ½ to 1/50 the period length (preferably ⅕ to ⅑), where the dead time between each pulse burst or train is in a range of ½ to 1/20 the period length (preferably ⅓ to ⅕), and where the second pulse is greater than the first pulse (or vice-versa) and have current levels in a range of 5 mA to 200 mA;

c) Activating the pulse train in accordance with a programmed frequency, where the programmed frequency is in a range of 0.01 Hz to 200 Hz and preferably in a range of 1 Hz to 60 Hz; and d) Activating each of the microcoil arrays in parallel or in series (or a combination thereof) such that the peak intensity generated by each coil on the planar microcoil array concurrently, yet independently, decreases according to the following equation:

$$y = Ax^{-B}$$

where A is in a range of 100 to 600, and more preferably 300 to 400, and every whole number increment therein and where B is in a range of 1 to 2.5 (and every 0.1 decimal increment therein).

It should be appreciated that, upon activation, magnetic fields are generated in accordance with the stimulation protocols described above. Conventionally, it is believed that very large magnetic fields have to be directed into the brain to have any tangible therapeutic effects on certain conditions, such as depression. However, it is believed that, by modulating a position, configuration, orientation, or movement, of magnetite chains in one or more brain cells or neurons, which may be effectuated by magnetic fields less than 200 microTesla or by applying a sufficient magnetic field gradient, which is determined by the frequency and shape of pulse, one can cause a normalization of brain function, at least during the application of the magnetic fields. Normalization of brain function may thereby enable at least a partial alleviation of symptoms associated with sinus inflammation, sinusitis, anxiety disorders, obsessive compulsive disorder, post-traumatic stress disorder, memory degeneration, schizophrenia, attention deficient disorder, autism, Parkinson's disease, ischemic stroke treatment, stroke rehabilitation, drug addiction, including addiction to, or cravings for, nicotine, cocaine, alcohol, heroine, methamphetamines, stimulants, and/or sedatives, depression and depression-related conditions, such as post-partum depression or bipolar depression, auditory hallucinations, erectile dysfunction, improved weight management, multiple sclerosis, fibromyalgia, Alzheimer's disease, spinocerebellar degeneration, epilepsy, urinary incontinence, movement disorders, chronic pain, insomnia, vasculature degeneration or disorders, sleep disorders, memory disorders, relaxation, stress, sexual function dysfunction, chronic tinnitus, high blood pressure, or sleep apnea while the magnetic fields are being applied to the brain. Accordingly, it is within the scope of this invention to treat symptoms related to disorders having a loci of dysfunction in the brain by normalizing at least one of a position, configuration, orientation, or movement of magnetite chains in one or more brain cells or neurons by applying magnetic fields less than 200 microTesla, as measured within 1 cm from the surface of the planar microcoil surface, or by applying a sufficient magnetic field gradient.

More specifically, each of the conditions listed in this specification may be treated by having a patient wear headwear 1885b and be subjected to magnetic fields that help entrain the frequency and/or magnitude of brain waves. In one embodiment, a software program configured to execute on a mobile device, as further described herein, is adapted to generate one or more graphical user interfaces. The one or more graphical user interfaces is configured to receive data inputted from a wearer, wherein the data is indicative of a health state of the wearer. The graphical user interfaces preferably prompts the wearer to input data indicative of whether the wearer:

1. Has one or more contraindications of use, including having had a seizure, headache or migraine within the last 48 hours, having a history of seizures, having ferromagnetic or metallic material in or around his or her head;
2. Suffers from one or more conditions that may be contraindicated by the use of pulsed electromagnetic field therapy; and
3. Wishes to have the degree of intensity of the treatment be set to one or more levels, such as mild, medium, strong or very strong.

Figure 23:
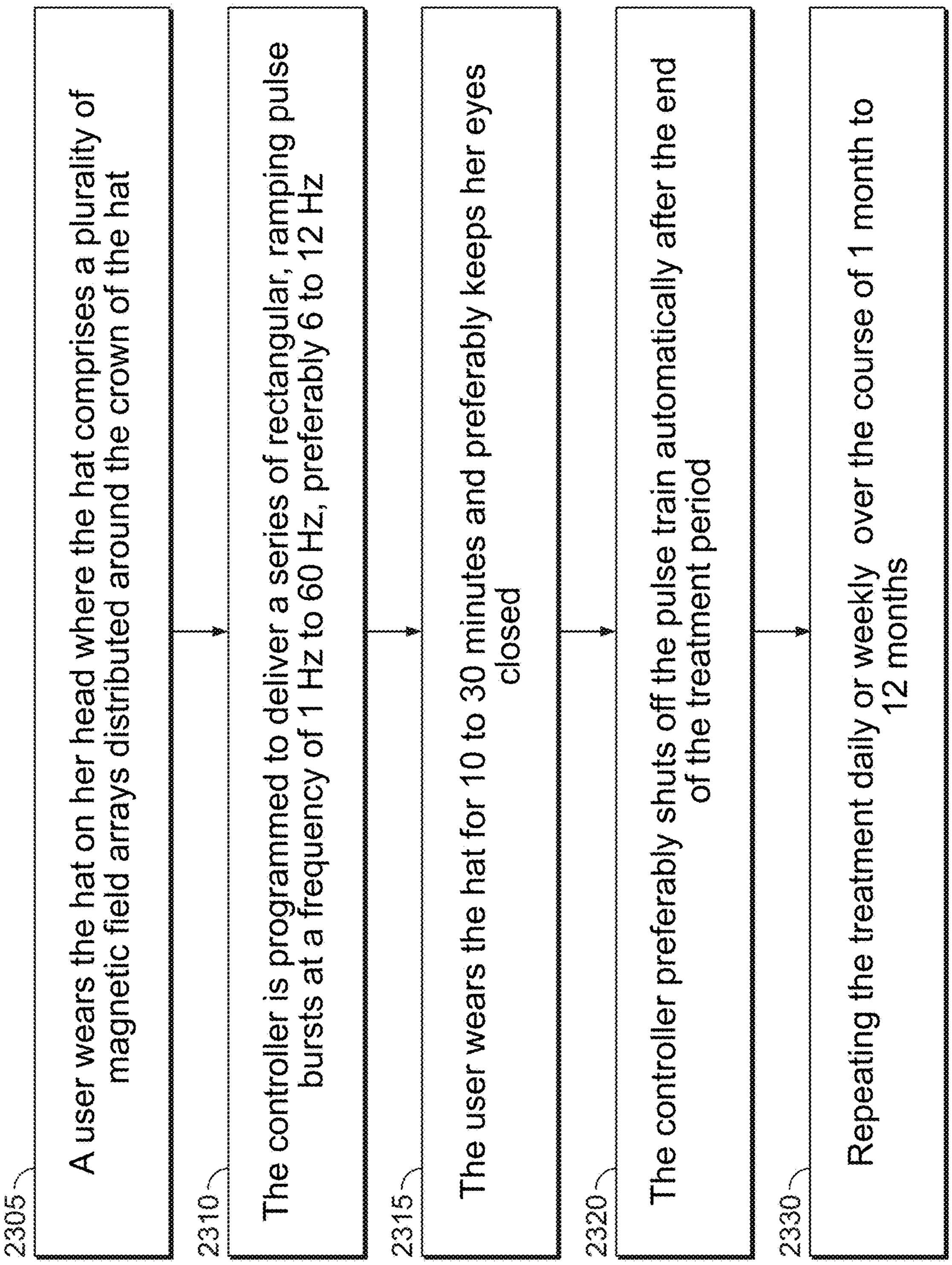
FIG. 23 shows an exemplary method of treating a person's brain.
Figure 24:
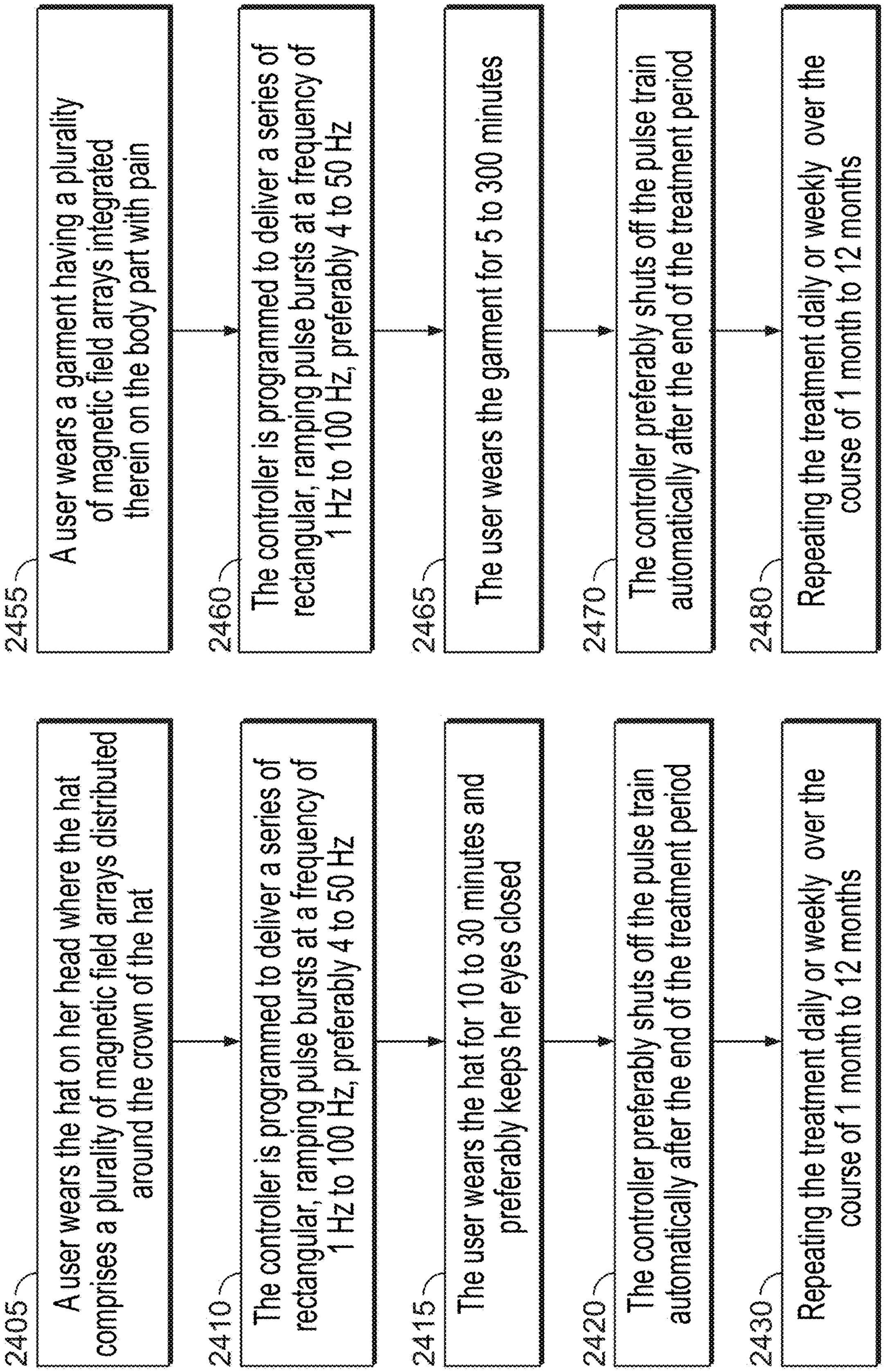
FIG. 24 shows an exemplary method of treating pain in various parts of a person's body.

Based on the data inputted above, the software program configured to execute on the mobile device is adapted to generate a plurality of programmatic instructions that define one or more of a current level, a pulse shape, a pulse frequency, and/or a selection of, or sequence of, which microcoil arrays actually receive the current. The programmatic instructions are adapted to be transmitted, whether by a wired connection or wirelessly, to the controller integrated into the headwear 1885*b* and the controller is adapted to modify the generation and transmission of current in accordance with the plurality of programmatic instructions that define one or more of a current level, a pulse shape, a pulse frequency, and/or a selection of, or sequence of, which microcoil arrays actually receive the current. Exemplary combinations of current level, pulse shape, pulse frequency, and/or a selection of, or sequence of, which microcoil arrays actually receive the current are provided below:

1. Referring to FIG. 23, in one embodiment, any of the aforementioned conditions may be treated by placing a hat, as described above, on a user's head 2305, programming the controller to deliver a series of rectangular, ramping pulse bursts at a frequency of 1 Hz to 60 Hz, preferably 6 to 12 Hz 2310, wear the hat for 10 to 30 minutes (preferably with eyes closed, blocking out auditory stimulus, and/or taking deep breaths) 2315, having the controller shut off the pulse train automatically after the treatment period 2320, and repeating the process daily or weekly over several months 2330. In one embodiment, this treatment causes the user's brain to decrease or increase alpha wave generation, to increase blood circulation, decrease or increase beta wave generation, to decrease or increase delta wave generation, to decrease or increase theta wave generation, to decrease or increase gamma wave generation, to increase coherence in theta wave generation, to increase coherence in delta wave generation, to increase coherence in alpha wave generation, to increase coherence in beta wave generation, to increase coherence in gamma wave generation, and/or any combination of the above.
2. Referring to FIG. 24, in one embodiment, chronic pain, peripheral neuropathy, in a person's feet, legs, back, chest, torso, arms, hands, shoulders, or any other body part other than the person's head can be treated by a) placing a hat, as described above, on a user's head 2405, programming the controller to deliver a series of rectangular, ramping pulse bursts at a frequency of 1 Hz to 100 Hz, preferably 4 to 50 Hz 2410, wear the hat for 10 to 30 minutes (preferably with eyes closed, blocking out auditory stimulus, and/or taking deep breaths) 2415, having the controller shut off the pulse train automatically after the treatment period 2420, and repeating the process daily or weekly over several months 2430 while concurrently, or partially concurrently, b) placing another piece of clothing with integrated microcoil arrays, as described herein, on the portion of the user's body with pain 2455, programming the controller to deliver a series of rectangular, ramping pulse bursts at a frequency of 1 Hz to 100 Hz, preferably 4 to 50 Hz 2460, wear the hat for 5 to 300 minutes 2465, having the controller shut off the pulse train automatically after the treatment period 2470, and repeating the process daily or weekly over several months 2480. In one embodiment, this treatment causes the user's brain to increase blood circulation, decrease or increase alpha wave generation, to decrease or increase beta wave generation, to decrease or increase delta wave generation, to decrease or increase theta wave generation, to decrease or increase gamma wave generation, to increase coherence in theta wave generation, to increase coherence in delta wave generation, to increase coherence in alpha wave generation, to increase coherence in beta wave generation, to increase coherence in gamma wave generation, and/or any combination of the above while concurrently causing in the other body part with pain a decrease in the level of pain and/or increasing blood circulation.

The headwear embodiment disclosed herein may be used to treat Parkinson's disease by applying the stimulation protocols, using the hat and integrated planar microcoils, described above to direct magnetic fields toward the substantia nigra of a patient. In one embodiment, a patient with Parkinson's disease may be treated by placing a hat, as described above, on a user's head, programming the controller to deliver a series of pulses (preferably rectangular, ramping pulse bursts) at a frequency of 0.1 Hz to 60 Hz, preferably 0.1 to 50 Hz 2310, wear the hat for 10 to 30 minutes (preferably with eyes closed, blocking out auditory stimulus, and/or taking deep breaths), having the controller shut off the pulse train automatically after the treatment period, and repeating the process daily or weekly. In one embodiment, this treatment causes the user's brain to decrease or increase alpha wave generation, to increase blood circulation, decrease or increase beta wave generation, to decrease or increase delta wave generation, to decrease or increase theta wave generation, to decrease or increase gamma wave generation, to increase coherence in theta wave generation, to increase coherence in delta wave generation, to increase coherence in alpha wave generation, to increase coherence in beta wave generation, to increase coherence in gamma wave generation, to modulate dopamine production in the substantia nigra and/or any combination of the above.

Figure 21A:
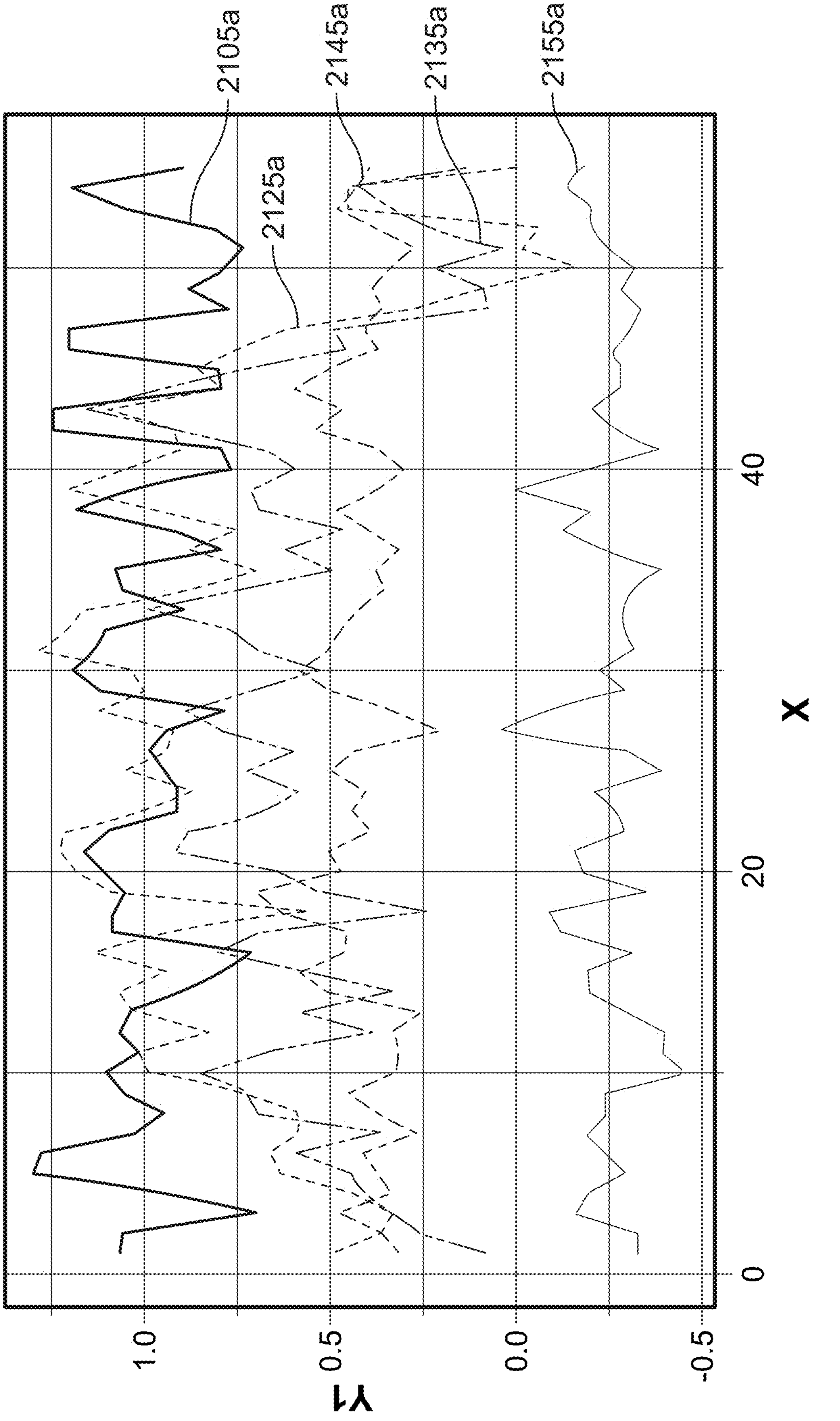
FIG. 21A shows an exemplary EEG profile of a human brain without exposure to an pulsed electromagnetic field using planar coils.
Figure 21B:
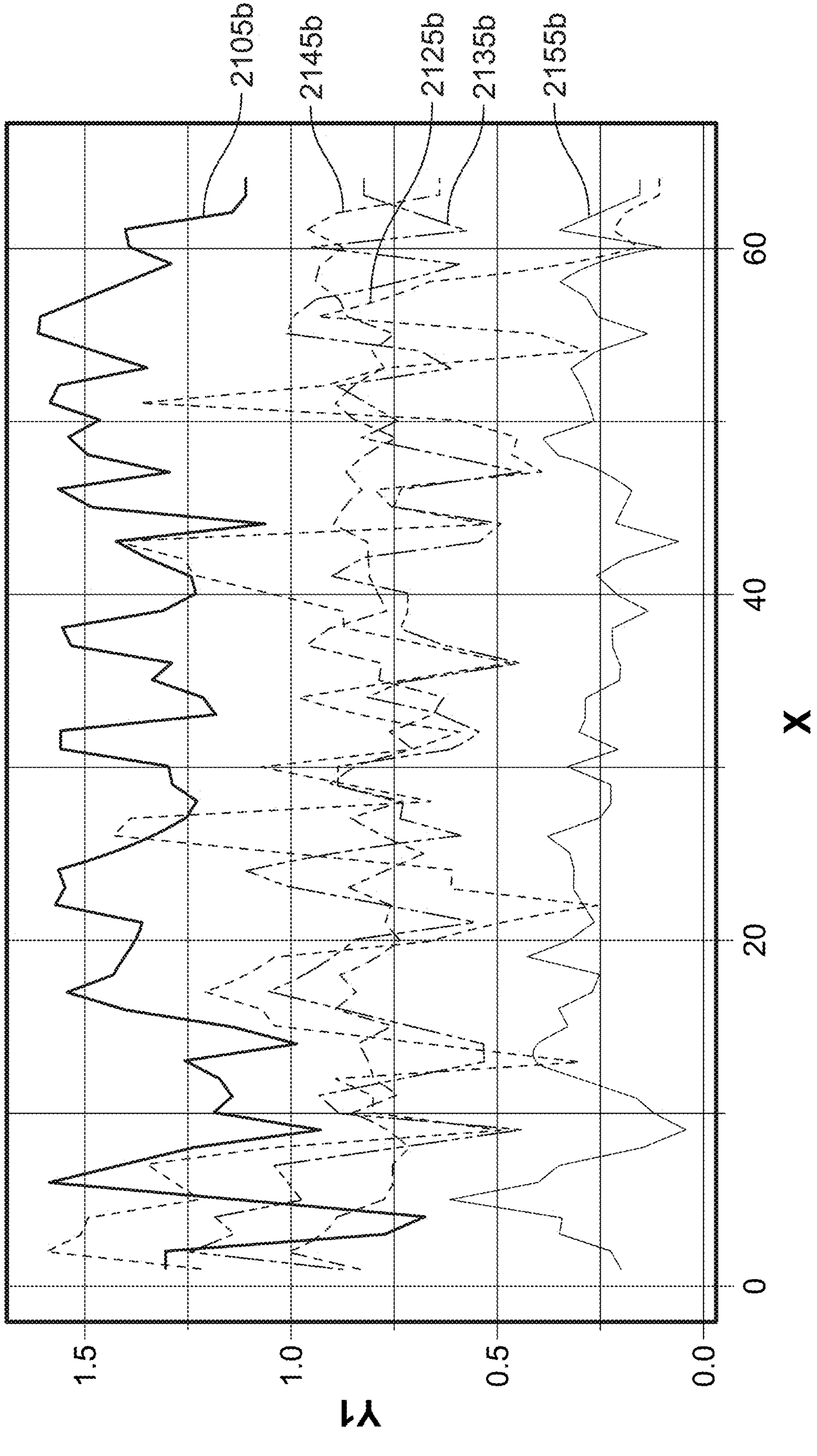
FIG. 21B shows an exemplary EEG profile of a human brain during exposure to an pulsed electromagnetic field using planar coils.

For example, referring to FIG. 21A and FIG. 21B, a first pre-treatment brainwave frequency band 2105*a* is modulated in both amplitude and frequency after treatment, as shown by a corresponding first post-treatment brainwave frequency band 2105*b*. Similarly, a second pre-treatment brainwave frequency band 2125*a* is modulated in both amplitude and frequency after treatment, as shown by a corresponding second post-treatment brainwave frequency band 2125*b*. Similarly, a third pre-treatment brainwave frequency band 2135*a* is modulated in both amplitude and frequency after treatment, as shown by a corresponding third post-treatment brainwave frequency band 2135*b*. Similarly, a fourth pre-treatment brainwave frequency band 2145*a* is modulated in both amplitude and frequency after treatment, as shown by a corresponding fourth post-treatment brainwave frequency band 2145*b*. Similarly, a fifth pre-treatment brainwave frequency band 2155*a* is modulated in both amplitude and frequency after treatment, as shown by a corresponding fifth post-treatment brainwave frequency band 2155*b*.

As part of one or more, or all, of the treatment protocols described herein, a user may be instructed, through one or more programmatic instructions executing on a separate computing device (such as a phone), to keep his or her eyes open (for pain relief, for example) or to keep his or her eyes closed (for relaxation). Different treatment objectives (i.e. treating any one of the conditions described herein) may require the user's other senses to be exposed to different amounts of stimulation. For example, depending on the treatment objective (e.g., pain vs. anxiety relief), a user may be instructed, through one or more programmatic instructions executing on a separate computing device (such as a phone), to avoid visual stimulation, to seek visual stimulation, to avoid auditory stimulation, to seek auditory stimulation, to avoid taste or smell sensations, or to seek taste or smell sensations.

In another embodiment, the present invention is directed toward treating an individual experiencing cardiac arrest or a hindering or stoppage of blood flow to the individual's brain. During cardiac arrest, blood flow decreases and global cerebral ischemia may starting occurring within 2-3 minutes, leading to brain injury and, if not addressed immediately, causing severe and irreversible brain injury. It would be beneficial to have a device that can be immediately and easily applied to a person undergoing cardiac arrest that will increase blood flow in the brain. Such a device preferably a) will not interfere with other therapies which would have to be implemented by emergency personnel when treating cardiac arrest, b) will be extremely easy and fast to apply so as to avoid distracting personnel in the treatment of cardiac arrest, c) will increase brain blood volume without potentially causing adverse side effects to other organs, and d) will help maintain an acceptable level of blood perfusion in the brain, despite decreasing blood flow to the brain due to cardiac arrest.

In this embodiment, the headwear device described herein may be used to prevent, protect against, or otherwise decrease the possibility or extent of brain injury due to blood flow decreasing, referred to as cerebral ischemia, during cardiac arrest. The application of pulsed electromagnetic fields, using the headwear described herein and programmed with the pulsing magnetic field parameters described herein, can increase cerebral blood (particularly micro-vascular) perfusion by at least 1%, preferably at least 5%, and more preferably at least by 10% relative to an individual who does not receive the applied pulsed electromagnetic fields. The application of pulsed electromagnetic fields, using the headwear described herein and programmed with the pulsing magnetic field parameters described herein, can also increase the dilation of cerebral arterioles, as measured by the diameter of one or more cerebral arterioles or an average thereof, by at least 1%, preferably at least 5%, and more preferably at least by 10% relative to an individual who does not receive the applied pulsed electromagnetic fields. The application of pulsed electromagnetic fields, using the headwear described herein and programmed with the pulsing magnetic field parameters described herein, can also increase cerebral blood oxygenation by at least 1%, preferably at least 5%, and more preferably at least by 10% relative to an individual who does not receive the applied pulsed electromagnetic fields. The application of pulsed electromagnetic fields, using the headwear described herein and programmed with the pulsing magnetic field parameters described herein, can also increase cerebral blood flow velocity by at least 1%, preferably at least 5%, and more preferably at least by 10% relative to an individual who does not receive the applied pulsed electromagnetic fields. The application of pulsed electromagnetic fields, using the headwear described herein and programmed with the pulsing magnetic field parameters described herein, can also increase cerebral blood flow volumes by at least 1%, preferably at least 5%, and more preferably at least by 10% relative to an individual who does not receive the applied pulsed electromagnetic fields.

Figure 26:
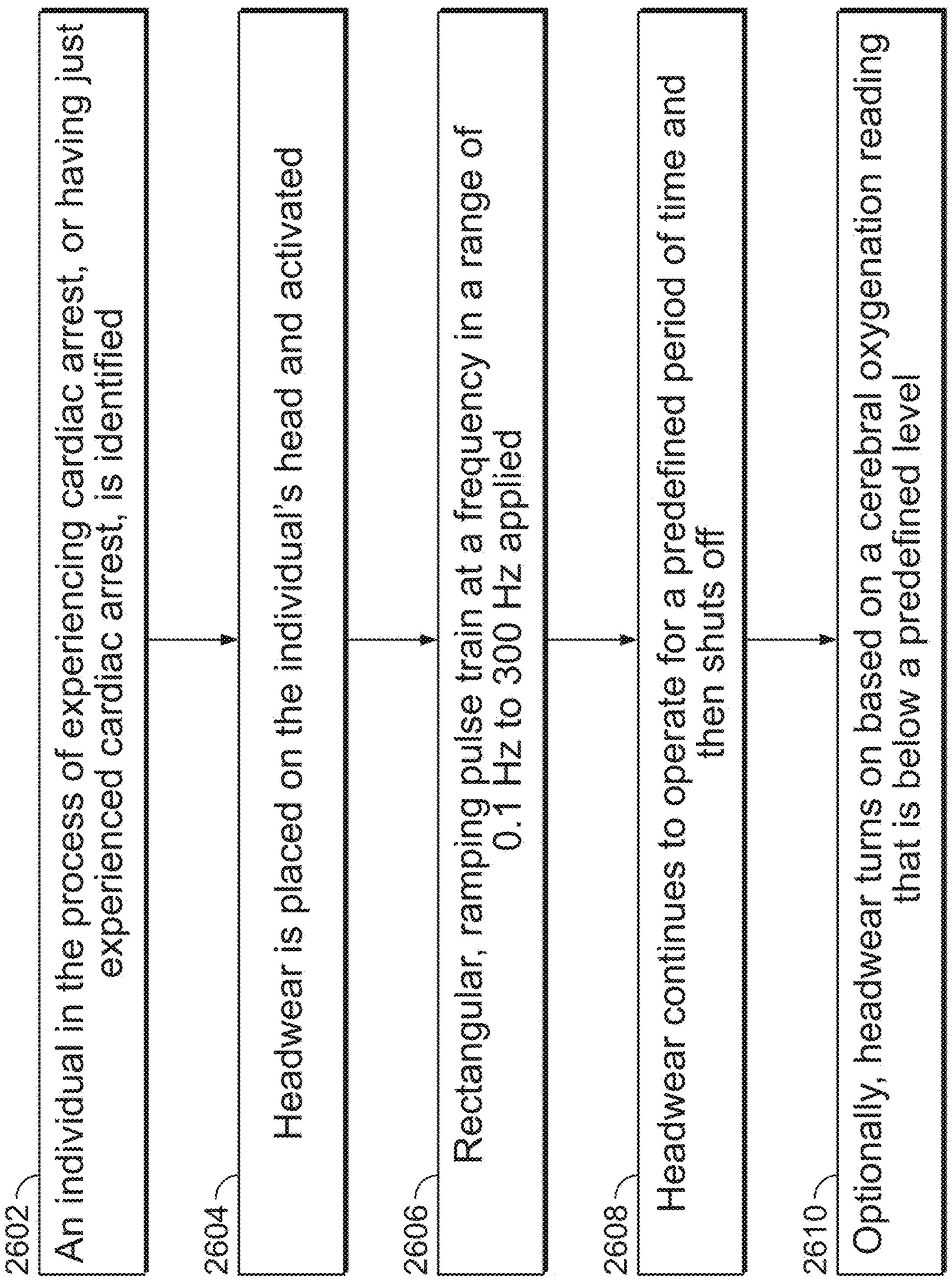
FIG. 26 shows a therapeutic process for treating an individual experiencing cardiac arrest
Figure 27B:
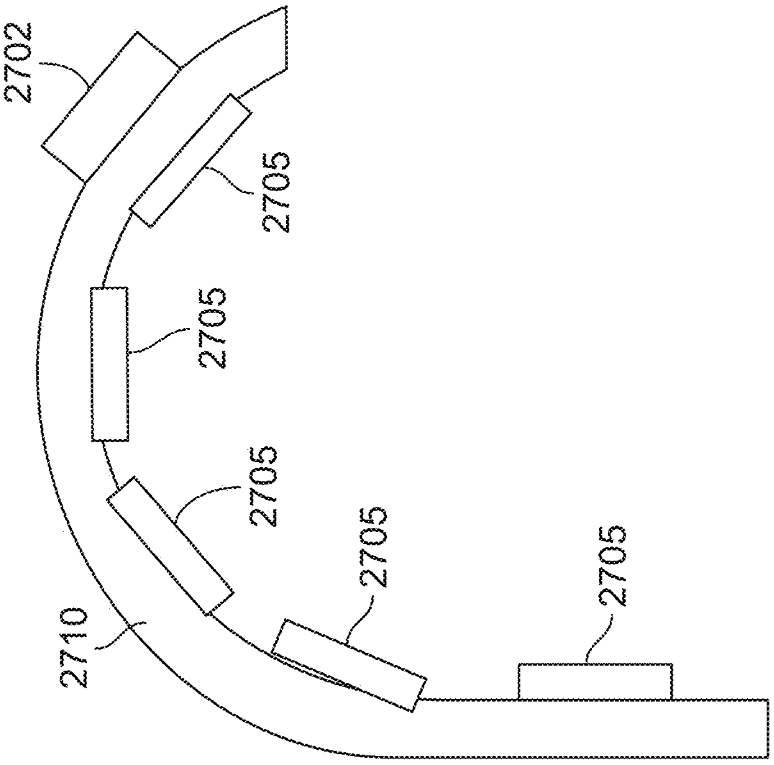
FIG. 27B shows a side view of a disposable headwear embodiment.
Figure 27A:
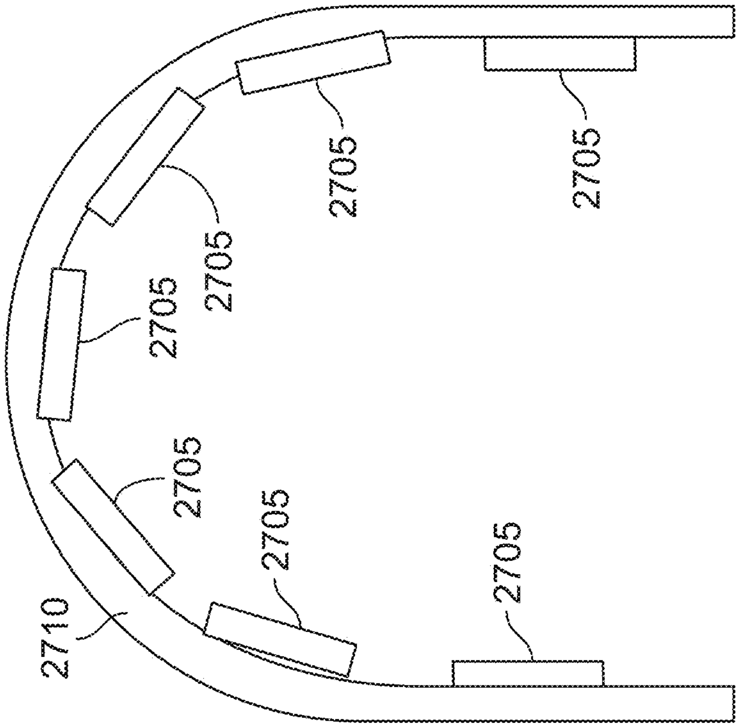
FIG. 27A shows front view of a disposable headwear embodiment.

Referring to FIG. 26, an individual in the process of experiencing cardiac arrest, or having just experienced cardiac arrest, is identified 2602. Headwear, such as the one shown in FIGS. 18A or 18B (with or without a brim), is placed on the individual's head and activated 2604. Referring to FIGS. 27A and 27B, preferably, the headwear 2700*a*, 2700*b* comprises a controller 2702 programmed to increase at least one of cerebral blood vessel dilation, cerebral blood flow volumes, cerebral tissue oxygenation, cerebral blood flow velocity, or cerebral blood perfusion using a pulse train having a plurality of rectangular ramping pulse bursts (as described elsewhere in this specification) where the pulse train is applied using a frequency in a range of 0.1 Hz to 300 Hz, and more preferably 10 Hz to 60 Hz, and where the pulse train is generated at each of a plurality of distributed microarrays 2705 sequentially, partially concurrently or fully concurrently (step 2606 in FIG. 26). In one embodiment, only the microarrays proximate the individual's frontal lobe and temporal lobes are activated and the microarrays proximate the occipital lobe are not activated. It should be appreciated that any of the programmatic parameters described in this specification may be used. In one embodiment, the headwear is a single-use, disposable device with a non-rechargeable energy source. In one embodiment, the headwear is a multi-use device with a rechargeable or changeable energy source.

Preferably the headwear continues to operate for a predefined period of time 2608 which preferably overlaps with the period during which the individual is experiencing cardiac arrest or the immediate treatment period thereafter, after which is automatically terminates based on an internal clock in data communication with the controller. The predefined period of time is from 1 minute to 10 hours, or any time increment therein, of substantially continuous use. Alternatively, the headwear may be activated and applied for a 24 hour period, or a period of time less than 24 hours, with some off periods, resulting in alternating on-periods in a range of 1 minute to 12 hours (or any time increment therein) and off-periods in a range of 1 minute to 12 hours (or any time increment therein). Optionally, the headwear may be automatically reactivated 2610 when a cerebral oxygenation reading is below a predefined level. In such an embodiment, a cerebral oxygenation monitor, such as a regional oximeter, is connected to sensors attached to one or more positions on a patient's forehead. Upon sensing the cerebral oxygenation level is below a predefined level, wherein such level may be programmed by a user, the cerebral oxygenation monitor transmits a trigger signal that would cause the headwear to re-activate. The headwear, in this case, would not have microcoil arrays positioned in the areas proximal the frontal lobe where the cerebral oxygenation sensors are located. Preferably, the headwear would integrate cerebral oxygenation sensors into the same substrate as the microcoil arrays and position the microcoil arrays around the sensors, keeping them off when the sensors are operating and keeping the sensors off when the arrays are generating magnetic fields.

Accordingly, in this embodiment, the headwear disclosed herein may be used to induce vasodilation, increase vascular blood flow velocity, increase brain tissue oxygenation, and/or increase blood volume circulation in the user's brain in order to treat, or protect against, one or more of encephalopathy, seizure, stroke, traumatic brain injury, neuronal damage or death, brain edema, blood-brain barrier damage, or hypoxic/ischemic injury to the brain. This may be of particular value during, or after, a stroke, during or after cardiac arrest, during or after a concussion, during or after a deprivation of oxygen (e.g., drowning), during a coronavirus infection. As such, an initial diagnosis of one or more of those conditions may preceded the process described in FIG. 26.

It should be appreciated that the controllers for each of the headwear embodiments may be programmed with one or more of the following treatment protocol(s), depending on the therapeutic obj ective:

1. In one embodiment, the controller may be programmed to operate at a first current intensity for a first period of time. After operating for the first period of time, the controller would shut off, terminating current flow. After a first off period, the controller may be programmed to operate at a second current intensity for a second period of time, where the second current intensity is less than the first current intensity and/or the second period of time is less than the first period of time. For example, in one embodiment, the controller is programmed to operate at a current intensity of 60 mA for an on-period of at least 20 minutes. After the on-period, the controller terminates current flow, resulting in an off period. The off period may extend from 30 minutes to seven days. After the off period, the controller may a) initiate current flow at an intensity of less than 60 mA, such as 45 mA, for any period of time, b) initiate current flow at any intensity for less than 20 minutes, or c) initiate current flow at an intensity of less than 60 mA, such as 45 mA, for less than 20 minutes. This approach of having a larger initial current level and/or longer initial treatment period, decreasing to a lower current level and/or shorter treatment period may be automatically repeated over a number of subsequent treatment sessions and may be programmed expressly or implicitly by identifying a specific desired mode of treatment which provides for the differential current flow.
2. In one embodiment, the controller may be programmed to operate at a first frequency for a first period of time. After operating for the first period of time, the controller would shut off, terminating current flow. After a first off period, the controller may be programmed to operate at a second frequency for a second period of time, where the second frequency is less than or greater than the first frequency and/or the second period of time is less than the first period of time. For example, in one embodiment, the controller is programmed to operate at a first frequency of 10 Hz for an on-period of at least 10 minutes. After the on-period, the controller terminates current flow, resulting in an off period. The off period may extend from 5 minutes to seven days, or any time increment therein. After the off period, the controller may initiate a pulse at a frequency of less than 10 Hz or greater than 10 Hz for any period of time. This approach of having different frequencies (where each subsequent treatment session has a greater or lesser frequency than the preceding treatment session after an off-period) automatically delivered may be repeated over a number of subsequent treatment sessions and may be programmed expressly or implicitly by identifying a specific desired mode of treatment which provides for the differential current flow.
3. Identifying a specific mode of treatment (through one or more of the switches or graphical user interfaces described above), such as anxiety, obsessive compulsive disorder, post-traumatic stress disorder, memory degeneration, schizophrenia, attention deficient disorder, autism, Parkinson's disease, stroke rehabilitation, drug addiction, including addiction to, or cravings for, nicotine, cocaine, alcohol, heroine, methamphetamines, stimulants, and/or sedatives, depression and depression-related conditions, such as post-partum depression or bipolar depression, auditory hallucinations, erectile dysfunction, improved weight management, multiple sclerosis, fibromyalgia, Alzheimer' s disease, spinocerebellar degeneration, epilepsy, urinary incontinence, movement disorders, chronic pain, promoting neuroprotection, improved sleep, improved memory, relaxation, decreased stress, improved sexual function, chronic tinnitus, or sleep apnea, would result in the automated activation of any of the treatment protocols described in this specification or any combination of such treatment protocols.

Figure 29:
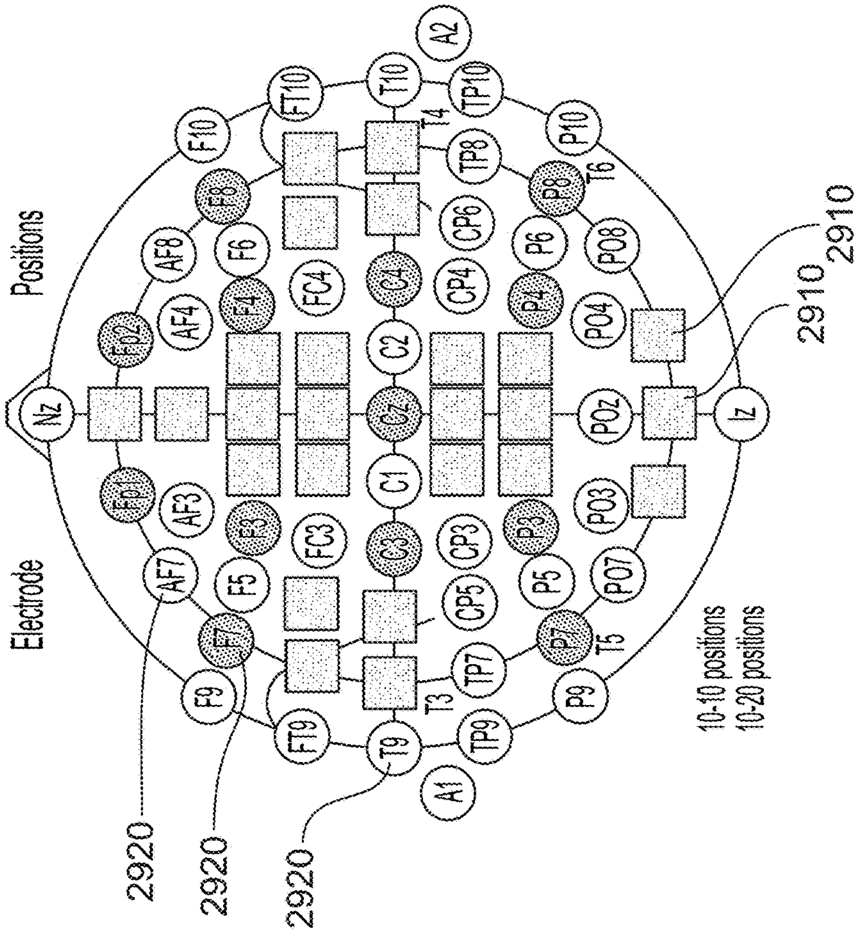
FIG. 29 shows a placement of microcoil arrays relative to a 10-10 and 10-20 EEG electrode placement map.

To tailor the delivery of the magnetic field intensity, treatment period, magnetic field pulse frequency, and/or directionality of the delivered field (based on which arrays distributed around the headwear should be activated), a plurality of EEG sensors may be integrated into the headwear. Referring to FIG. 28, the headwear 2800 comprising a substrate 2820 with a plurality of EEG electrodes 2820, such as dry or semi-dry electrodes (as opposed to wet electrodes), and the microcoil arrays 2810, as previously described. Referring to FIG. 29, the EEG electrodes 2920 are preferably positioned such that they do not overlap or physically interfere with the microcoil arrays 2910. Accordingly, referring to the 10-10 or 10-20 international standard for electrode positions, between 90% and 10% (or any increment therein), preferably between 75% and 40%, of the EEG electrode positions are available for use, since the remainder of the positions are occupied by microcoil arrays, as indicated by the blacked out symbols 2910 in FIG. 29.

In one embodiment, the EEG sensors capture data indicative of the varying magnitude of electric fields originating from the brain, including, but not limited to, delta brain waves (0.5 to 3 Hz), theta brain waves (3 to 8 Hz), alpha brain waves (8 to 12 Hz), beta brain waves (12 to 38 Hz), and gamma brain waves (38 to 42 Hz), and data indicative of a degree of coherence between different areas of the brain.

In one embodiment, the controller is configured to activate and/or obtain readings from EEG sensors only when current is not being generated and transmitted to the microcoil arrays.

To further tailor the delivery of the magnetic field intensity, treatment period, magnetic field pulse frequency, and/or directionality of the delivered field (based on which arrays distributed around the headwear should be activated), a plurality of programmatic instructions, stored on a memory and configured to execute in a computing device, such as a mobile phone, may generate, when executed by a processor, a visual analog scale. The visual analog scale solicits one or more of the following data inputs from a user of the headwear: degree of craving, degree of headache, degree of anxiety, degree of stress, degree of sleepiness, degree of pain in one or more anatomical locations, or one or more other emotions, physiological sensations, or symptoms. The visual analog scale may prompt the user for the data input using any graphical user interface that enables a user to designate an amount or degree, such as a numerical scale, graphical icons representing different levels, textual descriptions, or a color scale.

In one embodiment, at least one of the data generated by the VAS or the EEG sensors is used to modulate, change, or otherwise modify one or more of the stimulation parameters described in this specification, including which arrays are activated and in what sequence, the frequency of a pulse train, the shape of each pulse in the pulse train, the number of pulses in the pulse train, the amplitude of the current used in the pulse train, the ramping (including the rate of increase or decrease) of sequential pulses in the pulse train, when to activate, how long to operate, and when to terminate, based on a deep learning or neural network model applied to the acquired data. For example, as VAS or EEG data is acquired, the data is fed into the controller which is configured to apply a trained neural network or deep learning model on the data. That model is configured to relate various combinations of VAS or EEG values to various treatment protocols. Accordingly, as the VAS or EEG values change, the model determines whether the stimulation parameters, as described above, should modify and, if so, how and to what extent. In particular, the controller is configured to modify one or more of the stimulation parameters based on a degree of coherence determined based at least on EEG sensor measurements. The controller is configured to modify stimulation parameters to obtain a desired degree of coherence, such as increased coherence or decreased coherence, across one or more, or all of the, regions of the brain. Additionally, in particular, the controller is configured to modify a treatment session time based on data from prior treatment sessions, including VAS data, EEG data, or simply based on the length of time the prior treatment session ran for.

In one important embodiment, the system may be used as a repetitive transcranial magnetic stimulation system to detect epileptic seizures and, in response, generate magnetic fields that suppress an epileptic seizure. When the EEG-based detection system detects a possible seizure, the controller generates a current, directed to each of the microcoil arrays concurrently or sequentially, resulting in pulsed, multi-directional magnetic fields having a frequency that is below 5 Hz, preferably at or below 1 Hz, and more preferably 0.5 Hz. Referring to FIG. 30, the EEG electrodes are configured to detect brain waves and generate corresponding analog signals 3002. The analog signals are transmitted to the controller, which converts it to digital signals, samples the digital signals, and segments the sampled signals into short windows (5 seconds or less) 3004. The signals are then subj ected to any number of different analytical programs to identify whether a seizure is occurring or is imminent 3006. Such analytical programs may comprise deep learning techniques, conventional neural networks, recurrent neural networks, autoencoders that use deep fusional attention networking, and long short-term memory architecture. In one preferred approach, each channel of EEG data is treated as individual node or oscillator in a synchronization network. Patterns are found by estimating the coupling intensity functions (both power and phase related coupling coefficients) between the individual nodes (EEG channels) of the network during seizure onsets. In order to compute the time-varying power of the coupling functions in the network between adjacent sets of nodes, a Fast Fourier transform is applied on short epochs (0.25-1 seconds) segmented from each channel of the EEG data. The resulting sets of coupling intensities are then transposed onto a Laplacian matrix, where eigenvalues are computed at each time step and used as a key extracted feature to determine seizure state. The value of that extracted feature is compared to a threshold value to determine if a seizure is occurring or is imminent. Depending on the accuracy of the prediction, the gamma value parameter can be tuned to increase the accuracy and resistance to noise/artifact interference. Due to the certain level of synchronicity in brain signals during a seizure, this dynamic graph-theoretic approach of analyzing synchronicity allows for the accurate and computationally light detection of seizure with possibly noisy measurement data from dry or semi-dry systems. In practice, a clinician would determine the threshold value on a patient-by-patient basis, tuning the sensitivity of the detection system to each specific patient.

Once the controller, executing the EEG detection model, detects a seizure, a signal is generated to initiate current flow to the microcoil arrays, in any one of the treatment protocols described herein 3008, at a frequency of 5 Hz or less, preferably 1 Hz or less, and most preferably at 0.5 Hz. In one embodiment, all the microarrays are activated concurrently. In another embodiment, the microarrays are activated in groups (with more than 1 but not all of the arrays concurrently activated) or sequentially (with only one array on at a time). After a predetermined period of time, such as 1 to 60 minutes (or any time increment therein) of operation, the controller of the integrated seizure detection and repetitive transcranial magnetic stimulation system is configured to turn off the current being directed to the microcoil arrays and reinitiate the detection model to continue monitoring for seizures 3010.

In sum, the embodiments described herein achieve an alleviation of symptoms related to anxiety disorders, obsessive compulsive disorder, post-traumatic stress disorder, memory degeneration, schizophrenia, attention deficient disorder, autism, Parkinson's disease, stroke rehabilitation, drug addiction, including addiction to, or cravings for, nicotine, cocaine, alcohol, heroine, methamphetamines, stimulants, and/or sedatives, depression and depression-related conditions, such as post-partum depression or bipolar depression, auditory hallucinations, erectile dysfunction, improved weight management, multiple sclerosis, fibromyalgia, Alzheimer's disease, spinocerebellar degeneration, epilepsy, urinary incontinence, movement disorders, sinus inflammation, sinusitis, chronic pain, sleep disorders, insomnia, memory disorders, stress, sexual function dysfunction, chronic tinnitus, high blood pressure, or sleep apnea while the magnetic fields are being applied to the brain by increasing a user's feelings of calm or relaxation, decreasing the user's feelings of anxiety, depression, confusion, cravings, pain, distraction, modulating the user's blood pressure, glucose level or other physiological parameters, or improving a user's motor control, memory, or degree or amount of contiguous deep sleep, sexual function.

Other Applications

It should further be appreciated that other embodiments may be specifically designed to be directed toward 1) treating osteoporosis by, for example, positioning a plurality of arrays along a length of substrate configured to extend over an entire length of a user's spine, each of said arrays being in electrical communication with a controller, 2) effectuating an activation of acupoints that may be distributed over various areas of the user's body, where at each acupoint an array is positioned and where all of the arrays are in electrical communication with a controller; optionally, a coil that aligns with an acupoint may be configured to receive a higher level of current and generate a higher magnetic flux than the rest of the coils which are not aligned with an acupoint, 3) treating a neck region to reduce increase and increase a collagen framework, where a plurality of arrays are configured to extend around a neck region of the user, each of the arrays being in electrical communication with a controller, and 4) treating one or more broken bones by providing a plurality of arrays configured to be positioned on a user's skin and between a cast and the user's skin, each of the arrays being electrical communication with a controller.

Figure 19:
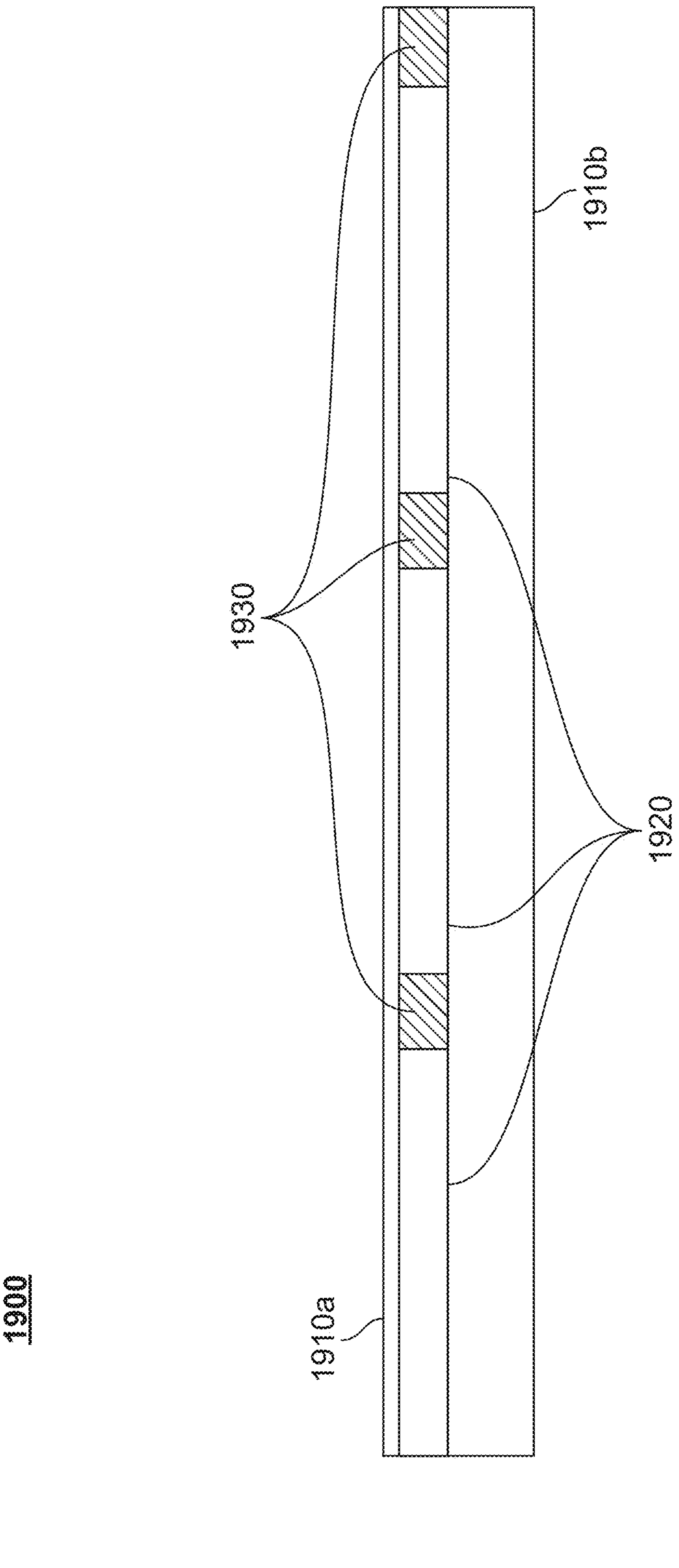
FIG. 19 is a side view of an article of clothing with planar microcoil arrays integrated therein.

Referring to FIG. 19, an article of clothing with a set of planar microcoils integrated therein 1900. A layer of clothing 1910*b*, which faces the outside environment, has, positioned on top of it, and opposing the outside layer, a set of planar microcoil arrays 1920 that are connected by traces. A layer of clothing 1910*a*, configured to face the skin of a user, is positioned on top of the set of planar microcoil arrays 1920. In one embodiment, the layer of clothing 1910*a* is contiguous and uniform. In another embodiment, the layer of clothing 1910*a* has a window that exposes the coils of the arrays, and therefore the generated magnetic fields, to the skin of the user. The window may be just a space or made of a different material, such as a clear plastic or a thinner material than the rest of layer 1910*a*. A buffer material 1930 may be positioned between the arrays to keep the arrays 1920 in position and physically separated from each other. The buffer material may be any non-conductive material, including cotton, polyester, or wool.

Figure 20:
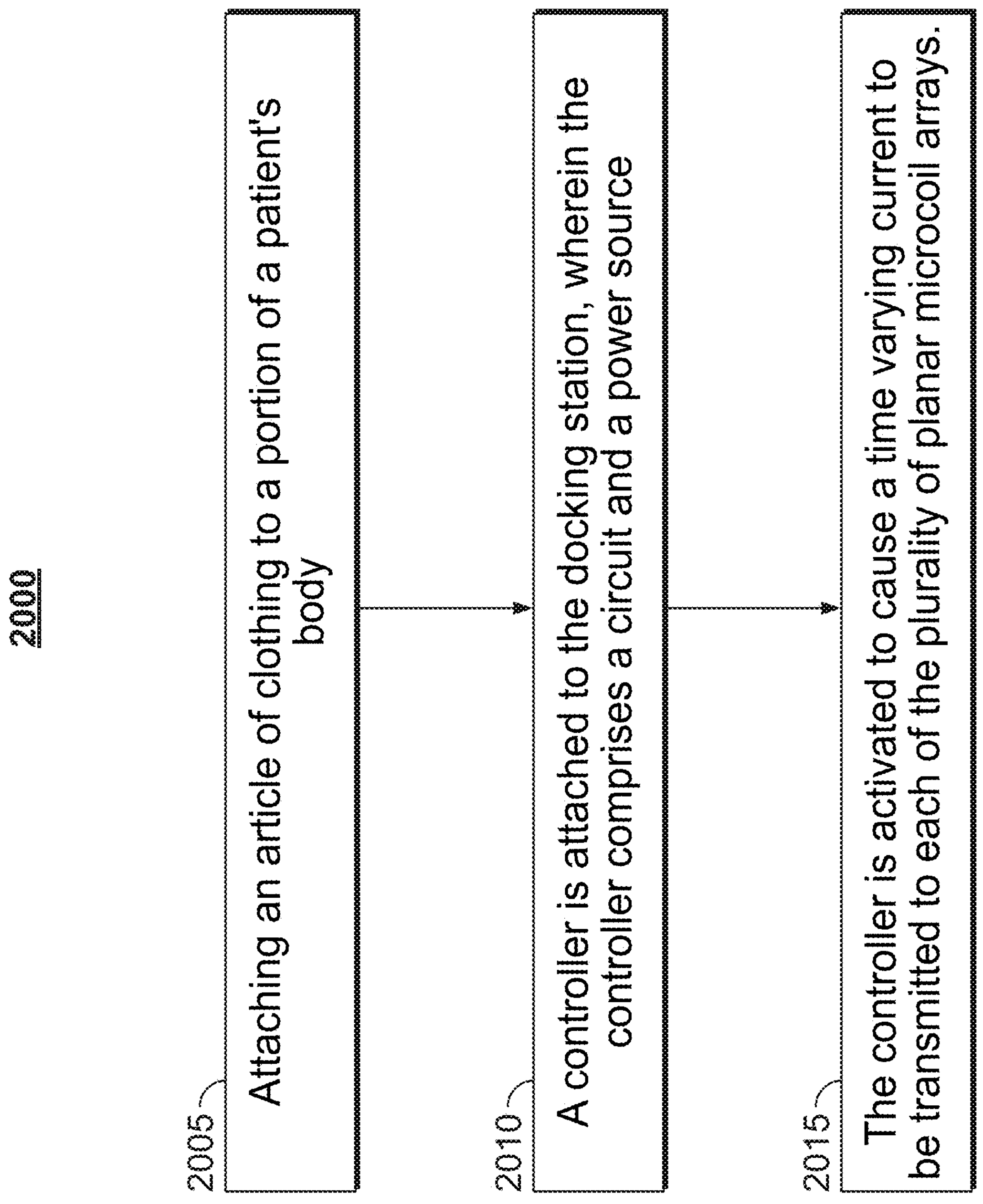
FIG. 20 shows an exemplary method of using the PEIViF device.

Referring to FIG. 20, in one embodiment, a method 2000 of treating a condition is provided. An article of clothing is attached 2005 to a portion of a patient's body. The article of clothing comprises a plurality of planar microcoil arrays, wherein each of the plurality of planar microcoil arrays comprises two or more planar microcoils positioned on a flexible substrate, wherein each of the plurality of planar microcoil arrays is integrated into the article of clothing;

and wherein each of the plurality of planar microcoil arrays is in electrical communication with a docking station integrated into the article of clothing. A controller is attached 2010 to the docking station, wherein the controller comprises a circuit and a power source. Preferably, upon attaching the controller to the docking station, the circuit automatically electrically interfaces with at least one of the plurality of planar microcoil arrays. The docking station is optional. The controller may be directly integrated into the article of clothing. The controller is activated 2015 to cause a time varying current to be transmitted to each of the plurality of planar microcoil arrays.

The article of clothing may be attached such that at least one of the two or more planar microcoils in at least one of the plurality of planar microcoil arrays is positioned over an acupoint of the patient's body. Additionally, prior to attaching the article of clothing, a skin impedance measurement may be made and, based on the level of impedance, the article of clothing may be attached such that at least one of the two or more planar microcoils in at least one of the plurality of planar microcoil arrays is positioned over an area of impedance that exceeds a predefined threshold value. Accordingly, an impedance measurement sensor and circuit may also be integrated into the article of clothing.

Figure 31A:
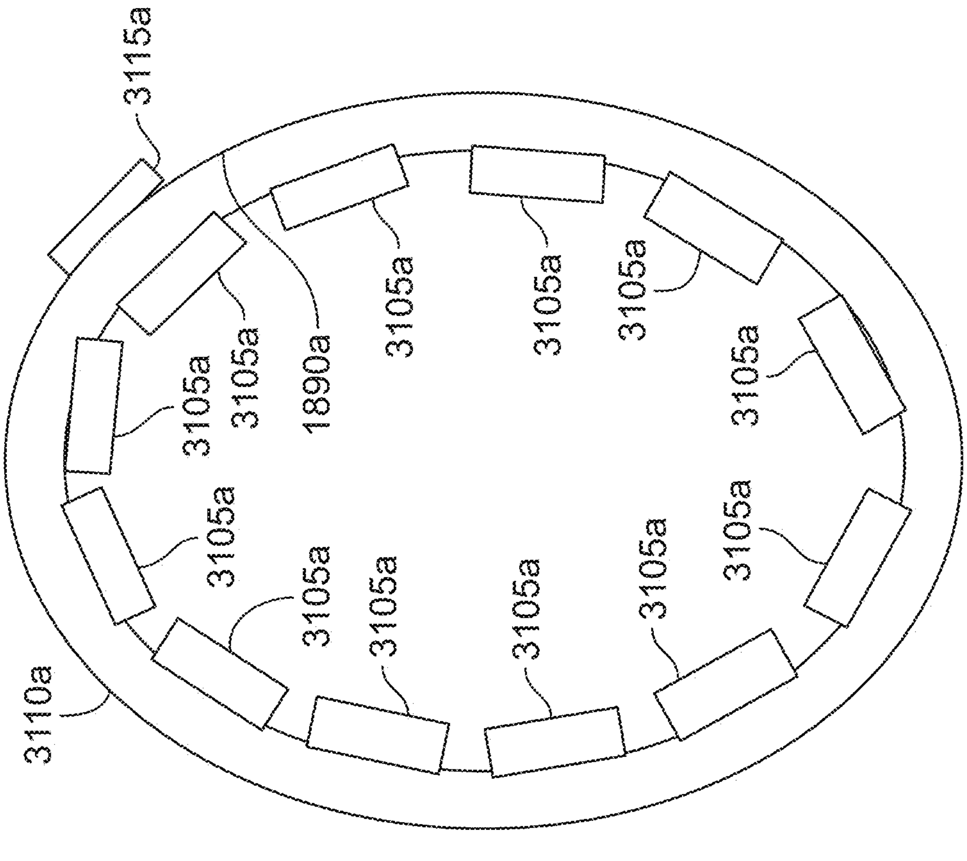
FIG. 31A shows a first exemplary device for treating symptoms related to metabolic syndrome, high glucose, and viral infections, among other conditions.
Figure 31B:
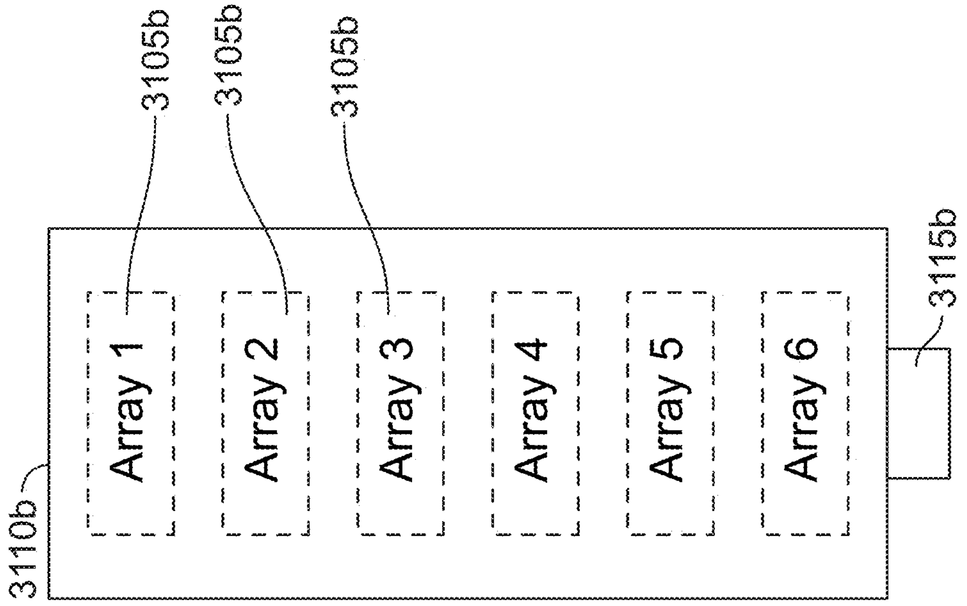
FIG. 31B shows a second exemplary device for treating symptoms related to metabolic syndrome, high glucose, and viral infections, among other conditions.
Figure 32:
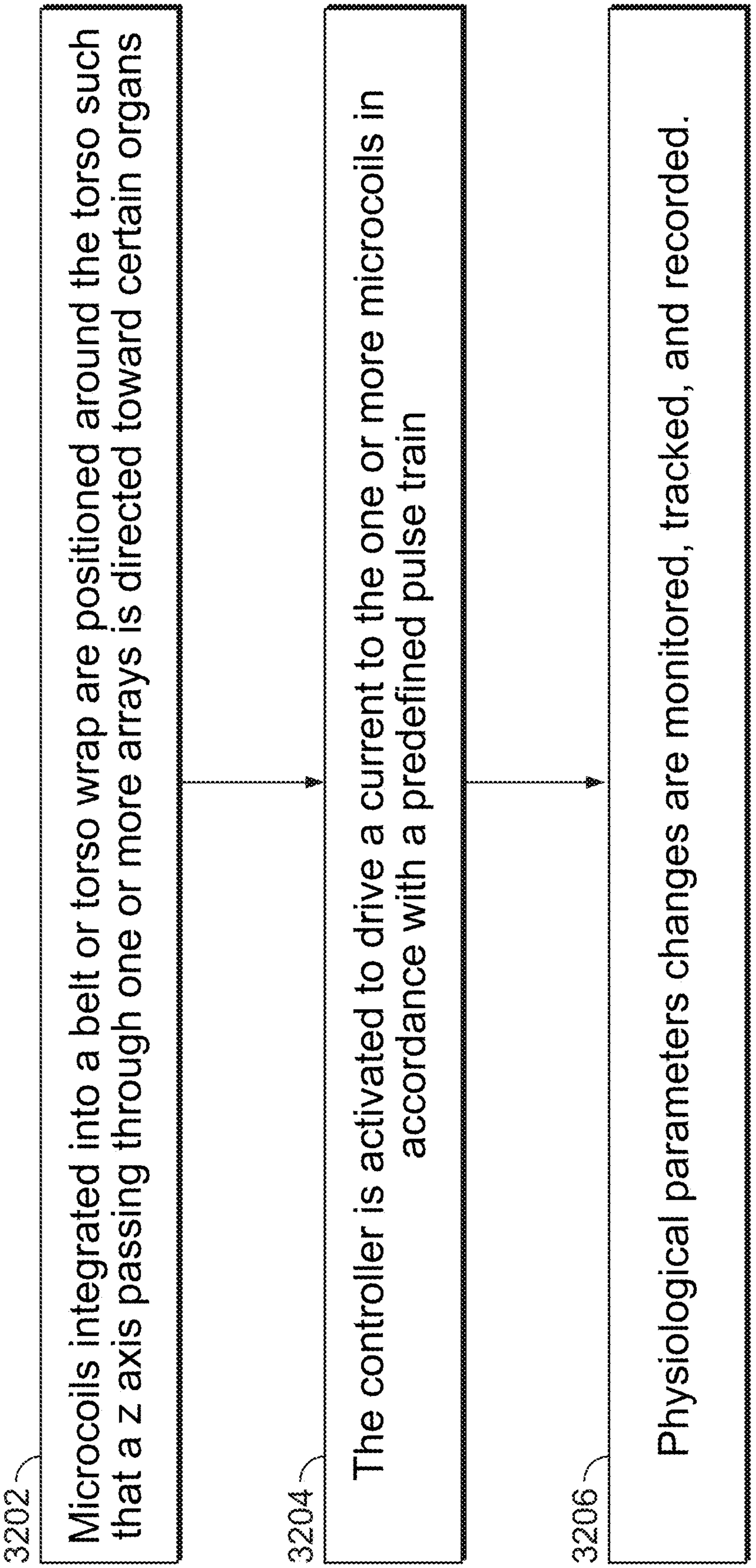
FIG. 32 shows an exemplary method for treating symptoms related to metabolic syndrome.
Figure 33C:
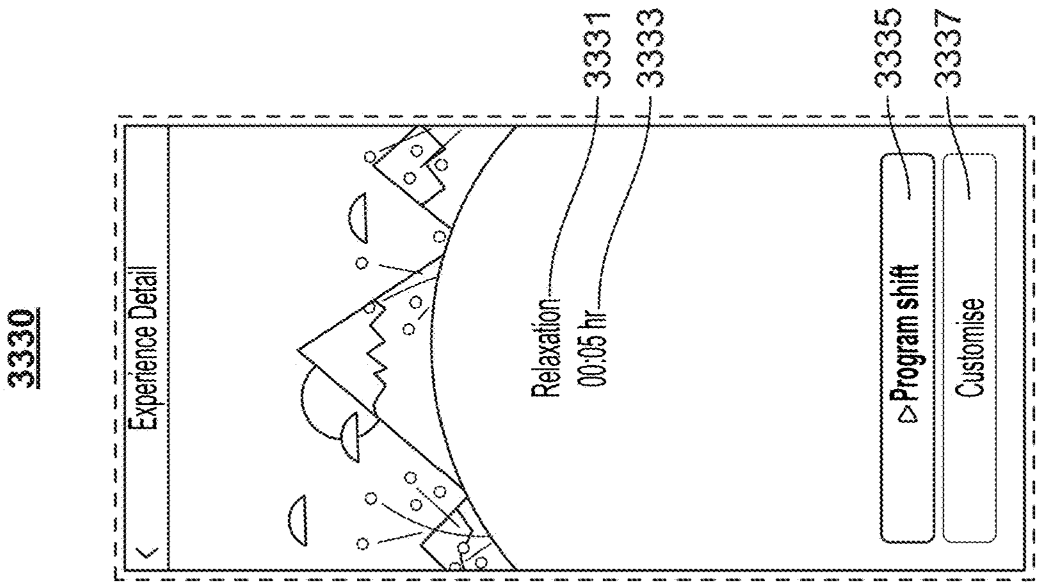
FIG. 33C shows a third exemplary graphical user interface in the software program configured to program and/or control the controller.
Figure 33B:
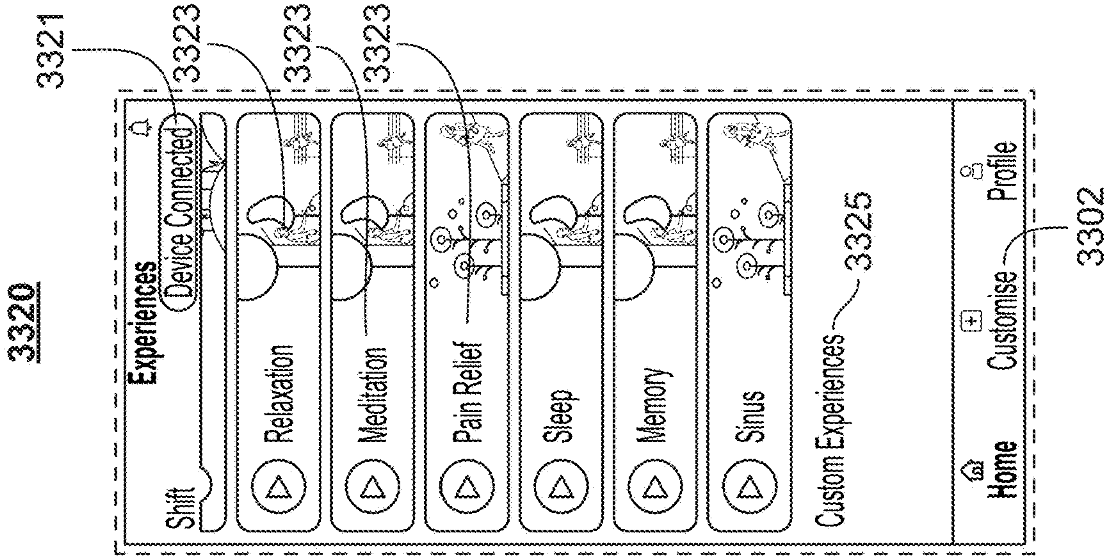
FIG. 33B shows a second exemplary graphical user interface in the software program configured to program and/or control the controller.
Figure 33A:
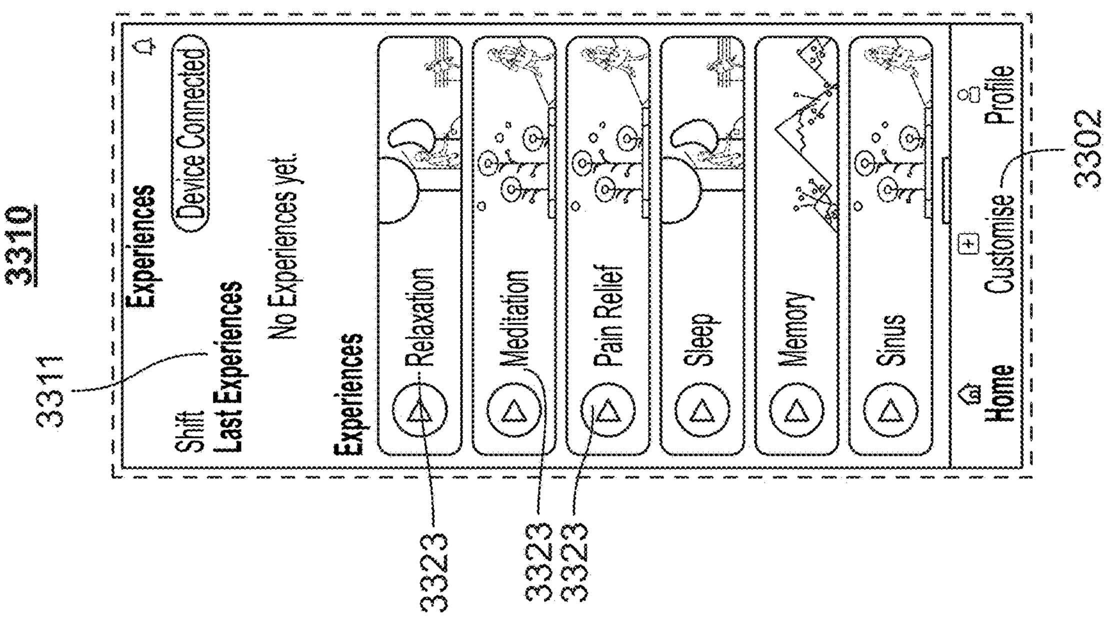
FIG. 33A shows a first exemplary graphical user interface in the software program configured to program and/or control the controller.
Figure 33D:
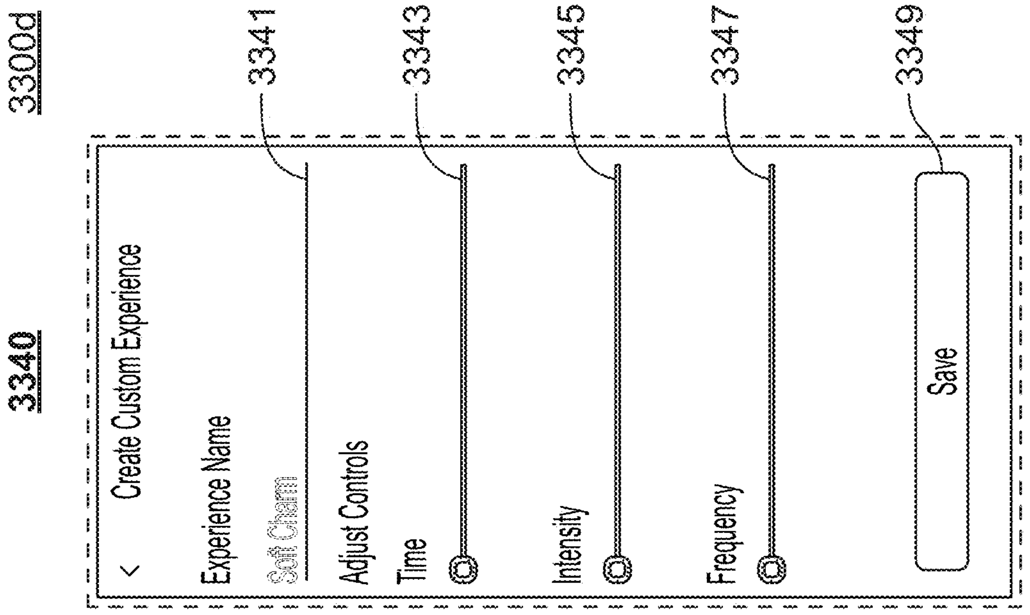
FIG. 33D shows a fourth exemplary graphical user interface in the software program configured to program and/or control the controller.

Referring to FIGS. 31A, 31B and 32, any of the arrays 3105*a*, 3105*b* described in this specification may be integrated into a belt, torso wrap, or other fabric configured to encircle a human torso 3110*a* or simply lay across an area of the patient's body 3110*b*, i.e. in the form of a largely linear fabric. The device 3100*b* may be linear and configured to just lay over a portion of the user's body or attach, using thread, Velcro, snaps, or any other attachment means, to another article of clothing such that the fabric 3110*b* is positioned at the right location on the user's body.

In one embodiment, the arrays 3105*a*, 3105*b* are integrated into the fabric 3110*a*, 3110*b* such that the coils face, and are directed to, the user. Preferably, the coil arrays 3105*a* are distributed around the fabric 3110*a* such that they are distributed around, and therefore encircle the entirety of, the user's torso or distributed across the length of the substrate 3110*b* such that the arrays 3105*b* are positioned adjacent each other. The arrays are electrically coupled to a controller 3115*a*, 3115*b* that is integrated into a surface of the substrate 3110*a*, 3110*b* or separate from the substrate 3110*a*, 3110*b*. When worn, the device 3100*a*, 3100*b* is positioned such that it is proximate (within at least 20 inches, within at least 15 inches, within at least 10 inches or within at least 5 inches) one or more of the following organs, or portions thereof: the user's liver, gall bladder, heart, lung, stomach, colon, kidneys, spleen, pancreas, large intestine, small intestine. Referring to FIG. 32, the substrate 3110*a*, 3110*b* integrated with the microcoil arrays are positioned around the user's torso 3202. The controller 3115*a*, 3115*b* is activated such that a current is driven to the one or more microcoils in accordance with any of the pulse trains or stimulation protocols 3204 described in this specification. Preferably, one or more physiological parameters, including a glucose level, a blood pressure, pulse rate, $SpO_2$ level, core temperature, cortisol level, or lymphocyte activity, are subsequently tracked and recorded 3206.

Using an encircling belt or a linear length of fabric placed over a) the front upper torso and upper back of the user and/or b) around the neck of the user can have several benefits. First, it may help improve user's metabolic rate, thereby helping increase weight loss and increase the rate of calories being expended by the user. Second, it may help the metabolism of glucose, thereby decreasing the user's blood sugar relative to the user's blood sugar level without the device. It should be appreciated that any of the frequencies, current intensities, pulse shapes, pulse widths, or time of treatment session disclosed in this specification may be used. In one embodiment, a frequency in a range of 8-60 Hz, a treatment time in a range of 10 minutes to 2 hours, a configuration where both the front upper torso and upper back are being exposed either through an encircling wrap or two separate linear devices, a rectangular ramping pulse, and a field intensity in range of 500 microTesla and below.

Third, it may increase blood oxygenation levels by increasing the expression of nitric oxide in blood vessels and the lungs. Nitric oxide serves as a vasodilator and can improve the endothelial function of vessels. This is a similar mechanism of action that leads to improved cerebral oxygenation levels, as described above. Nitric oxide expression may also serve to suppress the coronaviruses responsible for COVID, such as SARS-CoV or SARS-CoV-2. Accordingly, in one embodiment, the present specification discloses systems and methods for treating symptoms of SARS-CoV-2 infection by a) placing a device with the aforementioned arrays comprising microcoils and a controller on the upper torso of the patient and preferably on the upper back of the patient, b) concurrently initiating a treatment session defined by any of the frequencies, current intensities, pulse shapes, pulse widths, or time of treatment session disclosed in this specification and more particularly defined by a frequency in a range of 8-60 Hz, a treatment time in a range of 10 minutes to 2 hours, a rectangular ramping pulse, and a field intensity in range of 500 microTesla and below, and c) tracking blood oxygenation level and pulse rate of the patient. If the pulse rate increases and exceeds 100 beats per minute, the controller is turned off and therapy is terminated. If the blood oxygenation level decreases, the controller is turned off and therapy is terminated.

It should be appreciated that, for each of the embodiments disclosed herein, the unexpectedly effective therapies are enabled by a unique device design having one or more of the following features which, when taken together, efficiently enable an intelligent direction shifting (Intelligent Directional Shifting or IDS) of magnetic field lines:

1. Two or more flexible substrates each comprising two or more non-linear electrically conductive structures (preferably spiral or coiled structures) integrated or embedded therein such that, when electrical current is passed therethrough, each of the two or more non-linear electrically conductive structures independently, yet concurrently, generate separate and distinct magnetic fields. Preferably, a center point of the two or more non-linear electrically conductive structures are positioned sufficient proximate to each other on the same flexible substrate, e.g. on the order of less than 5 inches and preferably less than 1 inch.
2. The two or more flexible substrates are not integrally formed or directly attached, thereby allowing them to be spaced apart and allowing for the two or more non-linear electrically conductive structures to generate magnetic fields in different directions.
3. The two or more flexible substrates encircle an organ or set of organs to be modulated by pulsed electromagnetic fields, thereby ensuring the same volume of tissue is exposed to magnetic field lines that directionally vary or shift in space over a single treatment session. For example, when applying pulsed electromagnetic fields to the user's brain, the flexible substrates are positioned around the front, left side, right side, top, and back of the user's head, thereby ensuring that the same volume of the user's brain experiences magnetic field lines traveling from, and to, at least five different directions over a single treatment session. Preferably the same volume of tissue experiences field lines traveling from, and to, at least two, three, four, five, six, seven, eight, nine, ten, eleven, twelve, thirteen, fourteen, fifteen, sixteen, seventeen, eighteen, nineteen, twenty or more than twenty different directions during one treatment session which typically lasts for less than 6 hours, preferably less than 2 hours, more preferably less than 1 hour and even more preferably less than 30 minutes.
4. A controller that selectively activates each of the two or more flexible substrates sequentially, concurrently, or selectively such that the same volume of tissue is exposed to magnetic field traveling from, and to, only a subset (and not all) of the available magnetic field directions, such as two, three, four, five, six, seven, eight, nine, ten, eleven, twelve, thirteen, fourteen, fifteen, sixteen, seventeen, eighteen, nineteen, twenty different directions during a single treatment session, which may last for less than 6 hours, less than 1 hour, less than 30 minutes, or less than 10 minutes or every time increment therein.
5. In one preferred embodiment, during a single treatment session, which may last for less than 6 hours, less than 1 hour, less than 30 minutes, or less than 10 minutes or every time increment therein, the controller selectively activates each of the two or more flexible substrates sequentially. For example, where there are between 4 and 25 separate and distinct flexible substrates, each having two or more coils that are serially energized or energized in parallel to generate a magnetic field, a first subset of the flexible substrates would be positioned proximate the user's frontal lobe, a second subset of the flexible substrates would be positioned proximate the user's left temporal lobe, a third subset of the flexible substrates would be positioned proximate the user's right temporal lobe, a fourth subset of the flexible substrates would be positioned proximate the user's parietal lobe, and a fifth subset of the flexible substrates would be positioned proximate the user's occipital lobe. The controller is programmed to drive current to the flexible substrates such that the current is directed to each of the first, second, third, fourth, and fifth subsets, in any order, and such that each of the subsets receives the current for less than 5 continuous minutes each, preferably less than 3 continuous minutes each, and preferably less than 1 continuous minute each. The controller repeats this sequence (sequentially directing current to each of the first, second, third, fourth, and fifth subsets, in any order, such that each of the subsets receives the current for less than 5 continuous minutes each, preferably less than 3 continuous minutes each, and preferably less than 1 continuous minute each) throughout the entire treatment session.

Finally, some or all of the embodiments described in this specification may be accompanied by one or more accessories:

1. A charging base configured to fit on or within the article of clothing, such as a dome or any convex surface that is shaped to receive the hat, cap, or face covering described herein, a shoe tree to receive the footwear described herein, or any other shape configured to mimic an anatomical surface. Once the article of clothing is positioned on the charging base, the charging terminal of the base automatically interfaces with the charging terminal of the article of clothing, thereby automatically placing the article of clothing in a charging state.
2. A protective case configured to fit over the article of clothing, such as a dome or any convex surface that is shaped to cover the hat, cap, or face covering described herein, a shoe box to receive the footwear described herein, or any other shape configured to cover the device. Once the article of clothing is positioned in the protective case, the charging terminal of the protective case automatically interfaces with the charging terminal of the article of clothing, thereby automatically placing the article of clothing in a charging state.
3. Disposable liners, made of mesh-like cloth, woven cotton, woven polyester, or viscose rayon, that have the same shape as the article of clothing and useful to act as an intermediate layer between the user and the article of clothing, like a dome shaped liner to cover the user's head when he or she puts on the hat, cap, or face covering described herein. For example, a user may first put on the disposable liner and then put on one or more of the articles of clothing described herein.

4. Elastic bands extending around one or more positions of the article of clothing to secure the article of clothing to the user, such as an elastic band attached to the crown of the hat and extending downward below the user's chin or skull base.

While the exemplary embodiments of the present invention are described and illustrated herein, it will be appreciated that they are merely illustrative. It will be understood by those skilled in the art that various changes in form and detail may be made therein without departing from or offending the spirit and scope of the invention. Furthermore, it should be appreciated that any feature, component, structure, or process step disclosed with respect to one embodiment may be equally applied or integrated into any other embodiment. For example, any of the stimulation protocols, mechanisms of action, magnetic field profile configurations, controller configurations that may apply to the headwear embodiment will similarly apply to other applications, such as the footwear or torso applications.

We claim:

1. A pulsed electromagnetic field device configured to direct pulsed electromagnetic fields toward a brain of a user, comprising:

a head covering having an internal surface configured to receive a head of the user, wherein the head covering has a left side, a right side, a top side, a front side and a back side;

at least two planar flexible arrays, wherein:

each of the at least two planar flexible arrays comprises at least one planar microcoil integrated into a flexible substrate;

a first of the at least two planar flexible arrays is coupled to at least one of the left side, the right side, the top side, the front side or the back side of the head covering; and a second of the at least two planar flexible arrays is coupled to at least one of the left side, the right side, the top side, the front side or the back side and is not on a same side as the first of the at least two planar flexible arrays; and a controller configured to be electrically coupled to each of the at least two planar flexible arrays and configured to generate an electrical current, wherein each array of the at least two planar flexible arrays is configured to receive the electrical current and generate separate pulsed electromagnetic fields, wherein, during a treatment session, the controller is configured to temporally alternate electrical current delivery by directing the electrical current to the first of the at least two planar flexible arrays for a first period of time and subsequently directing the electrical current to the second of the at least two planar flexible arrays for a second period of time, wherein the first period of time and the second period of time are temporally sequential and mutually exclusive such that the first of the at least two planar flexible arrays emits a first magnetic field for the first period of time and does not emit a magnetic field during the second period of time, wherein the second of the at least two planar flexible arrays emits a second magnetic field for the second period of time and does not emit a magnetic field during the first period of time and wherein the first and second planar flexible arrays are positioned such that the brain experiences magnetic field lines traveling in different directions during the treatment session.

2. The pulsed electromagnetic field device of claim 1, wherein each of the first period of time and the second period of time is less than five minutes.

3. The pulsed electromagnetic field device of claim 1, wherein the treatment session is less than 6 contiguous hours.

4. The pulsed electromagnetic field device of claim 1, wherein the controller is configured to direct the electrical current to each of the at least two planar flexible arrays such that, over the treatment session, a same volume of the user's brain is exposed to the separate pulsed electromagnetic fields, wherein the separate pulsed electromagnetic fields change direction depending on which of the at least two planar flexible arrays is receiving the electrical current.

5. The pulsed electromagnetic field device of claim 1, wherein the electrical current is defined by an electrical pulse train having a frequency in a range of 0.1 Hz to 60 Hz and wherein pulses of the electrical pulse train have a substantially rectangular shape.

6. The pulsed electromagnetic field device of claim 5, wherein said pulses have different peak levels of current and wherein the different peak levels are in a range of 5 mA to 500 mA.

7. The pulsed electromagnetic field device of claim 1, wherein the electrical current is defined by an electrical pulse train, wherein, during the first period of time, the electrical pulse train comprises at least two pulses having different current amplitudes, and wherein, during the second period of time, the electrical pulse train also comprises at least two pulses having different current amplitudes.

8. The pulsed electromagnetic field device of claim 1, wherein each of the at least two planar flexible arrays comprises at least 4 spiral-shaped planar microcoils that are each embedded into the flexible substrate.

9. The pulsed electromagnetic field device of claim 8, wherein the controller is adapted to direct the electrical current to each of the at least 4 planar microcoils in the first of the at least two planar flexible arrays concurrently during the first period of time and to each of the at least 4 planar microcoils in the second of the at least two planar flexible arrays concurrently during the second period of time.

10. The pulsed electromagnetic field device of claim 1, further comprising a third of the at least two planar flexible arrays, wherein the third of the at least two planar flexible arrays is coupled to at least one of the left side, the right side, the top side, the front side or the back side and is not on the same side as the first of the at least two planar flexible arrays or on a same side as the second of the at least two planar flexible arrays.

11. The pulsed electromagnetic field device of claim 10, wherein the electrical current is defined by an electrical pulse train, wherein each of the first, second, and third of the at least two planar flexible arrays receives the electrical pulse train at a frequency in a range of 1 Hz to 100 Hz and wherein the controller is configured to sequentially deliver the electrical pulse train to each of the first, second, and third of the at least two planar flexible arrays.

12. The pulsed electromagnetic field device of claim 1, wherein the head covering comprises two or more layers of material and wherein the first of the at least two planar flexible arrays and the second of the at least two planar flexible arrays are positioned between the two or more layers of material.

13. The pulsed electromagnetic field device of claim 11, wherein the electrical pulse train comprises at least a first pulse having a first amplitude, a second pulse having a second amplitude, and a third pulse having a third amplitude, wherein the first amplitude is less than the second amplitude and the second amplitude is less than the third amplitude.

14. The pulsed electromagnetic field device of claim 13, wherein each of the first pulse, the second pulse, and the third pulse has a substantially rectangular shape.

15. The pulsed electromagnetic field device of claim 1, wherein the first of the at least two planar flexible arrays and the second of the at least two planar flexible arrays each comprise at least two planar microcoils, an input terminal configured to receive the electrical current from the controller and direct the electrical current to the at least two planar flexible arrays, an output terminal configured to receive the electrical current from the at least two planar flexible arrays, and traces that electrically connect each of the at least two planar microcoils to the respective input terminal and the respective output terminal.

16. The pulsed electromagnetic field device of claim 1, wherein the head covering comprises a crown defined by the left side, the right side, the top side, the front side and the back side and a brim attached to said crown.

17. The pulsed electromagnetic field device of claim 1, wherein, during the first period of time, the first of the at least two planar flexible arrays generates a first magnetic field defined by a first vector extending in a first direction, wherein, during the second period of time, the second of the at least two planar flexible arrays generates a second magnetic field defined by a second vector extending in a second direction, and wherein if the first vector and the second vector were to intersect each other, the first vector and the second vector would form an angle having a value greater than 15 degrees.

18. A pulsed electromagnetic field device configured to direct pulsed electromagnetic fields toward a brain of a user, comprising:

a head covering defined by a crown having an internal surface configured to receive a head of the user, wherein the crown has a left side, a right side, a top side, a front side and a back side;

at least three planar arrays, wherein:

each of the at least three planar arrays comprises at least two planar microcoils integrated into a substrate;

a first of the at least three planar arrays is coupled to at least one of the left side, the right side, the top side, the front side or the back side of the crown;

a second of the at least three planar arrays is coupled to at least one of the left side, the right side, the top side, the front side or the back side and is not on a same side as the first of the at least three planar arrays; and a third of the at least three planar arrays is coupled to at least one of the left side, the right side, the top side, the front side or the back side and is not on the same side as the first of the at least three planar arrays or on a same side as the second of the at least three planar arrays; and a controller configured to be electrically coupled to each of the at least three planar arrays and configured to generate an electrical current, wherein each array of the at least three planar arrays is configured to receive the electrical current and generate separate pulsed electromagnetic fields, wherein, during a treatment session, the controller is configured to direct the electrical current to the first of the at least three planar arrays for a first period of time, configured to temporally alternate electrical current delivery by directing the electrical current to the second of the at least three planar arrays for a second period of time, and subsequently directing the electrical current to the third of the at least three planar arrays for a third period of time, wherein the first period of time, the second period of time, and the third period of time are temporally sequential and mutually exclusive such that the first of the at least three planar arrays emits a first magnetic field for the first period of time and does not emit a magnetic field during the second period of time or the third period of time, the second of the at least three planar arrays emits a second magnetic field for the second period of time and does not emit a magnetic field during the first period of time or the third period of time, and the third of the at least three planar arrays emits a third magnetic field for the third period of time and does not emit a magnetic field during the first period of time or the second period of time and wherein the first, second and third planar arrays are positioned such that the brain experiences magnetic field lines traveling in different directions during the treatment session.

19. The pulsed electromagnetic field device of claim 18, wherein each of the first period of time, the second period of time, and the third period of time is less than five minutes.

20. The pulsed electromagnetic field device of claim 18, wherein the electrical current is defined by an electrical pulse train having a frequency in a range of 1 Hz to 60 Hz, wherein pulses of the electrical pulse train have a substantially rectangular shape, wherein said pulses of the electrical pulse train have different peak levels of current, and wherein the different peak levels are in a range of 5 mA to 500 mA.

21. The pulsed electromagnetic field device of claim 18, wherein the first of the at least three planar arrays, the second of the at least three planar arrays, and the third of the at least three planar arrays each comprise at least four planar microcoils, an input terminal configured to receive the electrical current from the controller and direct the electrical current to the at least three planar arrays, an output terminal configured to receive the electrical current from the at least three planar arrays, and traces to electrically connect each of the at least four planar microcoils to the respective input terminal and the respective output terminal.

22. The pulsed electromagnetic field device of claim 18, wherein, during the first period of time, the first of the at least three planar arrays generates a first magnetic field defined by a first vector extending in a first direction, wherein, during the second period of time, the second of the at least three planar arrays generates a second magnetic field defined by a second vector extending in a second direction, wherein, during the third period of time, the third of the at least three planar arrays generates a third magnetic field defined by a third vector extending in a third direction, and wherein if the first vector and the second vector were to intersect each other, the first vector and the second vector would form an angle having a value greater than 15 degrees and if the second vector and the third vector were to intersect each other, the second vector and the third vector would form an angle having a value greater than 15 degrees.

* * * * *